(12) United States Patent
Brezski et al.

(10) Patent No.: US 9,611,328 B2
(45) Date of Patent: **\*Apr. 4, 2017**

(54) ACTIVE PROTEASE-RESISTANT ANTIBODY FC MUTANTS

(71) Applicant: JANSSEN BIOTECH, INC., Horsham, PA (US)

(72) Inventors: Randall Brezski, Spring House, PA (US); Robert Jordan, Thorton, PA (US); William Strohl, Spring House, PA (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/492,250

(22) Filed: Sep. 22, 2014

(65) Prior Publication Data

US 2015/0139984 A1     May 21, 2015

Related U.S. Application Data

(63) Continuation of application No. 13/555,334, filed on Jul. 23, 2012, now Pat. No. 8,871,204, which is a continuation-in-part of application No. PCT/US2011/065174, filed on Dec. 15, 2011.

(60) Provisional application No. 61/426,719, filed on Dec. 23, 2010, provisional application No. 61/540,882, filed on Sep. 29, 2011.

(51) Int. Cl.
| | |
|---|---|
| *A61K 38/00* | (2006.01) |
| *C07K 16/00* | (2006.01) |
| *C07K 16/30* | (2006.01) |
| *C07K 16/22* | (2006.01) |
| *C07K 16/28* | (2006.01) |
| *C07K 16/40* | (2006.01) |

(52) U.S. Cl.
CPC .............. *C07K 16/30* (2013.01); *C07K 16/00* (2013.01); *C07K 16/22* (2013.01); *C07K 16/2863* (2013.01); *C07K 16/2887* (2013.01); *C07K 16/2896* (2013.01); *C07K 16/40* (2013.01); *C07K 2317/52* (2013.01); *C07K 2317/524* (2013.01); *C07K 2317/53* (2013.01); *C07K 2317/72* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,660,266 | B1 | 12/2003 | Mosser et al. |
| 6,838,254 | B1 | 1/2005 | Hamers et al. |
| 7,129,331 | B2 | 10/2006 | Pestka |
| 7,666,582 | B2 | 2/2010 | Pawel-Rammingen et al. |
| 8,188,231 | B2 | 5/2012 | Lazar et al. |
| 8,729,985 | B2 | 5/2014 | Bullock et al. |
| 8,871,204 | B2 * | 10/2014 | Brezski .................. C07K 16/00 424/130.1 |
| 2008/0206867 | A1 | 8/2008 | Desjarlais et al. |
| 2009/0136526 | A1 | 5/2009 | McDonagh et al. |
| 2009/0155280 | A1 | 6/2009 | Jordan et al. |
| 2010/0260751 | A1 | 10/2010 | Raju et al. |
| 2010/0298542 | A1 | 11/2010 | Igawa et al. |

FOREIGN PATENT DOCUMENTS

| | | |
|---|---|---|
| EP | 1176195 B1 | 5/2013 |
| WO | WO 00/42072 A2 | 8/2000 |
| WO | WO 00/61739 A1 | 10/2000 |
| WO | WO 2006/071877 A2 | 7/2006 |
| WO | WO 2007/024743 A2 | 3/2007 |
| WO | WO 2009/023457 A1 | 2/2009 |
| WO | WO 2009/045894 A1 | 4/2009 |
| WO | WO 2010/124018 A1 | 10/2010 |

OTHER PUBLICATIONS

European Extended Search Report for EP 11851794 dated Feb. 2, 2015.
Knight et al, "The Immunogenicity of the 7E3 Murine Monocolona FAB Antibody Fragment Variable Region is Dramatically Reducedin Humans by substitution of Human for Murine Constact Regions", Molecular Immunology, vol. 32; pp. 1271-1281, (1995).
Nasu et al. 1980, "Characterization of anti-F(ab')² antibodies in SLE patients evidence for cross-reacting autoanti-idiotypic antibodies", Clinical Immunology and Immunopathology, vol. 25., No. 1, pp. 80-90 (1982).
Persselin and Stevens, "Anti-Fab antibodies in humans: Predominance of minor immunoglobulin G subclasses in rheumatoid arthritis", J. Clinical Investigation, vol. 76, pp. 723-730, (1985).
Terness et al., "The Natural Human IgG Anti-F(ab')$_2$ Antibody Recognizes a Conformational IgG1 Hinge Epitope$^1$", Journal of Immunology 154, pp. 6446-6452 (1995).
Fick et al., "IgG Proteolytic Activity of *Pseudomonas aeruginosa* in Cystic Fibrosis", Journal of Infectious Diseases, vol. 151, No. 4, pp. 589-598 (1985).
Goldberg et al., "F(ab')$_2$-like Fragments from Severely Burned Patients provide a New Serum Immunoglobin Component", Nature, vol. 228, pp. 160-162 (1970).
Marion Waller, "IgG Hydrolysis in Abscesses, I. A Study of the IgG in Human Abscess Fluid", Immunology, vol. 26, pp. 725-733 (1974).
Eckle et al., "Detection of Granulocyte Elastase Specific IgG Split Products in Rheumatoid Synovial Fluid", Avd. Exp. Med. Biol., 204: pp. 531-534 (1988).
Gearing Ajh et al., "Selective cleavage of human IgG by the matrix metalloproteinases, atrilysin and stromelysin", Immunology Letters, vol. 81, No. 1, pp. 41-48 (2002).

(Continued)

*Primary Examiner* — Sean Aeder
*Assistant Examiner* — Julie Wu
(74) *Attorney, Agent, or Firm* — Kenneth J. Dow

(57) ABSTRACT

The present invention relates to modified Fc-containing molecules including modified antibodies characterized by increased resistance to host and pathogen-derived proteases, ability to interact with FcγR receptors except with FcγRI, and lack of induction of IL-10 secretion by macrophages, and methods of using and making them.

12 Claims, 30 Drawing Sheets

(56) References Cited

OTHER PUBLICATIONS

Vincents et al., "Enzymatic characterization of the streptococcal endopeptidase, IdeS, reveals that it is a cysteine protease with strict specificity for IgG cleavage due to exosite binding", Biochemistry 43: pp. 15540-15549 (2004).
Barrett, et al, Handbook of Proteolytic Enzymes, vol. 1, pp. 43-48; Elsevier, Amsterdam (2004).
Barrett, et al, Handbook of Proteolytic Enzymes, vol. 1, pp. 472-480; Elsevier, Amsterdam (2004).
Barrett, et al, Handbook of Proteolytic Enzymes, vol. 1, pp. 480-483; Amsterdam (2004).
Barrett, et al, Handbook of Proteolytic Enzymes, vol. 1, pp. 512-523; Elsevier, Amsterdam (2004).
Barrett, et al, Handbook of Proteolytic Enzymes, vol. 1, pp. 532-537; Elsevier, Amsterdam (2004).
Barrett, et al, Handbook of Proteolytic Enzymes, vol. 1, pp. 540-544; Elsevier, Amsterdam (2004).
Barrett et al., Handbook of Proteolytic Enzymes, vol. 2, pp. 1079-1083; Elsevier, Amsterdam (2004).
Barrett et al., Handbook of Proteolytic Enzymes, vol. 2, pp. 1104-1107; Elsevier, Amsterdam (2004).
Barrett et al., Handbook of Proteolytic Enzymes, vol. 2, pp. 1448-1451; Elsevier, Amsterdam (2004).
Barrett et al., Handbook of Proteolytic Enzymes, vol. 2, pp. 1489-1492; Elsevier, Amsterdam (2004).
Barrett et al., Handbook of Proteolytic Enzymes, vol. 2, pp. 1504-1507; Elsevier, Amsterdam (2004).
Barrett et al., Handbook of Proteolytic Enzymes, vol. 2, pp. 1517-1523; Elsevier, Amsterdam (2004).
Barrett et al., Handbook of Proteolytic Enzymes, vol. 2, pp. 1524-1525; Elsevier, Amsterdam (2004).
Barrett et al., Handbook of Proteolytic Enzymes, vol. 2, pp. 1526-1530; Elsevier, Amsterdam (2004).
Barrett et al., Handbook of Proteolytic Enzymes, vol. 2, pp. 1531-1534; Elsevier, Amsterdam (2004).
Barrett et al., Handbook of Proteolytic Enzymes, vol. 2, pp. 1577-1579; Elsevier, Amsterdam (2004).
Barrett et al., Handbook of Proteolytic Enzymes, vol. 2, pp. 1692-1695, Elsevier, Amsterdam (2004).
Powers, JC., "Proteolytic Enzymes and Disease Treatment", Modification of Proteins: Food, Nutritional, and Pharmacological Aspects, Advances in Chemistry Series 198 ACS, Washington, D.C. pp. 347-367, Feeney and Whitaker (eds.) (1982).
Tchetverikov et al., "MMP Profile in paired serum and synovial fluid samples of patents with rheumatoid arthritis", Ann. Rheum. Dis, vol. 63, pp. 881-883, (2004).
Sun et al., "Plasminogen is a critical host pathogenicity factor for group A streptococcal infection", Science, vol. 305, pp. 1283-1286 (2004).
Welschof et al., "The Antigen Binding Domain of Non-idiotypic Human anti-F(ab')$_2$Autoantibodies: Study of their interation with IgG Hinge Region Epitopes", Human Immunology, vol. 60, No. 4, pp. 282-290 (1999).
Welschof et al., "The antigen-binding domain of a human IgG-anti F9ab')$^2$ autoantibody", Proc. Nat. Acad. Sci (USA), vol. 94, pp. 1902-1907 (1997).
Yano et al., "Natural antibodies against the immunoglobulin F(ab')$^2$ from the circulation", Eur. J. Immunol. vol. 25, No. 11, pp. 3128-3133 (1995).
Ryan et al., "Proteolysis of purified IgGs by human and bacterial enzymes in vitro and the detection of specific proteolytic fragments of endogenous IgG in rheumatoid synovial fluid", Molecular Immunology, vol. 45, pp. 1837-1846 (2008).
Yamaguchi et al., "Proteolytic fragmentation with high specificity of mouse immunoglobulin G", Journal of Immunological Methods, vol. 181, pp. 259-267 (1995).
Süsal et al., "Induction of Anti-F(ab)$_{2y}$ Antibodies by Buffy Coat Transfusions and Their Effect in Kidney Transplantation", Transplantation Proceedings, vol. 22, No. 4, pp. 1893-1894 (1990).

Brezski et al., "Tumor-associated and microbial proteases compromise host IgG effector functions by a single cleavage proximal to the hinge", PNAS, pp. 1-6 (2009).
Fumia et al., "Human F(ab)$_2$-containing immune complexes together with anti-hinge natural antibodies stimulate complement amplification in vitro and in vivo", Molecular Immunology, vol. 45, pp. 2951-2961 (2008).
Terness et al., "A Natural IgA-Anti-F(ab)$_{2y}$ Autoantibody Occurring in Healthy Individuals and Kidney Graft Recipients Recognizes an IgG1 Hinge Region Epitope", The American Association of Immunologists, pp. 4251-4257 (1996).
Schmidt et al., "A synthetic peptide approach for elucidating the points of natural auto-antibody reactivity to proteolytic fragments of human IgG", Biopolymers, New York, NY, vol. 88, No. 4, p. 556, XP09142664 (Jan. 1, 2007).
Brezski et al., "Cleavage of IgGs by proteases associated with invasive diseases: an evasion tactic against host immunity?", Mabs., vol. 2, No. 3, pp. 212-220 May 2010.
Brezski et al., Human anti-IgG1 hinge autoantibodies reconstitute the effector functions of proteoltically inactivated IgGs., Proc. Natl. Acad. Sci. USA, vol. 106, No. 42, pp. 17864-17869 Oct. 2009.
Brezski et al., "Human antiIgG1 hinge autoantibodies reconstitute the effector functions of proteolytically inactivated IgGs.", Journal of Immunology, vol. 181, No. 5, pp. 3183-3192 Sep. 2008.
Nandakumar et al., "Blocking of experimental arthritis by cleavage of IgG antibodies in vivo", Arthritis Rheum., vol. 56, No. 10, pp. 3253-3260, Oct. 2007.
Eriksson et al., "Cleavage of antigen-bound immunoglobulin G by SpeB contributes to streptococcal persistence in opsonizing blood", Infect Immun., vol. 71, No. 1, pp. 211-217, Jan. 2003.
Bianchi et al., "Universal influenza B vaccine based on the maturational cleavage site of the hemagglutinin precursor", Journal Virol., vol. 79, No. 12, pp. 7380-7388, Jun. 2005.
Hezareh et al., "Effector Function Activities of a Panel of Mutants of a Broadly Neutralizing Antibody against Human Immunodeficiency Virus Type 1", Journal of Virology, vol. 75, No. 24, pp. 12161-12168 (2001).
Shields et al.. "High Resolution Mapping of the Binding Site on Human !gG1 for RCyRI, RcyRII, FcyRIII, and FcRn and Design of IgG1 Variants with Improved Binding to the FcyR", Journal of Biological Chemistry, vol. 276, No. 9, pp. 6591-6604 (2001).
Labrijn et al., "When binding is enough: non-activating antibody formats", Current Opinion Immunology, vol. 20: pp. 479-485 (2008).
Sutterwala et al., "Reversal of Proinflammatory Responses by Ligating the Macrophage Fcy Receptor Type I", Journal of Experimental Medicine, vol. 188:1, pp. 217-222 (1998).
Pander et al., "Activation of Tumor-Promoting Type 2 Macrophages by EGFR-Tageting Antibody Cetuximab", Clinical Cancer Research, vol. 17: pp. 5668-5673 (2011).
Lazar, "Engineered antibody Fc variants with enhanced effector function", Proc Natl Acad Sci USA, vol. 103: pp. 4005-4010 (2006).
Idusogie, "Engineered Antibodies with Increased Activity to Recruit Complement", Journal Immunology, vol. 166: pp. 2571-2575 (2001).
Stavenhagen, "Fc Optimization of Therapeutic Antibodies enhances Their Ability to Kill Tumor Cells in vitro and Controls Tumor Expansion in vivo via Low-Affinity Activating Fcy Receptors", Cancer Res vol. 67(18): pp. 8882-8890 (2007).
Moore, et al., "Engineered Fc variant antibodies with enhanced ability to receuit complement and mediate effector functions" mAbs 2(2): pp. 181-189 (2010).
Armour et al., "Recombinant human IgG molecules lacing Fcy receptor I binding and monocyte triggering activities", European Journal of Immunology, 29: pp. 2613-2624 (1999).
Brezski et al., "The in vitro resistance of IgG2 to proteolytic attack concurs with a comparative paucity of autoantibodies against peptide analogs of the IgG2 hinge" Monoclonal Antibodies 3: pp. 558-567 (2011).
Patel et al.,"An improved assay for antibody dependent cellular cytotoxicity based on time resolved fluorometry", 1995 Journal of Immunological Methods 184:29.

(56) References Cited

OTHER PUBLICATIONS

Clynes et al., "Fc receptors are required in passive and active immunity to melanoma", 1998, Proceedings of the National Academy of Sciences, USA 95:652-656.
Cunningham et al., "The Covalent Structure of a Human γG-Immunoglobulin. VII. Amino Acid Sequence of a Heavy-Chain Cyanogen Bromide Fragments $H_1$-$H_4$", 1970 Biochemistry 9:3161-70.
Roux et al., "Comparisons of the Ability of Human IgG3 Hinge Mutatns, IgM, IgE, and IgA2, to Form Small Immune Complexes: A Role for Flexibility and Geometry", 1998 Journal of Immunology 161:4083.
Wright and Morrison, "Effect of glycosylation on antibody function: implications for genetic engineering", 1997 Trends Biotech 15:26-32.
Lifely et al., "Glycosylation and biological activity of CAMPATH-1H expressed in different cell lines and grown under different culture conditions", 1995 Glycobiology 5:813-22.
Jefferis et al., "IgG-Fc-mediated effector functions: molecular definition of interaction sites for effector ligands and the role of glycosylation", 1998 Immunological Reviews 163:59-76.
Presta, Leonard, "Antibody engineering for therapeutics", 2003. Current Opinion in Structural Biology 13:519-25.
Shields et al., "Lack of Fucose on Human IgG1 N-Linked Oligosaccharide Improves Binding to Human FcγRIII and Antibody-dependent Cellular Toxicity", 2002. Journal of Biological Chemistry 277:26733-40.
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphona" 2004. Cancer Res 64:2127-33.
Remington: The Science and Practice of Pharmacy, $21^{st}$Edition, Troy, D.B. ed., Lipincott Williams and Wilkins, Philadelphia, PA 2006, Part 5, Pharmaceutical Manufacturing pp. 958-9894.
Shinkawa et al., "The Absence of Fucose but Not the Presence of Galactose or Bisecting N-Acetylglyocosaime of Human IgG1 Complex-type Oligosaccharides Shows the Critical Role of Enhancing Antibody-dependent Cellular Cytotoxicity", 2003 Journal of Biological Chemistry 278:3466-73.
Smith, G.P., "Filamentous Fusion Phage: Novel Expression Vectors That Display Cloned Antigens on the Virion Surface", 1985. Science 228: 1315-1317.
Hoogenboom, et al., "Natural and designer binding sites made by phage display technology" 2000, Immunology Today 21(8) 371-8.
Kretzschmar and Von Ruden, "Antiody discovery:phage display" 2000, Current Opinion in Biotechnology 13:598-602.
Mattheakis et al., "An in vitro polysome display system for identifying ligands from very large peptide libraries", 1994 Proc. Natl. Acad. Sci. USA 91:9022.
Boder et al., "Yeast surface display for screening combinatorial polypeptide libraries", 1997 Nature Biotechnology 15:553-7.
Chen and Georgiou, "Cell-Surface Display of Heterologous Proteins: From High-throughput Screening to Environmental Applications", 2002 Biotechnol Bioeng 79:496-503.
Halstead et al., "Intrinsic antibody-dependent enhancement of microbial infection in macrophages:disease regulation by immune complexes" Lancet Infect Dis 10:712-22, 2010.
Asai et. al, "Pathogenic Role of Macrophages in Intradermal Infection of Methicillin-Resis *Staphylococcus aureus* in Thermally Injured Mice", Infection and Immunity 78(10):4311-19 2010.

Folkman and Cotran, "Relation of Vascular Proliferation to Tumor Growth" 1976 Int. Rev. Exp. Pathol. 16, 207-48.
Koch et al., "Stimulation of Neovasculariation by Human Rheumatoid Synovial Tissue Macrophages", 1986, Arthritis and Rheumatism, 29:471-79.
Stupack et al., "A role for angiogenesis in rheumatoid arthritis" 1999 Brazilian Journal of Medical and Biological Research, 32:578-81.
Koch,Alisa, "Angiogenesis", 1998 Arthritis and Rheumatism, 41:951-62.
Folkman,Judah, "Angiogenesis in Psoriasis:Therapeutic Implications", 1972 Journal of Investigative Dermatology 59:40-8.
Eliceiri et al., "The role of αv integrins during angiogenesis:inhights into potential mechanisms of action nad clinical development" 1999 Journal of Clinical Investigation 103:1227-30.
Friedlander et al., "Definition of Two Angiogenic Pathways by Distinct $α_v$ Integrins" 1995 Science 270:1500-2.
Scallon et al., "Higher levels of sialylated Fc glycans in immunoglobulin G molecules can adversely impact functionality", Moleclar Immunology 44:1524-1534 2007.
Von Pawel-Rammingen et al., "IdeS, a novel streptococcal cysteine proteinase with unique specificity for immunoglobulin G", European Molecular biology Organization vol. 21:1607-1615 2002.
Strohl et al., "Optimization of Fc-mediated effector functions of monoclonal antibodies", *Current Opinion in Biotechnology*, vol. 20, No. 6, pp. 685-691, Dec. 1, 2009.
Kinder et al., "Engineered Protease-resistant Antibodies with Selectrable Cell-killing Functions", *Journal of Biological Chemistry*, vol. 288, No. 43, pp. 30843-30854, Oct. 25, 2013.
Salfeld Jochen, "Isotype selection in antibody engineering", 2007 Nature Biotechnology 25:1369-72.
Bibeau et al., "Impact of FcγRIIa-FcγRIIIa Polymorphisms and KRAS Mutations on the Clinical Outcome of Patients with Metastatic Colorectal Cancer Treated with Cetuximab Plus Ironotecan", 2009 Journal of Clinical Oncology 27:1122-9.
Biswas and Mantovani, "Macrophage plasticity and interaction with lymphocyte subsets: cancer as a paradigm", 2010 Nature Immunology, vol. 11 No. 10:889-96.
Cartron et al., "Therapeutic activity of humanized anti-DC20 monoclonal antibody and polymorphism in IgG Fc receptor FcγRIIIa gene" 2002 Blood 99:754-8.
Musolino et al., "Immunoglobulin G Fragment C Receptor Polymorphisms and Clinical Efficacy of Trastuzumab-Based Therapy in Patients with HER-2/neu-Positive Metastatic Breast Cander", 2008 Journal of Clinical Oncology 26:1789-96.
Mosser and Zhang, "Interleukin-10:new perspectives on an old cytokine", 2008 Immunological Review 226:205-18.
Ikeda et. al., "The roles of JFNγ in protection against tumor development and cancer immunoediting", 2002 Cytokine Growth Factor Rev 13:95-109.
Cassatella et al.,"FcγR(CD16) Interaction with Ligand Induces Ca2+ Mobilization and Phosphoinositide turnover in Human Natural Killer Cells", 1989 Journal of Exp Med 169:549-67.
Parihar et al., "IL-12 enhances the natural killer cell cytokine response to Ab-coated tumor cells", 2002 Journal of Clinical Investigation 110:983-92.
Bruggemann et al., "Comparison of the effector Functions of Human Immunoglobulins Using a Matched Set of Chimeric Antibodies" 1987 J Exp Med 166:1351.
Wilkinson et al., "Antibody-dependent cell-mediated cytotoxicity: a flow cytometry-based assay using fluorophores", 2001 Journal of Immunological Methods 258:183-191.

\* cited by examiner

Upper Hinge    Core    Lower Hinge/CH2 Region
(Fab Region)    Hinge    (F(ab')$_2$ Region)

S(219)-C-D-K$_1$T$_2$H$_3$T-C-P-P-C-P-A-P$_4$E$_5$L$_6$L-G$_7$G-P-S(239)

1 Plasmin
2 Human Neutrophil Elastase (HNE)
3 Papain
4 MMP-3, MMP-12
5 Glutamyl endopeptidase I (GluV8), Cathepsin G
6 Pepsin, MMP-7
7 IdeS

*Fig. 2*

```
              EU 214                                                     263
hIgG1 wild-type    KVEPKSCDKTHTCPPCPAPELLGGPSVFLFPPKPKDTLMISRTPEVTCVV  SEQ ID
NO: 1 hIgG2 wild-type    T--R-C-VE///-------PVA/---------------------------  SEQ ID
NO: 2 hIgG1 2hDE         -------------------PVA/--D------------------------  SEQ ID
NO: 8 hIgG1 2hAA         -------------------PVA/---------------------------  SEQ ID
NO: 9

264                                                        313
hIgG1 wild-type    VDVSHEDPEVKFNWYVDGVEVHNAKTKPREEQYNSTYRVVSVLTVLHQDW
hIgG2 wild-type    ----------Q---------------------F---F--------V----
hIgG1 2hDE         --------------------------------------------------
hIgG1 2hAA         --------------------------------------------------

314                                                        363
hIgG1 wild-type    LNGKEYKCKVSNKALPAPIEKTISKAKGQPREPQVYTLPPSRDELTKNQV
hIgG2 wild-type    --------------G-----------T----------------E-M----
hIgG1 2hDE         ------------------E-------------------------------
hIgG1 2hAA         ------------------AA------------------------------

364                                                        413
hIgG1 wild-type    SLTCLVKGFYPSDIAVEWESNGQPENNYKTTPPVLDSDGSFFLYSKLTVD
hIgG2 wild-type    ---------------S--------------------M-------------
hIgG1 2hDE         ---------------A----------------------------------
hIgG1 2hAA         ---------------A----------------------------------

414                       447
hIgG1 wild-type    KSRWQQGNVFSCSVMHEALHNHYTQKSLSLSPGK
hIgG2 wild-type    ----------------------------------
hIgG1 2hDE         ----------------------------------
hIgG1 2hAA         ----------------------------------

- Denotes that the sequences are the same
           / Denotes a deletion
```

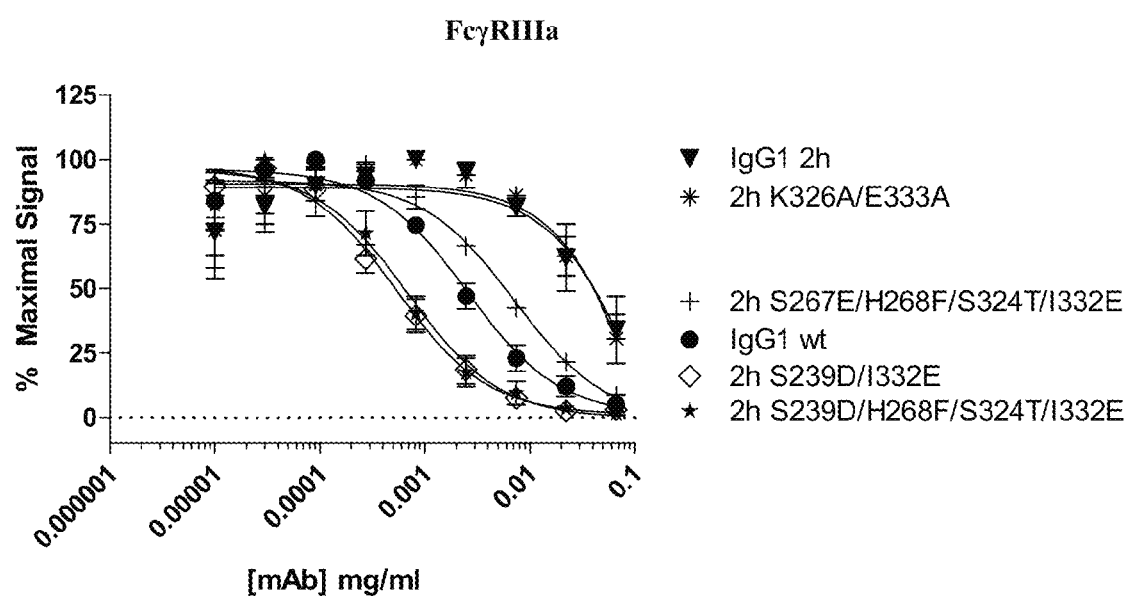

Fig. 13

| Construct | Variant | FcγRI IC₅₀ (mg/ml) | FcγRI fold change | FcγRIIa* IC₅₀ (mg/ml) | FcγRIIa* fold change | FcγRIIb IC₅₀ (mg/ml) | FcγRIIb fold change | FcγRIIIa** IC₅₀ (mg/ml) | FcγRIIIa** fold change |
|---|---|---|---|---|---|---|---|---|---|
| 1 | IgG1 wt | 0.000397 | 1 | 0.072165 | 1 | 0.166400 | 1 | 0.003222 | 1 |
| 2 | IgG2 wt | >0.1 | <0.004 | 0.254000 | 0.28 | >0.2 | <0.83 | >0.2 | <0.02 |
| 18 | IgG4 wt | 0.000566 | 0.7 | 0.268900 | 0.27 | 0.180790 | 0.92 | >0.2 | <0.02 |
| 4 | 2h | >0.1 | <0.004 | >0.6 | <0.12 | >0.2 | <0.83 | >0.2 | <0.02 |
| 5 | 2h S239D/I332E | 0.023090 | 0.02 | 0.057030 | 1.27 | 0.154350 | 1.08 | 0.001762 | 1.83 |
| 3 | 2h complete | >0.1 | <0.004 | 0.169100 | 0.43 | >0.2 | <0.83 | >0.2 | <0.02 |
| 12 | 2h G237A/S239D/I332E | >0.1 | <0.004 | >0.6 | <0.12 | 0.154850 | 1.07 | 0.001384 | 2.33 |
| 8 | 2h H268F/S324T/I332E | >0.1 | <0.004 | 0.097465 | 0.74 | 0.148550 | 1.12 | 0.018000 | 0.18 |
| 11 | 2h K326A/E333A | >0.1 | <0.004 | >0.6 | <0.12 | >0.2 | <0.83 | 0.125400 | 0.03 |
| 9 | 2h S239D/H268F/S324T/I332E | 0.022020 | 0.02 | 0.047120 | 1.53 | 0.082000 | 2.03 | 0.001071 | 3.01 |
| 10 | 2h S267E/H268F/S324T/I332E | 0.063190 | 0.01 | 0.000961 | 75.1 | 0.001857 | 89.6 | 0.009410 | 0.34 |
| 14 | IgG2 S239D/I332E | 0.010105 | 0.04 | 0.006979 | 10.3 | 0.018210 | 9.14 | 0.000983 | 3.28 |
| 16 | 2h S239D/K326A/E333A | >0.1 | <0.004 | 0.118635 | 0.61 | >0.2 | <0.83 | 0.003745 | 0.86 |
| 15 | 2h K326A/I332E/E333A | >0.1 | <0.004 | 0.164500 | 0.44 | 0.173900 | 0.96 | 0.004331 | 0.74 |
| 17 | 2h S267E/I332E | >0.1 | <0.004 | 0.002107 | 34.3 | 0.003297 | 50.5 | 0.009307 | 0.35 |

*FcγRIIa polymorphism was R131
**FcγRIIIa polymorphism was V158

Fig. 14

| Construct | Variant | 24 hour ADCP | Macroph. IL-10 release | PBMC IFNγ release | CDC | ADCC | FcγRI* | FcγRIIa* | FcγRIIb* | FcγRIIIa* |
|---|---|---|---|---|---|---|---|---|---|---|
| 1 | IgG1 wt | +++++ | ++++ | +++++ | +++++ | +++++ | 1 | 1 | 1 | 1 |
| 2 | IgG2 wt | ++ | - | - | - | - | <0.004 | 0.28 | <0.83 | <0.02 |
| 3 | 2hc | ++ | - | - | n.d. | + | <0.004 | 0.43 | <0.83 | <0.02 |
| 4 | 2h | ++ | - | - | - | + | <0.004 | <0.12 | <0.83 | <0.02 |
| 5 | 2h S239D/I332E | +++++ | + | + | +++++ | ++++++ | 0.02 | 1.27 | 1.08 | 1.83 |
| 8 | 2h H268F/S324T/I332E | +++ | - | +++ | - | +++++++ | <0.004 | 0.74 | 1.12 | 0.18 |
| 9 | 2h S239D/H268F/S324T/I332E | +++++ | + | +++++ | - | +++++ | 0.02 | 1.53 | 2.03 | 3.01 |
| 10 | 2h S267E/H268F/S324T/I332E | ++++ | + | + | +++++ | + | 0.01 | 75.1 | 89.6 | 0.34 |
| 11 | 2h K326A/E333A | ++ | - | + | +++++ | +++ | <0.004 | <0.12 | <0.83 | 0.03 |
| 12 | 2h G237A/S239D/I332E | ++++ | + | +++++ | n.d. | +++++++ | <0.004 | <0.12 | 1.07 | 2.33 |
| 14 | IgG2 S239D/I332E | ++++ | + | ++++ | n.d. | +++++++ | 0.04 | 10.3 | 9.14 | 3.28 |
| 15 | 2h K326A/I332E/E333A | +++ | - | +++++ | ++++ | +++++++ | <0.004 | 0.44 | 0.96 | 0.74 |
| 16 | 2h S239D/K326A/E333A | +++ | - | ++++ | ++++ | +++++ | <0.004 | 0.61 | <0.83 | 0.86 |
| 17 | 2h S267E/I332E | ++++ | - | + | +++ | + | <0.004 | 0.44 | 50.5 | 0.35 |
| 18 | IgG4 wt | ++++ | +++++ | - | - | - | 0.7 | 0.27 | 0.92 | <0.02 |

*fold change calculated as described in the specification

ACTIVE PROTEASE-RESISTANT ANTIBODY FC MUTANTS

PRIOR APPLICATION

This application is a Continuation of U.S. application Ser. No. 13/555,334 filed Jul. 23, 2012, currently allowed, which is a Continuation-in-Part of International application number PCT/US11/065174, filed Dec. 15, 2011, which claims the benefit of U.S. Provisional Application No. 61/540,882 filed Sep. 29, 2011, and U.S. Provisional Application No. 61/426,619, filed Dec. 23, 2010, which are entirely incorporated herein by reference.

FIELD OF THE INVENTION

The present invention relates to modified Fc-containing molecules including modified antibodies which are characterized by their increased resistance to host and pathogen-derived proteases, their ability to interact with FcγR receptors except with FcγRI, and their lack of induced IL-10 secretion by macrophages, and methods of using and making them.

BACKGROUND OF THE INVENTION

The IgG isotype of human antibodies consists of subtypes IgG1, IgG2, IgG3, and IgG4, each containing two antigen binding arms (Fabs) connected to a single Fc domain by the hinge region. IgG1, the predominant subclass represented in therapeutic monoclonal antibodies, are considered stable molecules with long half-life in circulation of 17.6 to 56.2 days (Salfeld, 2007 Nat Biotechnol 25:1369-72). However, IgG1 is susceptible to proteolysis in the hinge region by a number of physiologically-relevant proteases associated with invasive cancer (e.g. matrix metalloproteinases), inflammatory autoimmune diseases (e.g. MMP-3 and MMP-12 secretion in inflammatory bowel disease and rheumatoid arthritis) and pathological microorganisms. Cleavage above the disulfide bonds (core hinge) between the heavy chains liberates the monovalent Fab and bilateral cleavage below the disulfide bonds liberates a bivalent structure, the F(ab')$_2$ fragment. Several metalloproteinases and two bacterial enzymes, glutamyl endopeptidase V8 of *Staphylococcus aureus* (GluV8) and Immunoglobulin degrading enzyme of *Streptococcus pyogenes* (IdeS), act on IgG1 in the lower hinge (below the disulfide bonds (FIG. 1) and ultimately produce a F(ab')$_2$ and an Fc fragment (Ryan et al., 2008 Mol Immunol 45:1837-46). A single proteolytic cleavage in one of the heavy chain polypeptides of an IgG1 causes a loss of the IgG1's ability to bind FcγRs and drive Fc-mediated effector functions (Brerski et al., 2009 Proc Natl Acad Sci USA 106:17864-9). Both single and multiple cleavages of therapeutic monoclonal antibodies may lead to species that bind target but have lost some or all efficacy.

The antibody effector functions mediated by the Fc domain are important in the overall therapeutic effect of the antibody (mAb) (Bibeau et al., 2009 J Clin Oncol 27:1122-9; Carton et al., 2002 Blood 99:754-8; Musolino et al., 2008 J Clin Oncol 26:1789-96). The Fc domain of the antibody interacting with Fc gamma receptors (FcγR) expressed on immune cells, as well as Fc domain interactions with complement contribute to the action of several monoclonal antibodies (mAbs) directed against cell surface antigens. These interactions can lead to the elimination of the mAb targeted cell by antibody-dependent cellular cytotoxicity (ADCC), antibody-dependent cellular phagocytosis (ADCP), or complement-dependent cytotoxicity (CDC).

The Fc-dependent effector functions also include antibody-dependent cytokine release (ADCR). Some of the first Fc engineering efforts were aimed towards silencing Fc:FcγR interactions in order to abrogate unwanted cytokine release when the intent of the mAb was to suppress immune responses, as was the case with the anti-CD3 epsilon targeting muromomab-CD3 (reviewed in (Labrijn et al., 2008 Curr Opin Immunol 20:479-85).

Interactions between the Fc domain of antibodies and FcγRs can also influence the cell fate decisions of immune effector cells. Fc interactions with FcγRI on macrophages converted the macrophages from a pro-inflammatory phenotype into a regulatory phenotype (Sutterwala et al., 1998 J Exp Med 188:217-22) characterized by the secretion of the anti-inflammatory cytokine IL-10. Some of the anti-inflammatory properties attributed to IL-10 include both inhibition of antigen presentation and the expression of co-stimulatory molecules, blocking monocyte differentiation into dendritic cells (DC), inhibition of DC maturation, suppression of tumor cell killing by macrophages, and suppression of the release of pro-inflammatory cytokines such as IL-1, IL-6, IL-12, IFNγ, and TNF (reviewed in Mosser and Zhang, 2008 Immunol Rev 226:205-18). These effects diminish the ability of antigen presenting cells (APCs) to drive pro-inflammatory, Th1 immune responses. IL-10 can also sustain the ability of T regulatory cells to inhibit Th1 immune responses. It was recently suggested that monoclonal antibodies targeting tumor-associated antigens (e.g. the anti-EFGR mAb, cetuximab) can also induce macrophage IL-10 production, resulting in an anti-inflammatory, pro-tumor microenvironment and potential lack of efficacy of the anti-cancer therapeutics (Pander et al., 2011 Clin Cancer Res 17:5668-73).

Antibodies have the ability to induce the release of pro-inflammatory cytokines by interacting with FcγRs on PBMCs. IFNγ is a pro-inflammatory cytokine that can enhance macrophage tumor cell killing by increasing reactive nitrogen intermediates, augment cross-presentation, increase expression of co-stimulatory molecules and MHC I and MHC II, and drive Th1 cell differentiation. IFNγ can also directly inhibit the growth of tumor cells and virally infected cells (Ikeda et. Al., 2002 Cytokine Growth Factor Rev 13:95-109). Triggering FcγRIIIa on NK cells resulted in IFNγ production (Cassatella et al., 1989 J Exp Med 169:549-67). Opsonization of tumor cells with the human wild type IgG1 anti-HER2 mAb trastuzumab resulted in induction of IFNγ secretion from NK cells, and this secretion was influenced by the presence of IL-12 (Parihar et al., 2002 J Clin Invest 110:983-92). The ability of mAbs to induce NK cells to secrete IFNγ is considered beneficial for tumor-antigen targeting mAbs.

There is a need for protease resistant and effector-function retaining Fc antibody platforms that do not elicit IL-10 secretion by macrophages, (i.e. and thus do not promote macrophages to convert to anti-inflammatory regulator macrophages) for the treatment of cancer and infectious disease and other disease where the destruction of target cells or tissues is desired.

SUMMARY OF THE INVENTION

One aspect of the invention is an isolated modified Fc-containing molecule or a fragment thereof comprising a wild type human IgG1 Fc region of SEQ ID NO: 1 comprising a hinge, a CH2 domain and a CH3 domain, wherein the sequence of E233-L234-L235-G236 in the hinge is replaced with P233-V234-A235 with G236 deleted; the CH2 domain comprises at least one substitution selected from S239D/I332E; K326A/E333A; H268F/S324T/I332E; F243L/R292P/Y300L; S239D/H268F/S324T/I332E; S267E/H268F/S324T/I332E; K326A/I332E/E333A; S239D/K326A/E333A; S267E/I332E; and G237X/S239D/I332E where X is A, D, P, Q or S; the isolated modified Fc-domain containing molecule or fragment thereof is resistant to proteolytic degradation by a protease that cleaves the wild type human IgG1 molecule between or at residues 222-237; the isolated modified Fc-domain containing molecule or fragment thereof is capable of promoting antibody-dependent cellular phagocytosis (ADCP) measured in the presence of CD14 positive and/or CD11b positive human monocyte-derived macrophages, is capable of promoting antibody-dependent cell-mediated cytotoxicity (ADCC) measured in the presence of blood mononuclear cells, and/or is capable of promoting complement-dependent cytotoxicity (CDC) measured by cell lysis in the presence of complement; and the isolated modified Fc-containing molecule or fragment thereof induces IL-10 secretion by human monocyte-derived macrophages by about no more than three times more when compared to the IL-10 secretion by the human monocyte-derived macrophages in the absence of the isolated modified Fc-containing molecule; wherein amino acid residues are numbered according to EU numbering.

Another aspect of the invention is an isolated antibody or fragment thereof comprising a modified Fc-containing molecule comprising a wild type human IgG1 Fc region of SEQ ID NO: 1 comprising a hinge, a CH2 domain and a CH3 domain, wherein the sequence of E233-L234-L235-G236 in the hinge is replaced with P233-V234-A235 with G236 deleted; the CH2 domain comprises at least one substitution selected from S239D/I332E; K326A/E333A; H268F/S324T/I332E; F243L/R292P/Y300L; S239D/H268F/S324T/I332E; S267E/H268F/S324T/I332E; K326A/I332E/E333A; S239D/K326A/E333A; S267E/I332E; and G237X/S239D/I332E where X is A, D, P, Q or S; the isolated modified Fc-domain containing molecule or fragment thereof is resistant to proteolytic degradation by a protease that cleaves the wild type human IgG1 molecule between or at residues 222-237; the isolated modified Fc-domain containing molecule or fragment thereof is capable of promoting antibody-dependent cellular phagocytosis (ADCP) measured in the presence of CD14 positive and/or CD11b positive human monocyte-derived macrophages, is capable of promoting antibody-dependent cell-mediated cytotoxicity (ADCC) measured in the presence of blood mononuclear cells, and/or is capable of promoting complement-dependent cytotoxicity (CDC) measured by cell lysis in the presence of complement; and the isolated modified Fc-containing molecule or fragment thereof induces IL-10 secretion by human monocyte-derived macrophages by about no more than three times more when compared to the IL-10 secretion by the human monocyte-derived macrophages in the absence of the isolated modified Fc-containing molecule; wherein amino acid residues are numbered according to EU numbering.

Another aspect of the invention is a pharmaceutical composition comprising the isolated modified Fc-domain containing molecule of the invention.

Another aspect of the invention is a method for treating a disease characterized by unwanted proliferation or migration of cells, comprising administering a therapeutically effective amount of a pharmaceutical composition of the invention to a patient in need thereof for a time sufficient to treat the disease characterized by unwanted proliferation or migration of cells.

Another aspect of the invention is a method for treating an infection, comprising administering a therapeutically effective amount of a pharmaceutical composition of the invention to a patient in need thereof for a time sufficient to treat the infection.

BRIEF DESCRIPTION OF THE DRAWING

FIG. 2 shows an alignment of the amino acid sequences of portions of the constant regions of wild type human IgG1 (SEQ ID NO: 1) and IgG2 (SEQ ID NO: 2) aligned with new constructs 2h S239D/I332E (SEQ ID NO: 8) and 2h E333A/K334A (SEQ ID NO: 9) showing the corresponding EU numbering for each residue; where the hinge region of both IgG1 and IgG2 both comprise the cysteine residues at EU residue 226 and 229 as do the new constructs.

FIG. 5A-G show an FcγR-binding results from ALPHASCREEN® analysis for groups of protease-resistant mAb constructs: FcγRI (A), FcγRIIa (B and C), FcγRIIb (D and E), and FcγRIIIa (F and G) where the reduction from % Maximal Signal represents the ability of an unlabeled construct to compete with biotinylated IgG1 from binding (n=2).

FIG. 13 shows binding of protease-resistant mAb constructs to various FcγR receptors as $IC_{50}$ values and fold changes of $IC_{50}$ values when compared to the wt IgG1.

FIG. 14 shows a summary of ADCC, 24 hour ADCP, macrophage IL-10 secretion, PBMC IFNγ release, and FcγR-binding. The FcγR-binding is depicted as the fold change calculated by IC50 [IgG1 wt]/IC50 [variant]. n.d.=not determined

Figure 1:
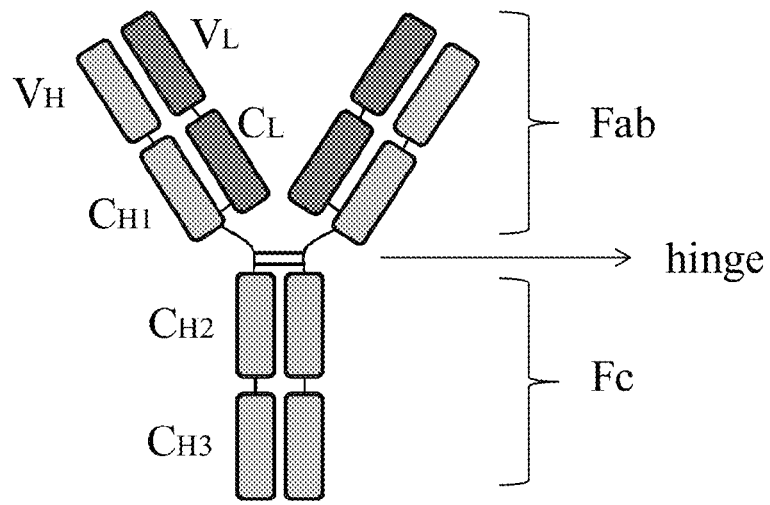
FIG. 1 is a depiction of a human IgG1 antibody accompanied by the amino acid sequence found in the hinge region, a region critical for interaction with FcγRs and complement, and mapped protease cleavage points.

| BRIEF DESCRIPTION OF THE SEQUENCE LISTING | |
|---|---|
| SEQ ID NO: | Description |
| 1 | IgG1- Fc; Human Ig gamma class, subclass, hinge, CH2 and CH3 domains |
| 2 | IgG2 - Fc; Human Ig gamma class, subclass 2 hinge, CH2 and CH3 domains |
| 3 | IgG1 hinge region, EU 214-236 |
| 4 | IgG2 hinge region (2 hc), EU 214-235 |
| 5 | IgG hybrid hinge region (2h), IgG2 EU 233-235 |
| 6 | 2hc (EU 214-447) |
| 7 | 2h (EU 214-447) |
| 8 | 2h S239D/I332E |
| 9 | 2h E333A/K334A |
| 10 | 2h F243L/R292P/Y300L |
| 11 | 2h H268F/S324T/I332E |
| 12 | 2h S239D/H268F/S324T/I332E |
| 13 | 2h S267E/H268F/S324T/I332E |
| 14 | 2h K326A/E333A |
| 15 | 2h G237X/S239D/I332E where X is A, D, P, Q or S |
| 16 | 2hc S239D/I332E |
| 17 | IgG2 S239D/I332E |
| 18 | 2h K326A/I332E/E333A |
| 19 | 2h S239D/K326A/E333A |
| 20 | 2h S267E/I332E |
| 21 | 2h S239D/I332E cDNA |
| 22 | 2h S239D/K326A/E333A cDNA |

ABBREVIATIONS

ADCC=antibody-dependent cellular cytotoxicity; ADCP, antibody-dependent cellular phagocytosis; CDC=complement-dependent cytotoxicity; FDCR=Fc-dependent cytokine release; FcγR or FcgammaR=Fc gamma receptor; GluV8=glutamyl endopeptidase V8 of *Staphylococcus aureus*; IdeS=Immunoglobulin degrading enzyme of *Streptococcus pyogenes* IgG=immunoglobulin G; ITAM=immunoreceptor tyrosine-based activating motif; ITIM=immunoreceptor tyrosine-based inhibitory motif; Mab=monoclonal antibody; MMP=matrix metalloproteinase; the term protease is equivalent to proteinase and are used interchangeably; PR=protease resistant.

DETAILED DESCRIPTION OF THE INVENTION

"Antibody-dependent cellular cytotoxicity," "Antibody-dependent cell-mediated cytotoxicity" or ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Ligand specific high-affinity IgG antibodies directed to the surface of target cells stimulate the cytotoxic cells and are absolutely required for such killing. Lysis of the target cell is extracellular, requires direct cell-to-cell contact, and does not involve complement.

The ability of any particular antibody to mediate lysis of the target cell by ADCC can be assayed. To assess ADCC activity, an antibody of interest is added to target cells displaying the target ligand in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al., 1987 J Exp Med 166:1351; Wilkinson et al., 2001 J Immunol Methods 258:183; Patel et al., 1995 J Immunol Methods 184:29 (each of which is incorporated by reference). Alternatively, or additionally, ADCC activity of the antibody of interest may be assessed in vivo, e.g., in an animal model such as that disclosed in Clynes et al., 1998, PNAS USA 95:652, the contents of which is incorporated by reference in its entirety. Where the effector cell acts largely through phagocytosis, the process can be described as Antibody Dependent Cellular Phagocytosis (ADCP).

"Complement-directed cytotoxicity" or CDC refers to the form of cytotoxicity in which the complement cascade is activated by the complement component C1q binding to antibody Fc.

The term "effector functions" include those interactions of Fc with Fc gamma receptors (FcγR) expressed on immune cells, as well as Fc domain interactions with complement leading to elimination of the antigen-expressing cell by lytic processes or phagocytosis by effector cells and complement components.

The terms "Fc," "Fc-containing protein" or "Fc-containing molecule" as used herein refer to a monomeric, dimeric or heterodimeric protein having at least an immunoglobulin CH2 and CH3 domain. The CH2 and CH3 domains can form at least a part of the dimeric region of the protein/molecule (e.g., antibody).

The term "antibody" as used herein is a specific form of an Fc-containing protein comprising at least one ligand binding domain which contains, or retains substantial homology to, at least one of a heavy or light chain antibody variable domain of at least one species of animal antibody.

Wild type human IgG subclass constant sequences are cataloged in the UniProt database available on-line as P01857 (IgG1), P01859 (IgG2), P01860 (IgG3), and P01861 (IgG4). As used herein, "wild type human IgG1 Fc region" refers to a human IgG Fc region that comprises the amino acid sequence of SEQ ID NO: 1 or a fragment thereof, which is from residue K214 to residue K447 of the human IgG heavy chain, according to the EU numbering of Kabat Amino acids in the constant region are numbered by alignment with the human IgG1 antibody, EU (see Cunningham et al., 1970 Biochemistry 9:3161-70). That is, the heavy and light chains of an antibody are aligned with the heavy and light chains of EU to maximize amino acid sequence identity and each amino acid in the antibody is assigned the same number as the corresponding amino acid in EU. The EU numbering system is conventionally used in the art (see generally, Kabat et al, Sequences of Protein of Immunological Interest, NIH Publication No. 91-3242, US Department of Health and Human Services (1991)). According to the convention, the alignment between the wild type IgG2 constant region and that of EU results in an empty amino acid at positions 221-223 and 236 (FIG. 2, SEQ ID NO: 2).

The constant domain sequences of the mammalian IgG heavy chain are designated in sequence as CH1-hinge-CH2-

CH3. The "hinge", "hinge region" or "hinge domain" of an IgG is generally defined as including Glu216 and terminating at Pro230 of human IgG1 according to the Kabat system but functionally, the flexible portion of the chain may be considered to include additional residues termed the upper and lower hinge regions, such as from Glu216 to Gly237 (Roux et al., 1998 J Immunol 161:4083) and the lower hinge has been referred to as residues 233 to 239 of the Fc region where FcgammaR binding was generally attributed. Hinge regions of other IgG isotypes may be aligned with the IgG1 sequence by placing the first and last cysteine residues forming inter-heavy chain S—S binds. Although boundaries may vary slightly, as numbered according to the Kabat system, the CH1 domain is adjacent to the VH domain and amino terminal to the hinge region of an immunoglobulin heavy chain molecule and includes the first (most amino terminal) constant region domain of an immunoglobulin heavy chain, e.g., from about EU positions 118-215. The Fc domain extends from amino acid 231 to amino acid 447; the CH2 domain is from about Ala231 to Lys340 or Gly341 and the CH3 from about Gly341 or Gln342 to Lys447. The residues of the IgG heavy chain constant region of the CH1 region terminate at Lys.

The term "protease resistant" refers to the ability of a molecule comprised of peptide bonds, to resist hydrolytic cleavage of one or more of its peptide bonds in the presence of a proteolytic enzyme. The resistance to proteolytic enzymes is a relative property and is compared to a molecule which is less able to withstand hydrolytic cleavage of one or more of its peptide bonds over a specified time period and under specified conditions, including the pH and or temperature at which the cleavage resistance is tested. One result of proteolytic cleavage indicative that cleavage has occurred is the generation of smaller fragments (lower molecular weight) as compared to the molecular weight of the intact, non-cleaved parent molecule. A modified Fc-containing molecule or a fragment thereof comprising a hinge, a CH2 domain and a CH3 domain is "protease resistant" or "resistant to proteolysis" or has "increased resistance to proteolysis" when more than about 60%, 65%, 70%, 75%, 80%, 85%, 90%, 95%, 96%, 97%, 98%, 99% or 100% of a full length immunoglobulin that incorporates a modified Fc of the invention remains intact for 24 hours when digested by matrix metalloprotease-3 (MMP-3), matrix metalloprotease-12 (MMP-12), glutamyl endopeptidase V8 of *Staphylococcus aureus* (GluV8), or immunoglobulin degrading enzyme of *Streptococcus pyogenes* (IdeS) in Tris-buffered saline at 37° C. at pH 7.5 at antibody concentration of 0.5 mg/ml with protease concentration about approximately 1-2% (w/w) ratio to IgG. Amount of intact IgG can be assessed by SDS-PAGE using Aglient microcapillary electrophoresis.

"Modified" as used herein refers to a molecule that comprises an Fc polypeptide sequence or a polynucleotide sequence encoding the Fc that differs from a human wild type IgG1 Fc sequence by one or more modifications, for example substitutions, insertions or deletions of nucleotides or amino acids.

The term "$IC_{50}$ fold change ratio value" refers to the ratio of an $IC_{50}$ value for a wild type human IgG1 to an $IC_{50}$ value for the isolated modified Fc-domain containing molecule of the invention for FcγR measured in a competition assay with biotinylated human IgG1 to 0.2 μg/ml soluble human FcγRI. Competition can be measured using for example well known AlphaScreen® assays. AlphaScreen® is a registered trademark of PerkinElmer, Inc. or its subsidiaries.

The term "therapeutically effective amount" refers to an amount of a therapeutic agent as described herein comprising an Fc-domain which may be an antibody, antibody fragment, or derivative to treat a disease or disorder in a subject.

Proteases are divided into five major groups according to the structure of catalytic site and the amino acid (as one of the constituents) essential for its activity: serine proteinases, threonine proteinases, cysteine (thiol) proteinases, aspartic proteinases, and metalloproteinases.

Various extracellular proteases function throughout the body and in body compartments performing critical regulatory and metabolic processes. Acid-resistant proteases secreted into the stomach (such as pepsin) and serine proteases present in duodenum (trypsin and chymotrypsin) enable degradation of food protein within the gastrointestinal tract; proteases present in blood or serum (thrombin, plasmin, Hageman factor, etc.) play important role in blood-clotting, as well as lysis of the clots, and regulation of cells of the immune system. Proteases are present in or released from leukocytes (elastase, cathepsin G). Proteases determine the lifetime of other proteins thus playing an important metabolic role. Unlike hormones, interleukins or chemokines, no intracellular signaling or alteration in protein expression machinery is required, making proteolytic control one of the fastest regulatory switching mechanisms. Further, cooperative action of the proteases as in cascade reactions, results in a rapid and efficient amplification of an organism's response to a physiological signal.

Human IgG isotypes (the subclasses of mature gamma globulin class G antibodies; IgG1, IgG2, IgG3 and IgG4) exhibit differential capacity to recruit immune functions. For example, antibody-dependent cellular cytotoxicity (ADCC) is promoted by IgG1 and IgG3, antibody-dependent cellular phagocytosis (ADCP) is promoted by IgG1, IgG2, IgG3 and IgG4, and complement dependent cytotoxicity (CDC) is promoted by IgG1 and IgG3. Isotype-specific engagement of such immune functions is based on selectivity for Fc receptors on distinct immune cells and the ability to bind C1q thereby activating the assembly of a membrane attack complex (MAC). Among the various isotypes, relative affinity for Fcγ receptors, which include FcγRI, FcγRIIa/b/c, and FcγRIIIa/b; is high for IgG1 and IgG3. However, Fcγ affinity for IgG2 is considerably lower with the exception of FcγRIIa H131 polymorphism and IgG4 only has measurable affinity for FcγRI. Using comparative sequence analysis and co-crystal structures, the key contact residues for receptor binding have been mapped to the amino acid residues spanning the lower hinge and CH2 region ((Hezereh et al., 2001 J Virol 75:12161-8; Shields et al., 2001 J Biol Chem 276:6591-604).

The present invention provides modified Fc-domain containing molecules having improved characteristics suitable to be used as and/or incorporated into anti-cancer therapeutics or therapeutics that can be used to treat conditions which require Th1 responses or cell-mediated immunity such as viral infections (e.g. Variola, Varicella zoster, Epstein-Barr virus, Influenza virus, mumps virus, measles virus, and human immunodeficiency virus), bacterial infections (e.g. *Mycobacterium tuberculosis, Mycobacterium leprae, Legionella pneumophila, Listeria monocytogenes, Brucella* spp, *Salmonella* spp, *Shigella* spp, *Coxiella burnetii, Anaplasma phagocytophilum, Ehrlichia chaffeensis*, and *Staphylococcus aureus*), and protozoa infections (e.g. *Plasmodium* spp., *Toxoplasma gondii*, and *Leishmania* spp.).

The invention is based, at least in part, on the unexpected finding that Fc effector functions ADCC, ADCP and/or CDC in effector silenced IgG1 Fc mutant (E233P-L234V-L235A with G236 deleted; EU numbering) can be restored by mutations at the CH2 region with concomitant increased resistance of the modified Fc-domain containing molecule to proteolysis, while the Fc effector function of inducing macrophage IL-10 secretion is not restored.

The present invention provides polynucleotides encoding the modified Fc-domain containing molecules of the invention and complementary nucleic acids thereof, vectors, host cells, and methods of using the modified Fc-domain containing molecules. The present invention provides compositions for use as a medicament for treating a spectrum of diseases.

An engineered IgG1 molecule with IgG1 lower hinge residues E233, L234, L235 and G236 mutated to corresponding IgG2 lower hinge residues P233, V234, A235 (with IgG1 G236 deleted in IgG2), EU numbering, has been shown to demonstrate reduced FcγR binding and abolished Fc-mediated effector functions (variant G1Δb in Armour et al., Eur J Immunol 29:2613-2624 1999), (variant 2h in the specification=IgG1 E233P-L234V-L235A with G236 deleted).

IgG1 molecules are known to be more susceptible to proteolysis than IgG2, due to the presence of multiple protease cleavage sites at the upper and lower hinge region in IgG1 (FIG. 1). Therefore, it can be expected that the IgG1 molecule with IgG1 lower hinge residues E233, L234, L235 and G236 mutated to corresponding IgG2 lower hinge residues P233, V234, A235 (with IgG1 G236 deleted in IgG2), EU numbering, demonstrates increased protease resistance when compared to the wild type IgG1. However, the abolished effector function of this Fc domain may make it unsuitable to be coupled to antibody therapeutics where cell destruction and/or killing mediated by Fc effector functions are desired.

The present invention provides modified Fc-containing molecules or fragments thereof comprising a wild type human IgG1 Fc region of SEQ ID NO: 1 comprising a hinge, a CH2 domain and a CH3 domain, wherein the sequence of E233-L234-L235-G236 in the hinge is replaced with P233-V234-A235 with G236 deleted, and further having additional mutations in the CH2 region (EU numbering). The Fc-domain containing molecules of the invention demonstrate increased resistance to proteolysis when compared to the wild type (wt) IgG1, furthermore several modified Fc-containing molecules unexpectedly demonstrated increased resistance to proteolysis when compared to the wt IgG2 molecule. Surprisingly, introduced mutations in the CH2 region partially or fully restored binding to FcγRIIa, FcγRIIb or FcγRIIIa, and therefore the modified Fc-containing molecules of the invention had comparable or enhanced FcγRIIa-, FcγRIIb- or FcγRIIIa-mediated effector functions when compared to the wt IgG1 molecules. However, introduced mutations in the CH2 region did not restore binding to FcγRI. The lack of binding to FcγRI correlated with the inability of the engineered Fc-containing molecules of the invention to induce IL-10 secretion by macrophages.

The present invention demonstrates substitutions in multiple positions of the IgG1 constant regions (Fc) which unexpectedly provide a protease-resistant and functional (FcgR-engaging) Fc domain, except for FcγRI binding. As appreciated in the art, once the properties of a Fc-domain having a specific amino acid sequence are known, the information can be applied to the construction or modification of existing antibodies or Fc-polypeptide fusions. The protease-resistance conferred upon the compositions of the invention include protease resistance towards at least one of the proteases that cleave at residues of IgG1 hinge region that are substituted by alternate amino acids derived from the corresponding IgG2 residue, or proteases whose ability to cleave at IgG1 hinge region is affected by the substitutions. Exemplary proteases are matrix metalloproteases MMP-3, MMP-7, MMP-12, human neutrophile elastase (HNE), plasmin, cathepsin G, pepsin, IdeS, or glutamyl endopeptidase I from *Staph aureus* (FIG. 1) (Ryan et al. 2008 supra). The compositions of the invention may be resistant to proteolysis by additional proteases. Protease resistant to additional proteases can be assessed using the methods described herein.

Mutations to human wild type (wt) IgG1 (SEQ ID NO: 1) resulting in protease-resistant IgG1 molecules include replacing the IgG1 hinge region residues 214-237 in the EU numbering system (SEQ ID NO: 3) with the IgG2 wt hinge sequence (SEQ ID NO: 4), or replacing the IgG1 hinge region residues 214-237 in the EU numbering system (SEQ ID NO: 3) with a chimeric hinge (SEQ ID NO: 5) with IgG1 residues 233-235 replaced with corresponding IgG2 hinge residues as shown in Table 1.

TABLE 1

| Fc Designation | IgG Scaffold (EU 214-447) | Hinge/Proximal CH2 (EU 214-236) |
|---|---|---|
| IgG1 wt (UniProt P01857, 96-329) | hIgG1 | KVEPKSCDKTHTCPPCPA PELLG (SEQ ID NO: 3) |
| IgG2 wt (UniProt P01859, 97-326) | hIgG2 | TVERKCCVECPPCPAPPV A (SEQ ID NO: 4) |
| 2 hc | hIgG1 with complete IgG2 hinge region | SEQ ID NO: 4 |
| 2h | hIgG1 | KVEPKSCDKTHTCPPCPA PPVA (SEQ ID NO: 5) |

Compensating mutations in effector function enhancing regions can be selected from previously described substitutions as shown in Table 2 below.

TABLE 2

| Mutations (EU numbered positions) | Reference |
|---|---|
| S239D/I332E | 1 |
| E333A/K334A | 5 |
| F243L/R292P/Y300L | 3 |
| H268F/S324T/I332E | 4 |
| S239D/H268F/S324T/I332E | 4 |
| S267E/H268F/S324T/I332E | 4 |
| K326A/E333A | 2 |
| K326A/I332E/E333A | 1, 2 |
| S239D/K326A/E333A | 1, 2 |
| S267E/I332E | 1, 4 |
| G237X/S239D/I332E where X is A, D, P, Q, or S | 1 |
| S298A/E333A/K334A | 5 |

Increased Fc function constructs, previously cited by:
1. Lazar, Proc Natl Acad Sci USA 103: 4005-4010 (2006)
2. Idusogie, J Immunol 166: 2571-2575 (2001)
3. Stavenhagen, Cancer Res 67(18): 8882-90 (2007)
4. Moore, et al. MAbs 2(2): 181-189 (2010)
5. Shields et al., J Biol Chem 276: 6591-6604 (2001)

The multi-substituted IgG1 mutants were selected based on their relative affinities for human FcRs (FcγRI, FcγRIIa, FcγRIIb, FcγRIIIa assessed by AlphaScreen® competition assays). These mutants were further tested in the appropriate cellular systems for their ability to induce ADCC by PBMCs and ADCP by in vitro differentiated macrophages.

Using various measures of Fc-function based on in vitro assays, several protease-resistant Fc sequences were identified, that when incorporated into a complete IgG structure (H2L2), provide resistance to one or more of proteases acting at lower hinge residues (EU232-237) while having the ability to bind FcγR or promote cytolysis. The changes in Fc-related activities of selected constructs comprising a change at the hinge as well as in the CH2 region and categorized by receptor affinity and in vitro bioactivity are shown in Table 3.

Therefore, what is meant by reference to an Fc-containing composition resistant to proteolytic cleavage is that the composition is less likely to be degraded, lose activity, lose affinity for an Fc-binding partner such as an FcR upon exposure to a proteolytic enzyme than a comparator molecule, such as a wild-type human IgG1.

Biological Characterization of the Mutants

Fc-containing proteins can be compared for functionality by several well-known in vitro assays. Affinity for members of the FcγRI, FcγRII, and FcγRIII family of Fcγ receptors can be made using recombinant soluble forms or cell-associated forms of the receptors. In addition, affinity for FcRn, the receptor responsible for the prolonged circulating

TABLE 3

| Isotype/Construct | FcγRI | FcγRIIa | FcγRIIb | FcγRIIIa | ADCC | ADCP | CDC |
|---|---|---|---|---|---|---|---|
| IgG1 | +++++ | ++++ | ++++ | +++ | +++++ | +++++ | +++++ |
| IgG2 | − | ++ | − | +/− | − | ++ | − |
| IgG1 2h (PVA) | − | − | − | +/− | + | ++ | − |
| IgG1 2h E333A/K334A | − | + | − | +/− | − | ++ | n.d. |
| IgG1 2h S239D/I332E | +++ | +++++ | ++++ | ++++ | +++++ | ++++++ | − |
| IgG1 2h S239D/H268F/S324T/I332E | n.d. | ++++ | +++++ | ++++ | ++++++ | ++++++ | − |
| IgG1 2h S267E/H268F/S324T/I332E | n.d. | +++++ | ++++++ | +++ | +/− | + | +++++ |
| IgG1 2h K326A/E333A | n.d. | − | − | +/− | +/− | +++ | +++++ |

Method of Making the Altered Fc-Containing Molecules

The sites for substitution were chosen based on the desire to produce a composition having the structural features of a native antibody Fc, maintain stability, retain FcR binding and the capacity to stimulate the complement cascade, cell lysis, cell phagocytosis or cytokine release. Proteins, with altered or mutated amino acids can be created by routine molecular biology techniques such as site directed mutagenesis. Where a chimeric sequence is created, such as the Fc of the invention comprising portions of IgG1 and portions of IgG2, larger segments of the respective encoding nucleic acids may be spliced together or segments replaced by standard cloning techniques.

Testing Proteolytic Resistance

In order to determine whether one Fc-containing composition or antibody is more proteolytic resistant than another, or than the wild-type composition, the rate or extent to which a proteolytic enzyme degrades the different isolated Fc-containing compositions or antibodies is assessed. After a time period, the degradation is measured for the different compositions using a method capable of determining either scission of the chain directly, such as the formation of a unique cleavage site structure, or a measurement of newly formed fragments. Alternatively, where cleavage results in loss of activity, a functional assay can be performed, including a binding assay.

Proteolytic cleavage of an IgG1 can occur at any of the four polypeptide chains of the dimeric heterodimeric structure. Cleavage of IgG results in the generation of well characterized fragments such as Fab, (Fab')$_2$, and Fc fragments of approximate but unique molecular weights. The separation of such fragments generated during a proteolysis experiment can be accomplished using a size exclusion chromatography (SEC), by gel electrophoresis, by MALDI-TOF-MS (matrix-assisted laser/desorption ionization time-of-flight mass spectrometry) analyses after deglycosylation using PNGase F (peptide N-glycosidase F) as previously described (WO2007024743A2, WO2009045894A1).

half-life of IgGs, can be measured, for example using a ligand bound bead format such as "ALPHASCREEN" with recombinant soluble FcRn. AlphaScreen®, used in high throughput screening, is a homogenous assay technology which allows detection of molecular events such as binding. Coated "Donor" and "Acceptor" beads are the basis of the AlphaScreen® assay technology. AlphaScreen®, a bead based assay, works through the interaction of the beads coming close to each other, resulting in a cascade of chemical reactions that act to produce a greatly amplified signal. Direct or indirect, e.g. competitive binding, measurements can be applied for assessing relative affinities and avidities among proteins.

Each human IgG isotype (e.g. IgG1, IgG2, IgG3 and IgG4) recruit immune functions, such as antibody-dependent cellular cytotoxicity (ADCC, e.g. IgG1 and IgG3), antibody-dependent cellular phagocytosis (ADCP, e.g. IgG1, IgG2, IgG3 and IgG4), and complement dependent cytotoxicity (CDC, e.g. IgG1, IgG3) based on their differential selectivity for Fc receptors which reside on distinct immune cells, and the ability to bind C1q and activate the assembly of a membrane attack complex (MAC) resulting in CDC and CDP (complement dependent phagocytosis) through specific receptors binding complement components on effector macrophages. The hierarchy of ability to bind the initial component, C1q, of the complement cascade, of human isotypes is IgG1>IgG3>IgG2>IgG4 although complement activation by IgG2 and IgG4 in microbial infection is well-documented.

The engineered Fc-containing molecules of the invention can be tested in cell-based functional assays, such as ADCC assays and CDC assays to assess functional consequences of particular substitutions. Antibody-dependent cell-mediated cytotoxicity (ADCC) is a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. In one embodiment, the ADCC assay is configured to have NK cells as the primary effector cell, reflecting the functional effects on the FcγRIIIa which is the only activating Fcγ-type receptor known to be expressed by these cells.

Phagocytosis assays may also be used to compare immune effector functions of different mutants, as can assays that measure cellular responses, such as superoxide or inflammatory mediator release. In vivo models can be used, for example, in the case of using mutants of anti-CD3 antibodies to measure T cell activation in mice, an activity that is dependent on Fc domains engaging specific ligands, such as Fcγ receptors. Antibody directed activation of macrophages mediates antibody-dependent cellular phagocytosis (ADCP), causing opsonized target cells to be engulfed and digested by macrophages. In vitro, differentiated macrophages expressing high levels of FcRs can be differentiated into the M1 phenotype using INFγ or GM-CSF to expressed elevated levels of all FcRs (FcγRI, FcγRIIa, FcγRIIIa) relative to monocytes.

Ability of the modified Fc-containing molecules of the invention to elicit antibody-dependent cytokine release (ADCR) can be measured using for example a tumor cell line MDA-MB-231 as a target cell and a monocyte-derived macrophage or PBMC as an effector cell, and measuring cytokine release into the cell culture supernatant upon administering antibodies having the modified Fc-domains of the invention and variable regions binding to a surface molecule on MDA-MB-231 cell, such as tissue factor, using routine methods and as exemplified herein. Exemplary cytokines that can be measured are IL-10 and IFNγ. IL-10 and IFNγ can be measured using standard methods such as ELISA.

Production of Antibody Mutants

The compositions of the invention can be produced by engineered host cells using standard methods. The host cell chosen for expression of the recombinant Fc-containing protein or monoclonal antibody can contribute to the variation in for example oligosaccharide moieties in the immunoglobulin CH2 domain. Thus, one aspect of the invention involves the selection of appropriate host cells comprising polynucleotide sequences encoding the Fc-containing molecules of the invention for use as or development of a production cell expressing the desired therapeutic protein.

The host cell may be of mammalian origin or may be selected from COS-1, COS-7, HEK293, BHK21, CHO, BSC-1, Hep G2, 653, SP2/0, HeLa, myeloma, lymphoma, yeast, insect or plant cells, or any derivative, immortalized or transformed cell thereof.

Alternatively, the host cell may be selected from a species or organism incapable of glycosylating polypeptides, e.g. a prokaryotic cell or organism, such as a natural or engineered *E. coli* spp, *Klebsiella* spp., or *Pseudomonas* spp., engineered plant or insect cells.

Glycosylation at the naturally occurring glycosylation site within the IgG heavy chain (N297, EU numbering) also contributes to the Fc-binding affinity for FcγR. As the constant regions vary with isotype, each isotype possesses a distinct array of N-linked carbohydrate structures, which variably affect protein assembly, secretion or functional activity (Wright and Morrison 1997 Trends Biotech 15:26-32). The structure of the attached N-linked carbohydrate varies considerably, depending on the degree of processing, and can include high-mannose, multiply-branched as well as biantennary complex oligosaccharides and sialic acid (N-acetyl neuraminic acid or NANA), fucose, galactose and GlcNAc (N-acetyl glucosamine) residues as terminal sugars. The impact on effector functions of the host cell and oligosaccharide content of the antibodies has been recognized (Lifely et al., 1995 Glycobiology 5:813-22; Jefferis et al., 1998 Immunol Rev 163:59-76; Wright and Morrison, supra; Presta 2003. Curr Opin Struct Biol. 13:519-25). Furthermore, regarding a sugar chain in an antibody, it is reported that addition or modification of fucose at the proximal N-acetylglucosamine at the reducing end in the N-glycoside-linked sugar chain of an antibody changes the ADCC activity of the antibody significantly (WO00/61739).

Further, the relative contributions of galactosylation of the biantennary oligosaccharides, the presence of bisecting GlcNac, and fucosylation indicate that non-fucosylated Mabs display a greater capacity to enhance ADCC as measured in vitro and in vivo than other modifications to the N-linked biantennary oligosaccharide structures (Shields et al., 2002. J Biol Chem 277:26733-40; Niwa et al., 2004. Cancer Res 64:2127-33).

Expression or manufacture of a protease-resistant mAb of the invention using a host cell capable of, engineered to (as by knock-out or knock down of specific enzymes Shinkawa et al., 2003 J Biol Chem 278:3466-73; EP1176195A1) or induced, e.g. by environmental or nutritional manipulation, to produce a mAb having low fucose content is within the scope of the present invention.

Antibodies, Fc and Fc-Fusion Proteins

An antibody binding domain or fragments thereof can be produced using methods known to those skilled in the art and combined with the information provided herein and can include sequences or be derived from any mammal, for example human, mouse, rabbit, rat, rodent, primate, goat, or any combination thereof. Such antibodies may provide the basic structures and components of binding domains useful in producing the antibody constructs of the present invention. In one aspect, the antibody binding domains are obtained from hybridomas prepared by immunizing a mouse or other animal with the target peptides, cells or tissues extracts. The antibodies can be obtained using any of the hybridoma techniques well known in the art, see, e.g., Harlow and Lane, antibodies, a Laboratory Manual, Cold Spring Harbor, N.Y. (1989) entirely incorporated herein by reference or by selection of an antibody producing lymphocyte and cloning the nucleic acid sequences coding for the binding domains using techniques known in the art.

The present invention is directed to the constant region of a human IgG. Therefore, any antibody or fusion protein comprising a human Fc-domain wherein it is desirable that the final composition display both proteolytic resistance (as described herein) and the ability to bind FcgR and promote ADCC, ADCP, and/or CDC in an in vitro assay is encompassed by the present invention. A targeting moiety including an antibody Fv or single variable domain may be fused to the Fc-composition as desired. An "Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site. "Single-chain Fv" also abbreviated as "sFv" or "scFv" are antibody fragments that comprise the VH and VL antibody domains connected into a single polypeptide chain. The scFv polypeptide generally comprises a polypeptide linker between the VH and VL. The targeting moiety may also be selected from a paratope of an antibody (binding residues not limited to CDRs or variable domain structures);

an enzyme; a hormone; a receptor; a cytokine; an immune cell surface antigen; and an adhesion molecule when the construct is produced entirely by recombinant methods. The targeting moiety may also be of non-proteinaceous nature such as a carbohydrate, a lipid, a lipopolysaccharide, an organic molecule, or a metal or metal complex. Generally, when present, the targeting molecule will be connected to the Fc- by a linker which may be a polypeptide or nonpolypeptide.

Fc-containing proteins or Fc fragments described herein can be derived in several ways well known in the art. The antibody binding domains or Fc-fusion proteins or components and domains thereof may also be obtained from selecting from libraries of such domains or components, e.g., a phage library. A phage library can be created by inserting a library of random oligonucleotides or a library of polynucleotides containing sequences of interest, such as from the B-cells of an immunized animal or human (Smith, G. P. 1985. Science 228: 1315-1317). Antibody phage libraries contain heavy (H) and light (L) chain variable region pairs in one phage allowing the expression of single-chain Fv fragments or Fab fragments (Hoogenboom, et al. 2000, Immunol. Today 21(8) 371-8). The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable affinity and neutralization capabilities. Antibody or Fc libraries also can be created synthetically by selecting one or more human framework sequences and introducing collections of CDR cassettes derived from human antibody repertoires or through designed variation (Kretzschmar and von Ruden 2000, Current Opinion in Biotechnology 13:598-602). The positions of diversity are not limited to CDRs, but can also include the framework segments of the variable regions or may include other than antibody variable regions, such as peptides. In one aspect, a phage library capable of displaying dimeric Fc structures linked to the phage coat protein pIX as described in applicants co-pending application (U.S. Ser. No. 61/261,767) may be used to select novel Fc-comprising structures according to the present invention.

Libraries of target binding components, which may include target binding components other than antibody variable regions, may include ribosome display libraries, yeast display libraries, and bacterial display libraries. Ribosome display is a method of translating mRNAs into their cognate proteins while keeping the protein attached to the RNA. The nucleic acid coding sequence is recovered by RT-PCR (Mattheakis et al., 1994 Proc. Natl. Acad. Sci. USA 91:9022). Yeast display is based on the construction of fusion proteins of the membrane-associated alpha-agglutinin yeast adhesion receptor, aga1 and aga2, a part of the mating type system (Broder et al., 1997 Nature Biotechnology 15:553-7). Bacterial display is based on fusion of the target to exported bacterial proteins that associate with the cell membrane or cell wall (Chen and Georgiou 2002 Biotechnol Bioeng 79:496-503).

The invention also provides for nucleic acids encoding the compositions of the invention as isolated polynucleotides or as portions of expression vectors including vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode modified Fc-containing molecules of the invention are also within the scope of the invention.

The polynucleotides of the invention may be produced by chemical synthesis, such as solid phase polynucleotide synthesis on an automated polynucleotide synthesizer and assembled into complete single or double stranded molecules. Alternatively, the polynucleotides of the invention may be produced by other techniques, such as a PCR followed by routine cloning. Techniques for producing or obtaining polynucleotides of a given known sequence are well known in the art.

Use of the Fc-Containing Molecules

The compositions (antibody, Fc-fusions, Fc fragments) generated by any of the above described methods may be used to diagnose, treat, detect, or modulate human disease or specific pathologies in cells, tissues, organs, fluid, or, generally, a host. As taught herein, modification of the Fc portion of an antibody, Fc-fusion protein, or Fc fragment to reduce or ablate proteolytic degradation while retaining measurable Fc gamma receptor binding or specified effector functions can be combined with a binding domain, such as the paratope of an antibody or a ligand binding domain, which retains the original targeting specificity and biological activity. Examplary binding domains are a paratope of an antibody, one or more antibody CDRs, or one or more antibody variable domains; an enzyme; a hormone; a receptor; an extracellular domain of a membrane receptor; a cytokine; an immune cell surface antigen; and an adhesion molecule. The resulting constructs provide for antibodies and Fc-constructs with a superior spectrum of activities, biophysical properties, stability and ability to persist in the body of a host.

The applicants discovery of Fc sequences with unique combinations of resistance to physiologically-relevant proteases and ability or nonability to engage one or more Fcgamma receptors and/or the ability to affect cell lysis by activation of effector cells or complement provide for the ability to purpose the binding molecule for maximal effectiveness in a specified indication. For example, the ability to target aberrant host cells such as those involved in neoplasia or other unwanted proliferation such as in inappropriate angiogenesis, inappropriate fibrosis would be best suited by a molecule comprising a eukaryotic protease-resistant Fc of the present invention capable of ADCC and ADCP. In contrast, bacterial cells are readily destroyed by complement-mediated mechanisms. Therefore, bacterial infections may be treated by a suitable Fc-construct of the invention which is resistant to bacterial proteases and has the ability to invoke CDC.

Applicants have identified methods of selecting an Fc having the appropriate combination of properties and provided working examples of purpose specific modified Fc-comprising molecules. Molecules which eukaryotic protease-resistant and capable of one or more of ADCC, ADCP, and CDC include an Fc domain having the sequence of a human IgG1 in the hinge and CH2 regions, from about EU residues 214 to about residue 330 where at least residues 233-237 are substituted with PVA/(G236 deletion) and further comprising one or more substitutions in the CH2 domain whereby the molecule is capable of one or more of ADCC, ADCP, and CDC include the constructs 5, 7, 8, 9, 10, 11, 12, 14, 15, 16, and 17. In a particular embodiment, such molecules include substitutions selected from I332E in combination with other substitutions such as S239D/I332E (5, 14), S239D/H268F/I332E (not made), H268F/S324T/I332E (8), S239D/H268F/S324T/I332E (9), S267E/H268F/S324T/I332E (10), G237X/S239D/I332E where X is A or S (12); K326A/I332E/E333A (15), and S267E/I332E (17).

Molecules which are resistant to a prokaryotic protease and capable of CDC include those molecules comprising an Fc domain having the sequence of a human IgG1 in the hinge and CH2 regions, from about EU residues 214 to about residue 330 where at least residues 233-237 are substituted with PVA/(G236 deletion) and further comprising one or more substitutions in the CH2 domain selected from K326A/E333A (11), S267E/H268F/S324T/I332E (10), K326A/I332E/E333A (15), S239D/K326A/E333A (16), and S267E/I332E (17).

Molecules which are eukaryotic protease resistant but do not promote target cell lysis may also be advantageously used to treat a disease or conditions wherein target cell modulation and not target cell destruction is the objective such as by using an antibody or other Fc-construct as taught herein that is protease-resistant but has decreased ADCC, ADCP, or CDC as compared to wildtype IgG1. Molecules comprising a non-natural, non-wild type, Fc domain which are protease-resistant include those molecules comprising an Fc domain having the sequence of a human IgG1 in the hinge and CH2 regions, from about EU residues 214 to about residue 330 where at least residues 233-237 are substituted with PVA/(G236 deletion).

Thus, based on the teachings and examples herein, the presently enabled Fc-comprising constructs demonstrating enhanced resistance to a protease occurring in the mammalian subject and, optionally, having the ability to target an antigen on a cell provide improved therapeutic molecules relative to the therapeutic molecule which is not protease resistant.

The present invention provides modified Fc-containing molecules or fragments thereof comprising a wild type human IgG1 Fc region of SEQ ID NO: 1 comprising a hinge, a CH2 domain and a CH3 domain, wherein the sequence of E233-L234-L235-G236 in the hinge is replaced with P233-V234-A235 with G236 deleted, and having additional mutations in the CH2 region (EU numbering). The modified Fc-containing molecules have restored FcγRIIa, FcγRIIb and/or FcγRIIIa binding and comparable and/or enhanced ADCC, ADCP and/or CDC when compared to the wild type IgG1, however, they do not bind FcγRI. Lack of binding to FcγRI correlates with the inability of the Fc-containing molecules of the invention to induce macrophage IL-10 secretion. Many of the variants further induce IFNγ secretion from PBMCs, presumably from NK cells. IFNγ stimulates the tumor-killing functions of macrophages, enhances cross-presentation, increases expression of co-stimulatory molecules and MHC I and II, and drives Th1 immune responses, thereby promoting the pro-inflammatory milieu beneficial for anti-tumor therapeutics.

Regulatory macrophages are known to actively contribute to tumor growth via angiogenesis and immunosuppression (Biswas and Mantovani 2010 Nat Immunol. 11:889-96). Activation of regulatory macrophages characterized by secretion of anti-inflammatory and proangiogenic mediators IL-10 and VEGF in a tumor microenvironment has been suggested to be causative for lack of efficacy of anti-EGFR monoclonal antibody cetuximab in combination with anti-VEGF mAb bevacizumab. It was suggested that activation of the regulatory macrophages occur via engagement with the high-affinity FcγRIIIA (Pander et al., 2011 Clin Cancer Res 17:5668-73). In contrast, U.S. Pat. No. 6,660,266 describes FcγRI ligation causative for induced secretion of IL-10 by macrophages.

Modified Fc-containing molecules or fragments thereof comprising a wild type human IgG1 Fc region of SEQ ID NO: 1 comprising a hinge, a CH2 domain and a CH3 domain, wherein the sequence of E233-L234-L235-G236 in the hinge is replaced with P233-V234-A235 with G236 deleted, and having additional mutations in the CH2 region (EU numbering) that are resistant to proteases, have ADCC capacity comparable or equal to the wt IgG1 and strong ADCP (at 24 hours) but do not induce IL-10 secretion from macrophages include constructs 5, 8, 9, 12, 14, 15, and 16 having CH2 mutations S239D/I332E (5, 14), H268F/S324T/I332E (8), S239D/H268F/S324T/I332E (9), G237X/S239D/I332E where X is A or S (12), K326A/I332E/E333A (15), and S239D/K326A/E333A (16). These molecules have beneficial characteristics to be used as and/or incorporated into therapeutic molecules, i.e. protease resistance and strong cellular cytotoxicity effects without potentially converting pro-inflammatory macrophages into IL-10 secreting regulatory macrophages. These Fc-containing molecules can be used to treat any disease associated with unwanted proliferation of cells as exemplified infra.

Modified Fc-containing molecules or fragments thereof comprising a wild type human IgG1 Fc region of SEQ ID NO: 1 comprising a hinge, a CH2 domain and a CH3 domain, wherein the sequence of E233-L234-L235-G236 in the hinge is replaced with P233-V234-A235 with G236 deleted, and having additional mutations in the CH2 region (EU numbering) that are resistant to proteases, have strong CDC capacity but do not induce IL-10 secretion from macrophages include constructs, 10, 11, 15, 16 and 17 having CH2 mutations S267E/H268F/S324T/I332E (10), K326A/E333A (11), K326A/I332E/E333A (15), S239D/K326A/E333A (16) and S267E/I332E (17). These Fc-containing molecules can be used to treat for example microbial infections. Intrinsic antibody-dependent enhancement (ADE), ligation of macrophage Fcγ receptors by IgG immune complexes resulting in increased infections output by infected cells has been attributed at least part to increased immunosuppressive action of IL-10 produced by infected macrophages upon FcγR ligation (Halstend et al., Lancet Infect Dis 10:712-22, 2010). Therefore, the Fc-containing molecules of the invention may be particularly useful in treatment of infections that are/may be associated with intrinsic ADE. Exemplary infections that may be treated with the modified protease resistant Fc-containing molecules of the invention with strong CDC and lack of IL-10 secretion are infections caused by intracellular parasites and bacteria, such as *Mycobacterium tuberculosis, Mycobacterium leprae, Legionella pneumophila, Listeria monocytogenes, Brucella* spp, *Salmonella* spp, *Shigella* spp, *Coxiella burnetii, Anaplasma phagocytophilum, Ehrlichia chaffeensis*, protozoans, *Leishmania* spp, *Toxoplasma gondii*, and fungi (eg, *Histoplasma capsulatum*), viral infections for those viruses that replicate in macrophages in vivo, such as West Nile Virus, Ross River Virus (RRV) and dengue virus, and other conditions as exemplified supra. Additionally, the presence of IL-10 secreting macrophages within methicillin resistant *Staphylococcus aureus* infected tissues from thermally injured mice correlated with sepsis formation and death, whereas the presence of non-IL-10 secreting M1 macrophages in non-thermally injured mice correlated with abscess formation and survival (Asai et. Al, Infect Immun 78(10):4311-19 2010). Therefore, the use of Fc-containing molecules of the invention may be useful in the treatment of methicillin-resistant *Staphylococcus aureus* (MSRA) infections. To target the modified Fc-containing molecule to recognize a particular parasite, bacteria or virus, the Fc can be incorporated in an IgG1 antibody that comprises variable regions that recognize a surface antigen of the microbe. Exemplary surface antigens that can be used to target the modified Fc-containing molecule of the invention include *Staphylococcus aureus* iron regulated surface determinant B (IsdB), teichoic acid (TA), lipoteichoic acid (LTA), clumping factor A, clumping factor B, capsular polysaccharide (CP) types 5 (CP5) and 8 (CP8), autolysin, Protein A, sortase, poly-N-acetyl glucosamine (PNAG), peptidoglycan (PG), and other known cell wall components of *Staph*. Additional surface molecules that can be used are known to those skilled in the art.

Administration

As proteolytic enzymes are localized according to their rate of formation or accumulation, for example pepsin in the digestive tract, or matrix metalloproteinases (MMPs) in regions of tissue remodeling or malignant growth, the compositions of the invention are particularly suited for uses in which a body compartment is known to contain proteases or abnormally high protease content.

The invention provides for stable formulations of a protease-resistant IgG composition such as an antibody, which is preferably an aqueous phosphate buffered saline or mixed salt solution, as well as preserved solutions and formulations as well as multi-use preserved formulations suitable for pharmaceutical or veterinary use, comprising at least one protease-resistant antibody in a pharmaceutically acceptable formulation. Suitable vehicles and their formulation, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

A protease-resistant IgG composition with effector function in stable or preserved formulations as described herein or known in the art, can be administered to a patient in accordance with the present invention via a variety of delivery methods including intravenous (I.V.); intramuscular (I.M.); subcutaneously (S.C.); transdermal; pulmonary; transmucosal; using a formulation in an implant, osmotic pump, cartridge, micropump; or other means appreciated by the skilled artisan, as well-known in the art.

For site specific administration to a body compartment or cavity, the administration may be intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or by transdermal means.

The diseases or pathologies that may be amenable to treatment using a composition provided by the invention include, but are not limited to, diseases in which unwanted proliferation, activation or migration of cells is deleterious such as malignancy, hyper-active or unbalanced immune responses, fibrotic tissue formation, or infection as the compositions provide for the activation of cytotoxic or cytolytic mechanisms of the host immune system through FcγR-driven mechanisms. Such diseases include malignancies: leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoproliferative disease, cutaneous T-cell lymphoma, Hodgkin's disease, Castleman's disease, glioma, glioblastoma, astracytoma, a malignant lymphoma, non-Hodgkin's lymphoma, Burkitt's lymphoma, multiple myeloma, Kaposi's sarcoma, colorectal carcinoma, pancreatic carcinoma, renal cell carcinoma, breast cancer, ductal carcinoma, lipoma, nasopharyngeal carcinoma, prostate cancer, testicular cancer, ovarian cancer, retinoblastoma, malignant histiocytosis, hypercalcemia of malignancy, plasmacytomas, chondrosarcomas, sarcomas, Merkel cell cancer, heptocellular carcinoma, hepatoma, basal cell cancer, adenocarcinomas, squamous cell carcinomas, sarcomas (such as Ewings, Kaposi's, childhood soft tissue, adult), melanomas, metastatic melanoma, hemangioma, metastatic disease, osteosarcoma, rhabdomyosarcoma, thymoma and thymic carcinoma, cancer related bone resorption, endometrial cancer, vaginal cancer, uterine cancer, Wilms tumors, cancer related bone pain, and the like.

Targeted molecules capable of binding antigens on malignant lymphocytes include B-cell antigens such as CD19, CD20, and CD22. Solid tumors derived from epidermal tissue often display and are stimulated by ligand binding to epidermal growth factor receptors known as the ErbB1, ErbB2, ErbB3 and other receptor capable of signaling or causing a proliferative response or an anti-apoptotic response leading to unchecked growth of the tumor. Other common antigens on solid tumors are tissue factor or RON.

The compositions, when combined with an appropriate target binding domain, are also useful in treating an infectious disease caused by bacterial (such as *Streptococcus, Staphylococcus,* and *E. coli*), viral (such as influenza, AIDS, RSV, SARS, and West Nile Virus), fungal (such as Aspergillosis, coccidiodomycosis, cryptococcosis, or Candidiasis), or protozoan infection (such as trypanosomiasis, toxoplasmosis, giardia, or malaria).

The compositions are useful in treating general immunological and autoimmune disorders including but not limited to the rheumatic diseases, psoriasis, and scleroderma.

The compositions are useful in treating disorders associated with inappropriate angiogenesis. Angiogenesis is the process of generating new capillary blood vessels, and it results from activated proliferation of endothelial cells. Neovascularization is tightly regulated, and occurs only during embryonic development, tissue remodeling, wound healing and periodic cycle of corpus luteum development (Folkman and Cotran, 1976 Int. Rev. Exp. Pathol. 16, 207-48). Endothelial cells normally proliferate much more slowly than other types of cells in the body. However, if the proliferation rate of these cells becomes unregulated, pathological angiogenesis can result. Pathological angiogenesis is involved in many diseases. For example, cardiovascular diseases such as angioma, angiofibroma, vascular deformity, atherosclerosis, synechia and edemic sclerosis; and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis are related to angiogenesis. Chronic inflammatory diseases such as arthritis; dermatological diseases such as psoriasis, telangiectasis, pyogenic granuloma, seborrheic dermatitis, venous ulcers, acne, rosacea (acne rosacea or erythematosa), warts (verrucas), eczema, hemangiomas, lymphangiogenesis are also angiogenesis-dependent.

Diabetic retinopathy can take one of two forms, non-proliferative or proliferative. Proliferative retinopathy is characterized by abnormal new vessel formation (neovascularization), which grows on the vitreous surface or extends into the vitreous cavity. Macular degeneration, likewise takes two forms, dry and wet. In exudative macular degeneration (wet form), which is much less common, there is formation of a subretinal network of choroidal neovascularization often associated with intraretinal hemorrhage, subretinal fluid, pigment epithelial detachment, and hyperpigmentation. Neovascular glaucoma occurs in patients with diabetes or central retinal vein occlusion or inflammatory precipitates associated with uveitis pulling the iris up into the angle (Ch. 99. The Merck Manual 17th Ed. 1999).

Rheumatoid arthritis, an inflammatory disease, also results in inappropriate angiogenesis. The growth of vascular endothelial cells in the synovial cavity is activated by the inflammatory cytokines, and results in cartilage destruction and replacement with pannus in the articulation (Koch et al., 1986, Arth; 15 Rhenium, 29:471-79; Stupack et al., 1999 Braz. J. Med. Biol. Res., 32:578-81; Koch, 1998 Arthritis Rheum, 41:951-62).

The compositions are useful in treating psoriasis, which is caused by uncontrolled proliferation of skin cells. Fast growing cell requires sufficient blood supply, and abnormal angiogenesis is induced in psoriasis (Folkman, 1972 J. Invest. Dermatol. 59:40-8).

A number of factors are involved in processes and events leading to angiogenesis: cell adhesion molecules, integrins, vascular endothelial growth factor (VEGF), TNFalpha, bFGF, and cytokines including IL-6 and IL-12. For example, the closely related but distinct integrins alphaVbeta3 and aVb5 have been shown to mediate independent pathways in the angiogenic process. An antibody generated against alphaVbeta3 blocked basic fibroblast growth factor (bFGF) induced angiogenesis, whereas an antibody specific to aVb5 inhibited vascular endothelial growth factor (VEGF) induced angiogenesis (Eliceiri et al., 1999 J. Clin. Invest. 103:1227-30; Friedlander et al., 1995 Science 270:1500-2). Therefore, the invention encompasses the use of targeting binding domains directed to these targets in the compositions of the invention for use in treating diseases where the inhibition of angiogenesis is indicated.

The applicants co-pending published International Patent Application WO2009023457A1, hereby incorporated by reference into the present application, discloses a strategy to restore effector function to cleaved IgGs using anti-hinge cleavage site epitope specific monoclonal antibodies. Incorporating a protease-resistant and effector function competent Fc in accordance with the present invention with anti-hinge domains to produce a bivalent antibody would produce a therapeutic mAb capable of both restoring Fc-effector function to cleaved IgGs while rendering the therapeutic resistant to silencing by proteolytic cleavage. Accordingly, the present invention encompasses the incorporation of a protease-resistant Fc constant region of the invention with an anti-hinge variable region mAb as described.

While having described the invention in general terms, the embodiments of the invention will be further disclosed in the following examples that should not be construed as limiting the scope of the claims.

Example 1: Construction of and Testing of Fc Mutants

A series of constructs (shown in FIG. 2 and combining the hinge region of Table 1 with activity restoring mutations in the CH2 region selected from Table 2) were generated using standard recombinant technology. The designation 2hc denotes that the IgG1 constant domain corresponding to the Kabat numbering of the EU antibody (EU numbering) from 214 to 236 (SEQ ID NO: 3) have been replaced with the corresponding IgG2 sequence (SEQ ID NO: 4). The designation 2h denotes that the residues of IgG1 E233-L234-L235-G236 are replaced by the corresponding residues of IgG2 P233-V234-A235 with G235 deleted.

TABLE 4

| Construct | Designation/Construct | IgG Isotype Scaffold | EU 214-447 Sequence | CD142 | CD20 |
|---|---|---|---|---|---|
| 1 | IgG1 wt | hIgG1 | SEQ ID NO: 1 | X | X |
| 2 | IgG2 wt | hIgG2 | SEQ ID NO: 2 | X | X |
| 3 | 2 hc (all hinge residues from IgG2) | hIgG1 | SEQ ID NO: 6 | X | |
| 4 | 2h | hIgG1 | SEQ ID NO: 7 | X | X |
| 5 | 2h S239D/I332E | hIgG1 | SEQ ID NO: 8 | X | X |
| 6 | 2h E333A/K334A | hIgG1 | SEQ ID NO: 9 | X | |
| 7 | 2h F243L/R292P/Y300L | hIgG1 | SEQ ID NO: 10 | X | X |
| 8 | 2h H268F/S324T/I332E | hIgG1 | SEQ ID NO: 11 | X | X |
| 9 | 2h S239D/H268F/S324T/I332E | hIgG1 | SEQ ID NO: 12 | X | X |
| 10 | 2h S267E/H268F/S324T/I332E | hIgG1 | SEQ ID NO: 13 | X | X |
| 11 | 2h K326A/E333A | hIgG1 | SEQ ID NO: 14 | X | X |
| 12 | 2h G237X/S239D/I332E where X is A, D, P, Q or S | hIgG1 | SEQ ID NO: 15 | X | |
| 13 | 2hc S239D/I332E | hIgG1 | SEQ ID NO: 16 | X | |
| 14 | IgG2 S239D/I332E | hIgG2 | SEQ ID NO: 17 | X | |

The variable regions of the one set of antibody constructs bind to CD142 (tissue factor) which allowed testing of Fc-dependent cell-killing of the antibodies in cellular assays using MDA-MB-231 (ATCC, HTB-26™) expressing tissue factor (Brerski et al., Proc Natl Acad Sci USA 106:17864-17869 2009). An additional panel was generated with variable regions that bind to CD20 which allowed testing of CDC activity using WIL2-S cells displaying CD20 (ATCC, CRL-8885) (Brerski et al., Proc Natl Acad Sci USA 106: 17864-17869 2009). All of the antibodies were expressed transiently in 293T cells using standard cloning methods and procedures. MAbs were purified using protein A columns to greater than 95% purity prior to experimental analysis.

Protease Digestion of Wild Type and mAb Constructs

Protease digestions of purified IgGs were carried out at pH 7.5 in phosphate-buffered saline (PBS) or, for the MMPs (MMP-3, MMP-7, MMP-12 and MMP-13 were all obtained from Enzo Life Sciences), in Tris-buffered saline buffer at 37° C. IdeS was obtained from Genovis, and GluV8 was obtained from Pierce. $CaCl_2$ was included in the MMP reactions at 5 mM for all MMPs tested. Antibody concentrations were 0.5 mg/mL and reactions were initiated by addition of enzyme to approximately 1-2% (w/w) ratio to IgG unless otherwise specified. IgG cleavage was assessed by analysis of the electrophorograms after Agilent Biosizing microcapillary electrophoresis (Agilent Technologies). All digests were performed in duplicate.

ALPHASCREEN® Competition Binding Assays

Competition binding studies were carried out in half-well volume 96-well opaque plates (Corning) in assay buffer (PBS, 0.05% BSA, 0.01% Tween-20) at pH 7.4. All competition studies were carried out against biotinylated IgG1 (1 IgG: 2 biotin, using EZ Link™ NHS-LC-biotin, Pierce) at a fixed concentration and competing wild type and protease-resistant constructs in serial 3-fold dilutions. FcγR concentrations were 0.2 µg/ml in final concentration of the assays. Biotinylated IgG1 (0.2 µg/ml final) and wild type and protease-resistant antibodies (10 µl) were sequentially added to each row of a 96-well plate in duplicates. Thereafter designated FcγRs were added followed by the sequential addition of 10 µl each of 1/50 diluted nickel chelate (Ni)-acceptor beads and streptavidin (SA)-donor beads. The opaque plate was covered with an aluminum seal to maintain light-safe conditions while shaking for 30 minutes on an Orbital shaker. Thereafter the seal was removed and the fluorescence was read on an ENVISION™ plate reader (PerkinElmer) equipped with appropriate filter set of AlphaScreen® excitation/emission spectra. Raw data was transferred to GraphPad PRISM™ software and normalized for maximal signal and competition curves were plotted using non-linear regression curve-fitting software.

Results

Of initial interest was to determine the susceptibility of mAb constructs to a number of physiologically-relevant proteases previously shown to cleave IgG1 in the lower hinge region; MMP-3, MMP-7, MMP-12, MMP-13, GluV8 and IdeS. Constructs 1-5, 7, 9-11, 12 (G237A), 13-14 were tested as CD142 binding antibodies. The proteases cleaved IgG1 to a varying degree over 24 hours. Whereas MMP-3, MMP-12, IdeS eliminated all intact IgG1 (construct 1) within 24 hours, MMP-7 cleaved about 30%, MMP-13 about 40% and GluV8 about 60%. Construct 4 (2h) and those constructs with the 2h lower hinge modification were resistant to all of the MMPs to more or less the same degree. Construct 4 was resistant to GluV8 but not IdeS. Construct 2 were also more resistant to GluV8 digestion.

Figure 3A:
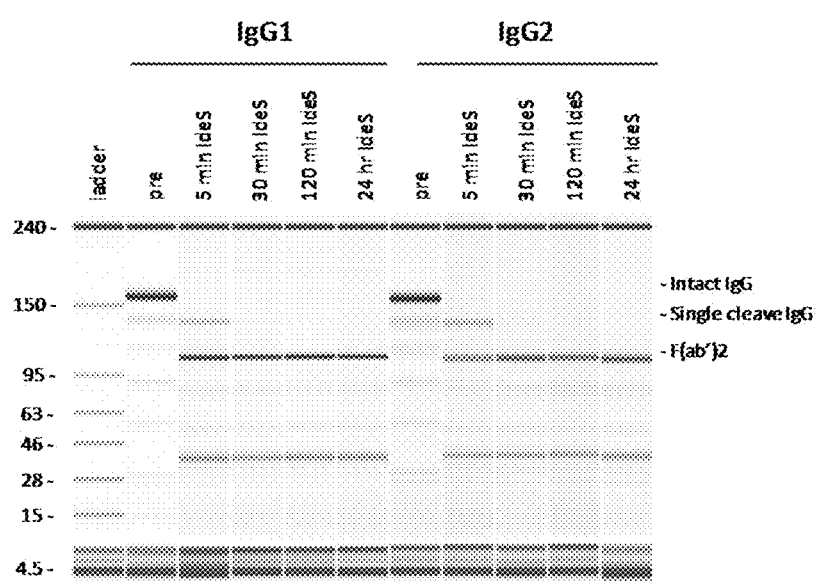
FIGS. 3A-B show digestion analyses of antibodies comprising different IgG isotypes (A) and new constructs thereof as described in FIG. 2 (B) with the protease IdeS at different time points.
Figure 3B:
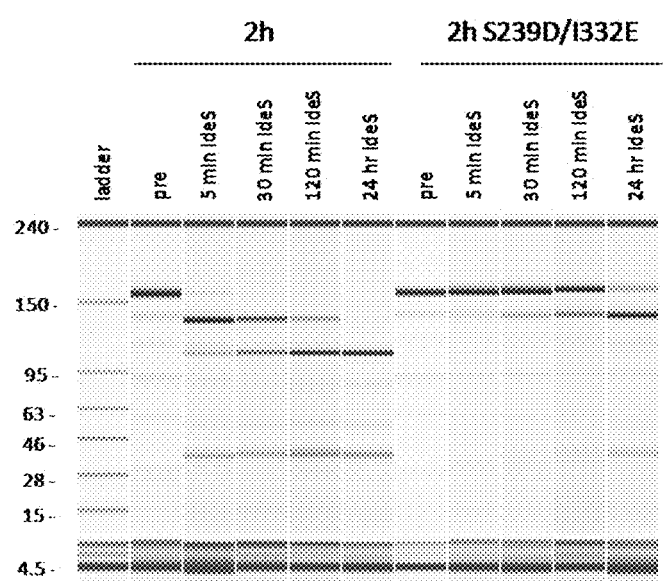
Figure 4A:
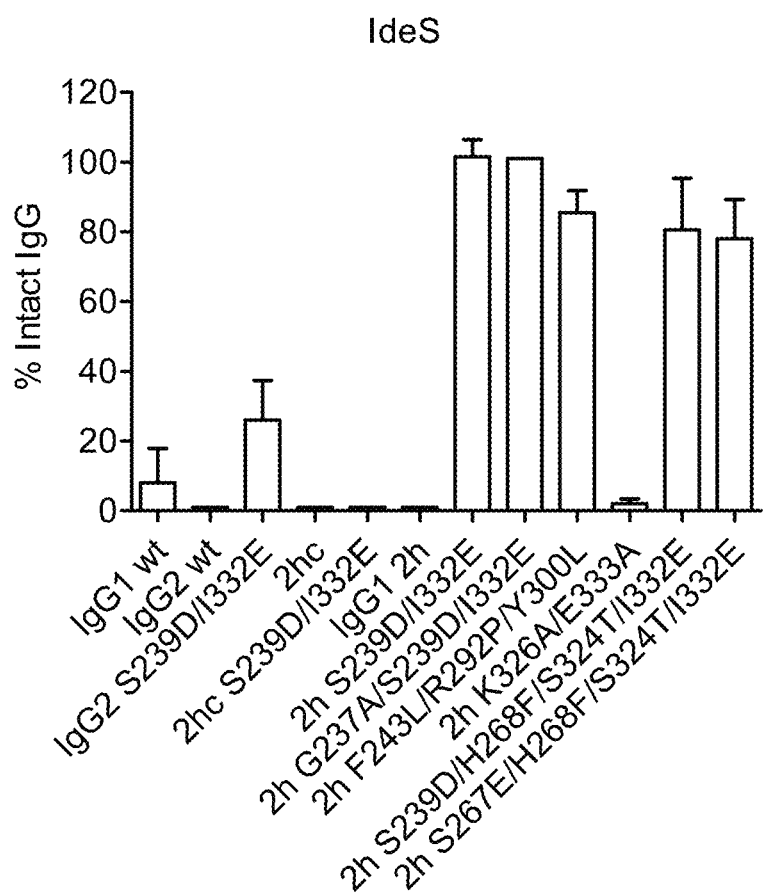
FIG. 4A-D shows digestion of IgG constructs with IdeS (A) GluV8 (B), MMP-3 (C), and MMP-12 (D) after a 24 hour incubation (n=2).
Figure 4B:
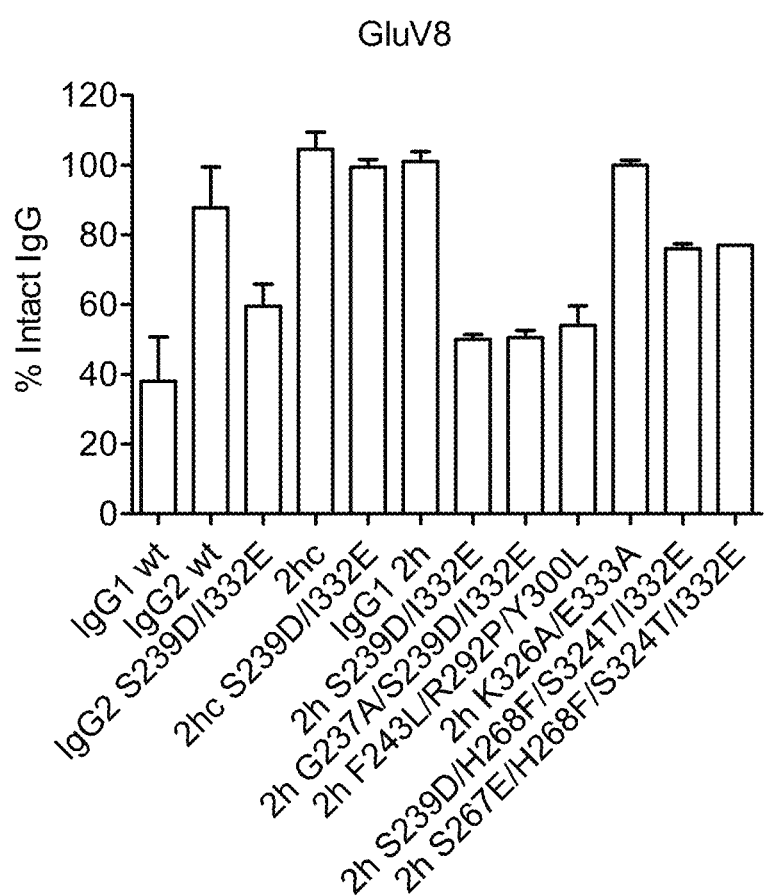
Figure 4C:
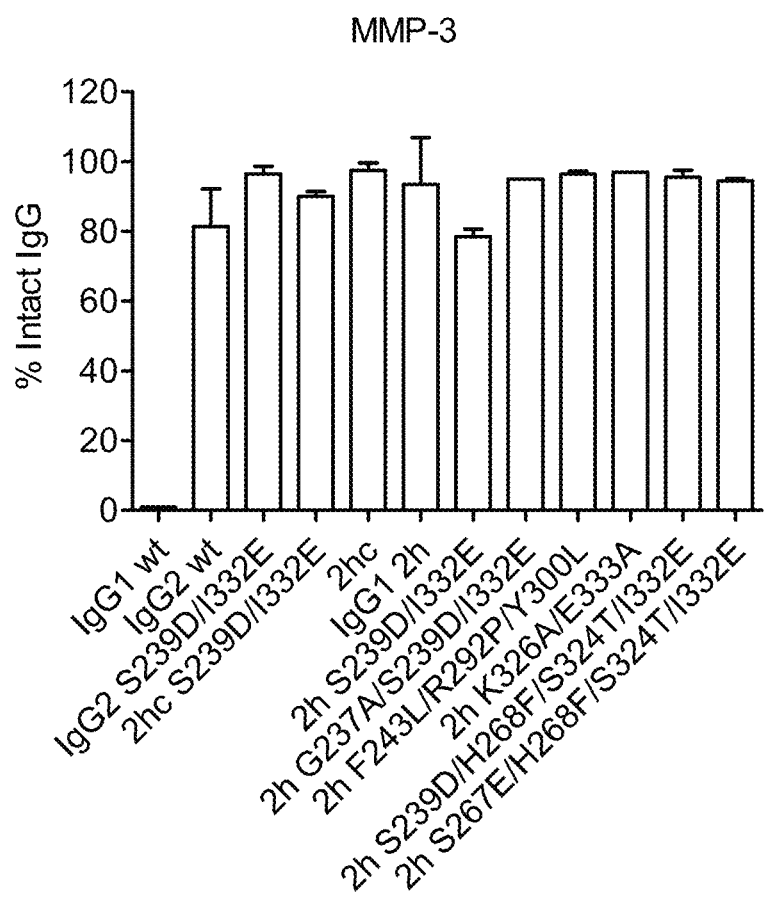
Figure 4D:
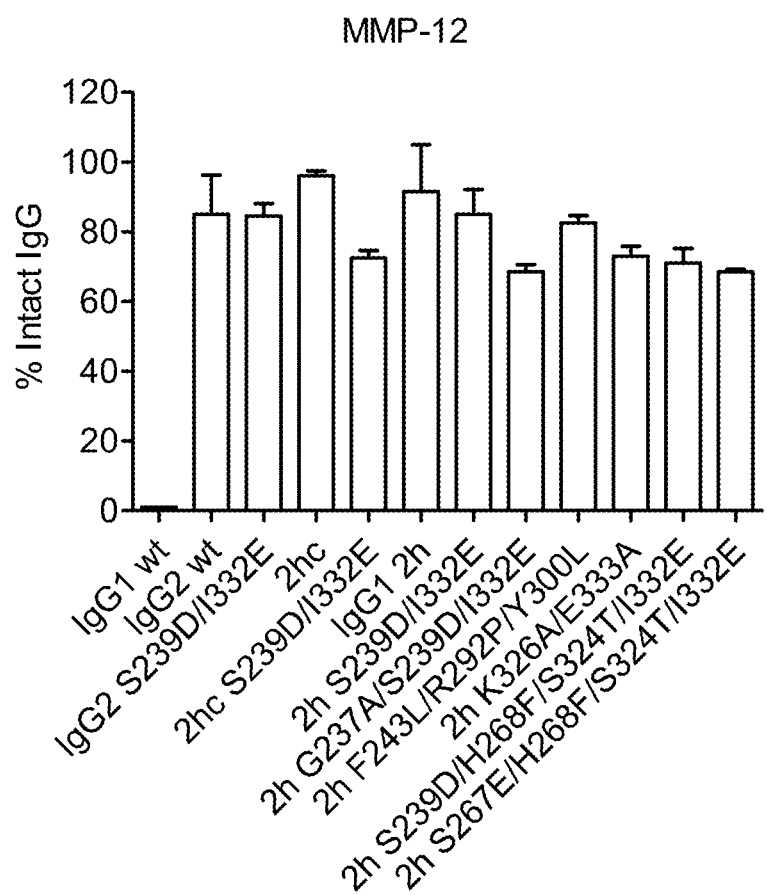

IdeS has been shown to cleave all human IgG isotypes (von Pawel-Rammingen et al., EMBO 21:1607-1615 2002). The data from a time course study (FIG. 3A) indicate that IdeS rapidly converted IgG1 (1) and IgG2 (2) to the F(ab')$_2$ fragment (within 5 minutes of incubation) while the IgG1 sample 2h (4) had single-cleaved intermediate through 120 minutes. Of the constructs tested, 2h S239D/I332E (5) was the most proteolytic resistant construct to IdeS (FIG. 3B), with intact IgG detected even after 24 hour incubation (the other antibody constructs had no detectable intact IgG by 5 minutes). The mutation of S239D in (5) which is near the IdeS cleavage point between G236 and G237, may contribute to the additional protease resistance as compared to IgG1 2h (4).

A panel of 12 anti-CD142 antibody constructs (1-5, 7, 9-13, and 14) was tested along with their wildtype IgG1 and IgG2 counterparts for susceptibility to proteolysis by IdeS, GluV8, MMP-3, and MMP-12, and. The data for intact IgG remaining after 24 hour incubation was calculated from the electrophorograms and shown in FIG. 4A-D.

The data demonstrated that IgG1 wt (1), IgG2 wt (2), 2hc (3), IgG1 2h (4), 2hc S239D/I332E (13), IgG2 S239D/I332E (14), and 2h K326A/E333A (11) were susceptible to proteolysis by IdeS after a 24 hour incubation. In contrast, the constructs 2h S239D/I332E (5), 2h G237A/S239D/I332E (12), 2h F243L/R292P/Y300L (7), 2h S239D/H268F/S324T/I332E (9), and 2h S267E/H268F/S324T/I332E (10) were resistant to proteolysis by IdeS. Surprisingly, constructs with more IgG2 hinge region substitutions (comprising SEQ ID NO: 4) were not resistant to IdeS proteolysis. The construct IgG2 S239D/I332E had less than 40% intact IgG remaining after 24 hours digestion with IdeS.

Digestion with the GluV8 protease from *Staph aureus* indicated that the constructs IgG2 S239D/I332E (14), 2h S239D/I332E (5), 2h G237A/S239D/I332E (12), and 2h F243L/R292P/Y300L (7) had a range of 40-60% intact IgG remaining after a 24 hour digestion, similar to the level of cleavage seen for IgG1 wt (1). The constructs IgG2 wt (2), 2hc (3), 2hc S239D/I332E (14), IgG1 2h (4), IgG1 2h K326A/E333A (11), 2h S239D/H268F/S324T/I332E (9), and 2h S267E/H268F/S324T/I332E (10) showed increased resistance to proteolysis by GluV8 (all having greater than 75% intact IgG remaining) relative to IgG1 wt.

MMP-3 and MMP-12 represent two types of cancer associated proteases. Less than 5% intact IgG1 wt was detected after digestion with both MMP-3 and MMP-12. In contrast, human IgG2 wt and all of the constructs tested displayed increased protease-resistance to both MMP-3 and MMP-12 as demonstrated by greater than 60% intact IgG remaining after 24 hours of digestion.

Fcγ Receptor Binding Results

Figure 5A:
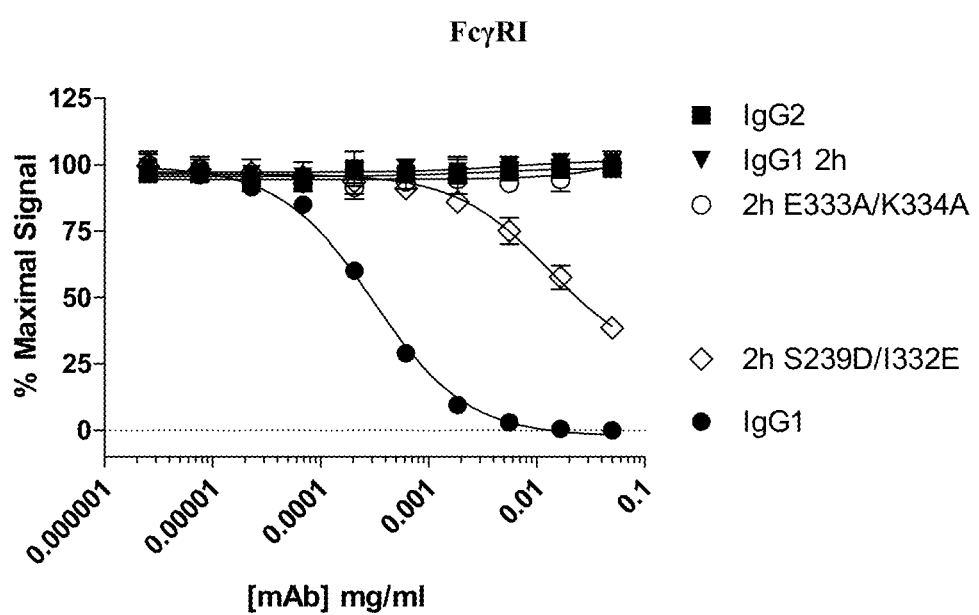
Figure 5B:
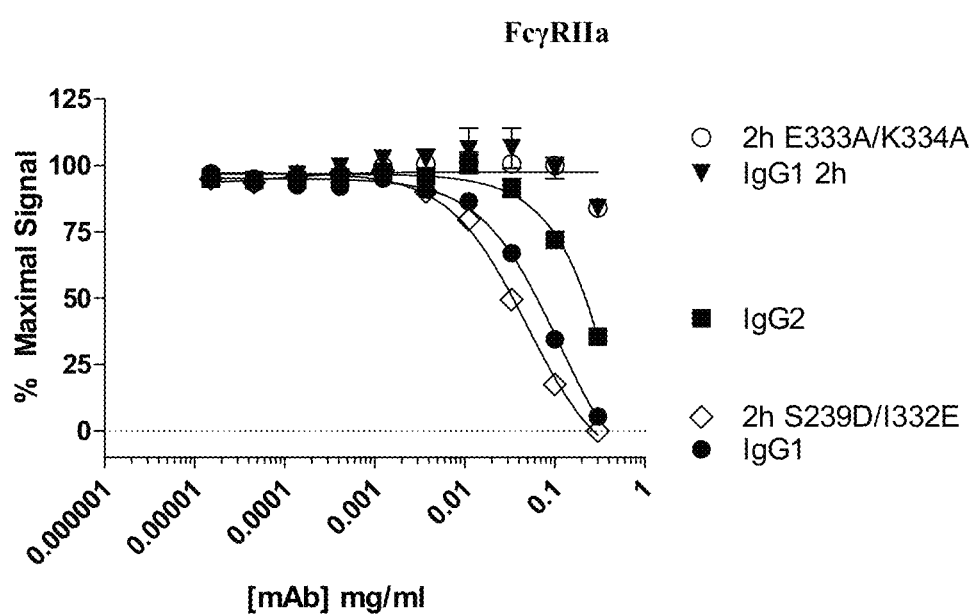

The ability of some of the Fc- constructs to compete for binding to the Fcγ family of receptors with wt IgG1 was assessed. The ability of the constructs to reduce maximum signal produced by the biotinylated IgG1 are shown in FIG. 5A-G. The initial screens included Constructs 1-2, 4-6. For the initial group of constructs tested, IgG2 (2), IgG1 2h (4), and 2h E333A/K334A (6) showed no detectable binding to the high affinity FcγRI, while a wild-type IgG1 showed robust binding. The 2h S239D/I332E (5) showed detectable but reduced binding to FcγRI compared to IgG1. The IgG1 2h (4) and 2h E333A/K334A (6) showed no detectable binding to FcγRIIa, while the 2h S239D/I332E (5) construct showed comparable binding to IgG1 wt (FIG. 5B). Three constructs: IgG2 (2), IgG1 2h (4), and 2h E333A/K334A (6) showed no detectable binding to FcγRIIb, while IgG1 (1) and 2h S239D/I332E (5) showed comparable binding (FIG. 5D). IgG2 (2), IgG1 2h (4), and 2h E333A/K334A (6) showed comparable, but reduced binding to FcγRIIIa compared to IgG1. The 2h S239D/I332E (5) construct displayed the highest level of binding to FcγRIIIa, even higher than IgG1 wt (FIG. 5F).

Figure 5C:
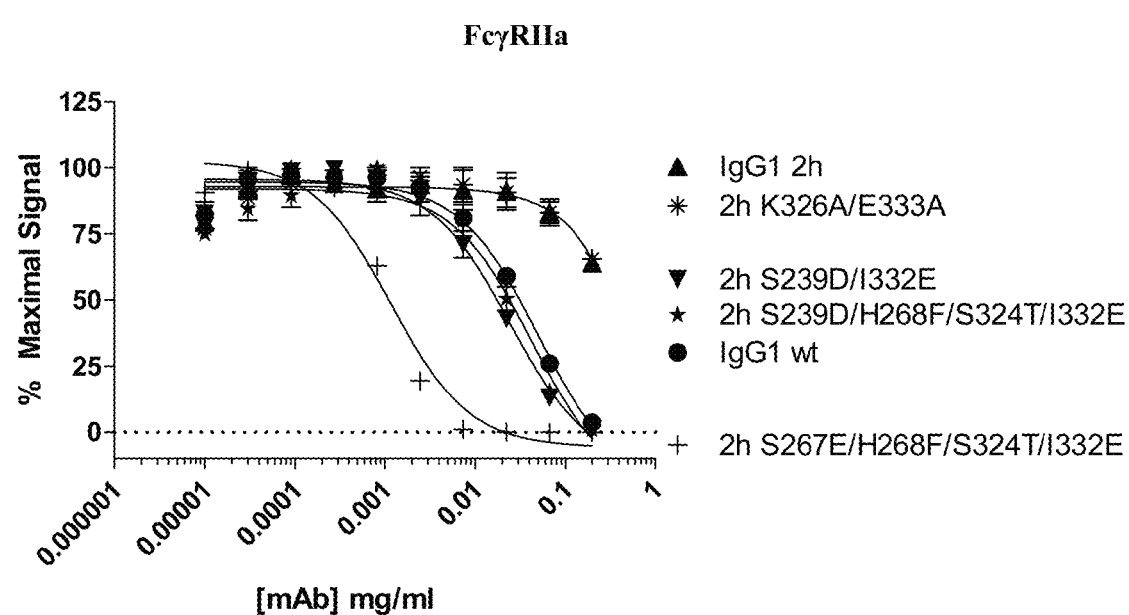
Figure 5D:
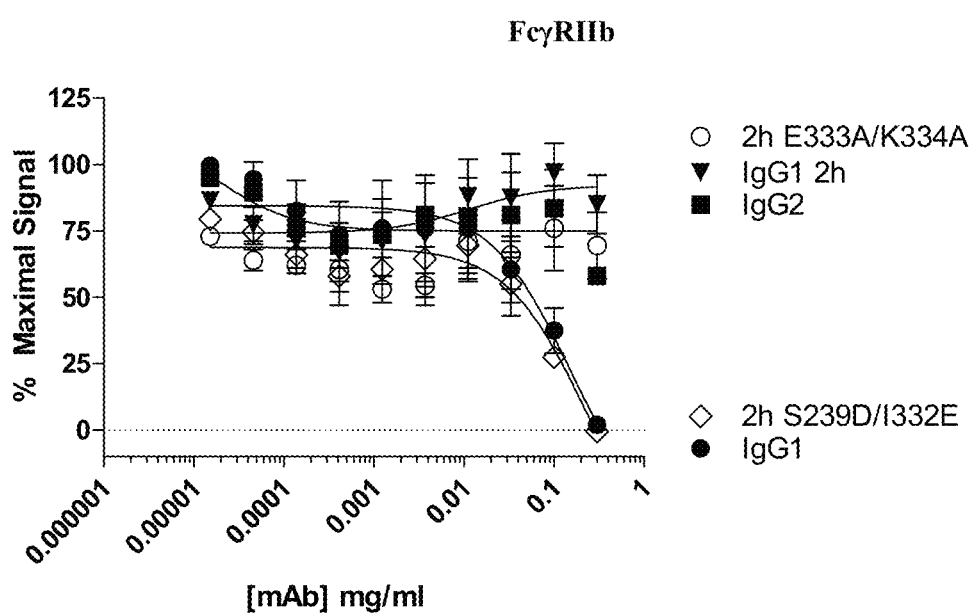
Figure 5E:
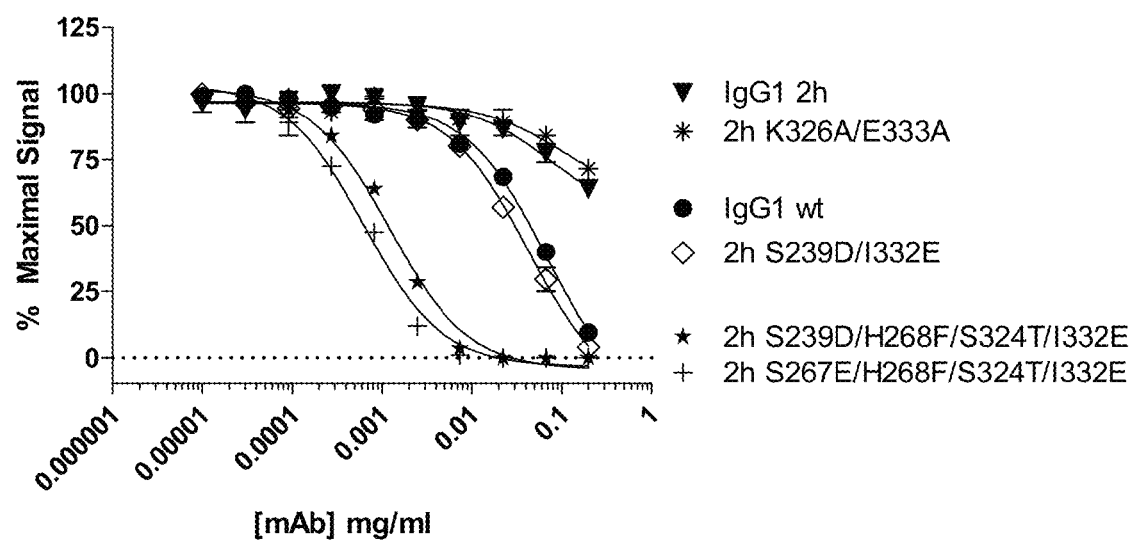
Figure 5F:
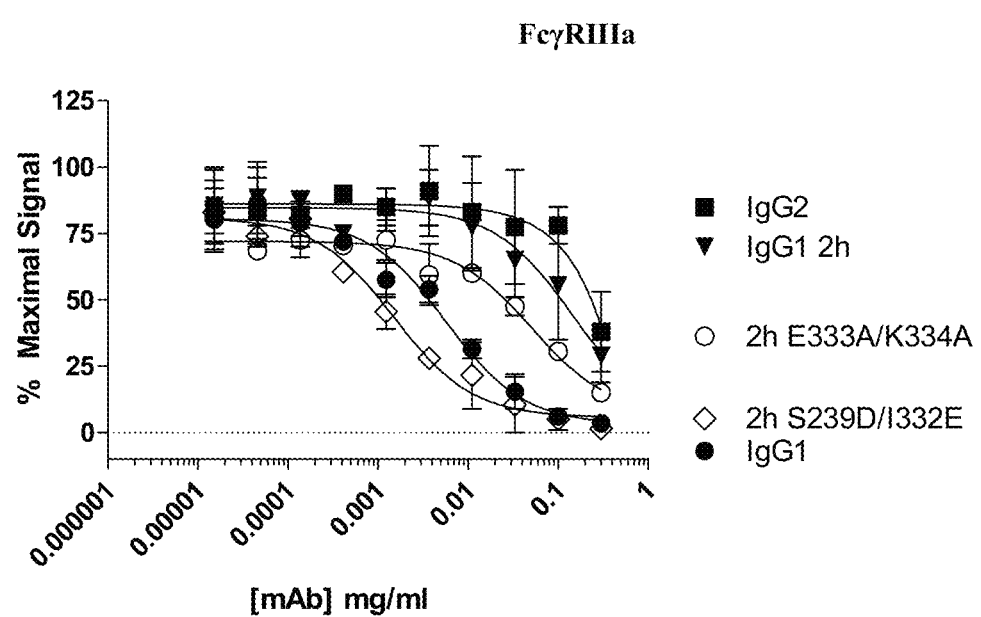

Additionally, the 2h S239D/H268F/S324T/I332E (9) construct displayed comparable binding to IgG1, whereas the 2h S267E/H268F/S324T/I332E (10) construct had increased binding to FcγRIIa compared to IgG1 wt (FIG. 5C). Both of the constructs 2h S239D/H268F/S324T/I332E (9) and 2h S267E/H268F/S324T/I332E (10) displayed increased binding to FcγRIIb relative to IgG1 wt (FIG. 5E). The construct 2h K326A/E333A (11) showed minimal detectable binding to both FcγRIIa (FIG. 5C) and FcγRIIb (FIG. 5E).

The construct 2h S267E/H268F/S324T/I332E (10) showed slightly decreased binding to FcγRIIIa compared to IgG1 wt, whereas the construct 2h S239D/H268F/S324T/I332E (9) had increased binding to FcγRIIIa (FIG. 5G). The 2h K326A/E333A (11) displayed weak binding to FcγRIIIa compared to IgG1 wt (FIG. 5G).

Summary

These results indicated that the proteolytic resistant constructs comprising 2h S239D/I332E (5), 2h S239D/H268F/S324T/I332E (9), and 2h S267E/H268F/S324T/I332E (10) were capable of binding to FcγRIIa, IIb, and IIIa to varying degrees, and all three of these constructs had increased binding relative to the 2h (4) mutation alone. The mutation of residues in the lower hinge of IgG1 combined with other CH2 mutations, which enhanced FcγRIIa binding affinity over IgG1 wt as with construct 2h S267E/H268F/S324T/I332E (10), enhanced affinity of 2h S239D/H268F/S324T/I332E (9) and 2h S267E/H268F/S324T/I332E (10) for FcγRIIb, enhanced FcγRIIIa binding affinity over IgG1 wt as with the constructs 2h S239D/I332E (5) and 2h S239D/

H268F/S324T/I332E (9) were an unexpected results because mutation of the lower hinge has been historically associated with a loss-of-function in terms of FcγR-binding. These results demonstrate, unexpectedly, that mutation of key lower hinge residues associated with interactions with FcγRs can be compensated for with mutations in the CH2 region, and that several of the compensating mutations can enhance FcγR-binding relative to an IgG1 wt.

Example 2. Antibody-Dependent Cellular Phagocytosis (ADCP)

In order to test the ability of the protease-resistant mAbs to mediate Fc-dependent in vitro cell killing, ADCP assays were performed. In this assay, phagocytic cells are recruited to the target antigen displaying cell by antibody binding and target cell destruction is measured.

Procedure

PBMCs were isolated from normal human donors using Ficoll gradient centrifugation. CD14pos monocytes were purified from PBMCs by negative depletion using a CD14 Isolation kit that did not deplete CD16pos monocytes (Stem Cell Technologies). Monocytes were plated at $0.1 \times 10^6$ cells/$cm^2$ in X-VIVO-10 medium (Lonza) containing 10% FBS and 20 ng/ml GM-CSF (R&D Systems) for 7 days. 100 ng/ml of IFNγ (R&D Systems) was added for the final 24 hours of differentiation. The target cells for the ADCP assay were GFP-expressing MDA-MB-231 cells. Isolated macrophages were incubated with GFP-expressing MDA-MB-231 at a ratio of 4:1 for 4 hours with or without wild type and protease-resistant mAb constructs in 96 well U-bottom plates. After incubation, cells were removed from the 96 well plates using Accutase (Sigma). Macrophages were identified with anti-CD11b and anti-CD14 antibodies (both from BD Biosciences) coupled to AlexaFluor 647 (Invitrogen), and then cells were acquired on a FACs Calibur (BD Biosciences). The data were analyzed using FloJo Software (Tree Star). The percent phagocytosis was determined by the following equation ((GFPpos, CD11bpos, CD14pos cells)/(GFPpos, CD11bpos, CD14pos cells plus GFPpos alone cells)×100%.

Isolated monocytes were differentiated in vitro using GM-CSF and IFNγ as described. As was shown by others, the differentiated macrophages expressed all of the FcγRs (FcγRI, FcγRIIa, FcγRIIb, and FcγRIIIa) (data not shown).

Results

Figure 6A:
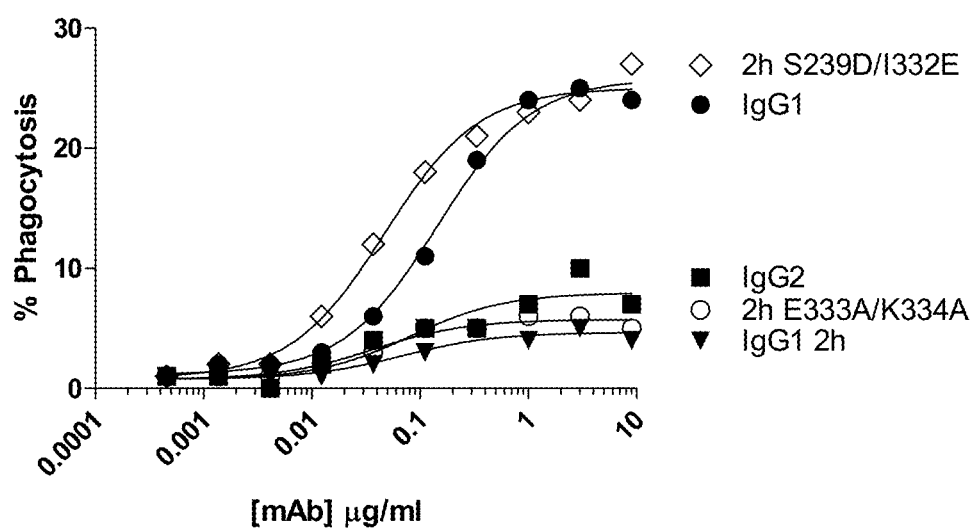
FIG. 6A-C are graphs from separate ADCP assays performed with protease-resistant mAb constructs and wildtype $IgG_1$ and $IgG_2$ where the % Phagocytosis on the Y-axis is relative to the total number of sampled cells.
Figure 6B:
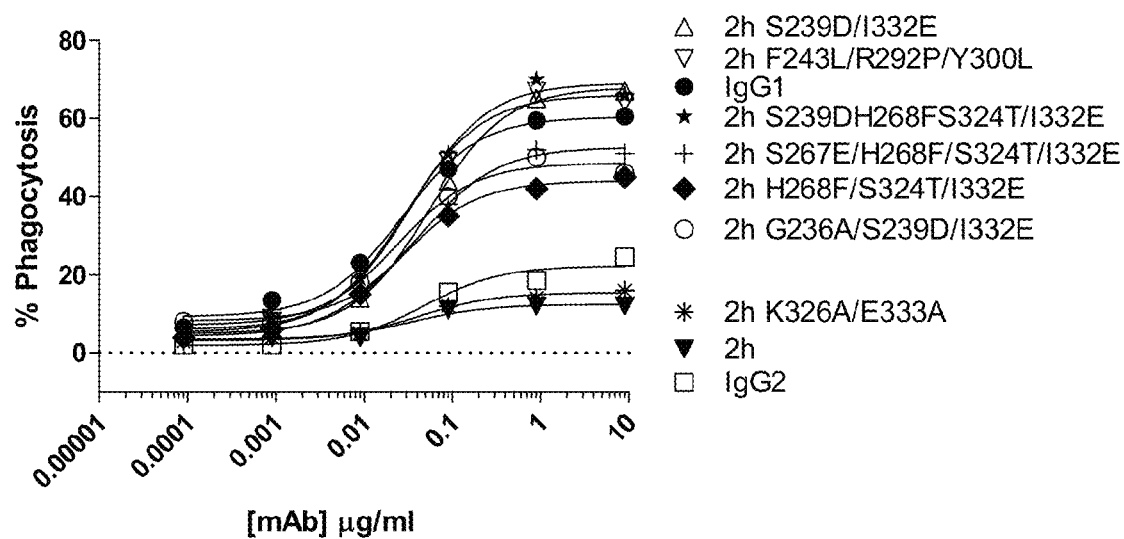
Figure 6C:
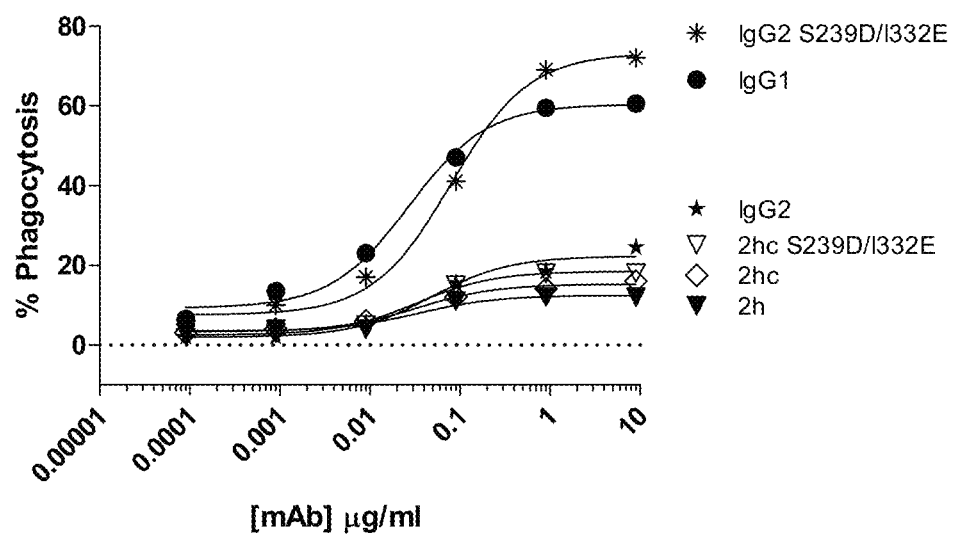

The data represented in FIG. 6A indicates that IgG1 wt (1) and 2h S239D/I332E (5) achieved the highest levels of ADCP. The ADCP capacity of IgG2 wt (2), IgG1 2h (4), and 2h E333A/K334A (6) produced low but detectable ADCP capacity. These results indicate that the protease-resistant construct 2h S239D/I332E (5) was capable of phagocytosing tumor cells at a level comparable to IgG1 wt. In a separate experiment, an additional panel of CH2 constructs containing the IgG1 2h hinge region were tested for ADCP capacity (FIG. 6B). In this group, the constructs 2h S239D/I332E (5), 2h F243L/R292P/Y300L (7), and 2h S239D/H268F/S324T/I332E (9) had similar ADCP as IgG1 wt (1), whereas the constructs 2h S267E/H268F/S324T/I332E (10), 2h H268F/S324T/I332E (8), and 2h G237A/S239D/I332E (12) had slightly decreased maximal phagocytosis relative to IgG1 wt. The constructs 2h K326A/E333A (11) had low but detectable ADCP, similar to IgG2 wt (2) and IgG1 2h (4). Finally, the constructs containing the complete hinge of IgG2 were tested for ADCP. The construct IgG2 S239D/I332E (14) displayed similar ADCP as IgG1 wt, whereas the constructs 2hc (3) and 2hc S239D/I332E (13) displayed low but detectable ADCP.

Example 3. Antibody-Dependent Cellular Cytotoxicity (ADCC)

In this assay, mononuclear cells are recruited to the target antigen displaying cell and target cell destruction is measured.

Procedure

ADCC assays were performed as previously described (Scallon et al., Mol Immunol 44:1524-1534 2007). Briefly, PBMCs were purified from human blood by Ficoll gradients and used as effector cells for ADCC assays. MDA-MB-231 human breast carcinoma cells (ATCC HTB-26) were used as target cells with a ratio of 1 target cell to 50 effector cells. Target cells were pre-labeled with BATDA (PerkinElmer) for 20 minutes at 37° C., washed twice and resuspended in DMEM, 10% heat-inactivated FBS, 2 mM L-glutamine (all from Invitrogen). Target ($1 \times 10^4$ cells) and effector cells ($0.5 \times 10^6$ cells) were combined and 100 μl of cells were added to the wells of 96-well U-bottom plates. An additional 100 μl was added with or without wild type and protease-resistant mAb constructs. All samples were performed in duplicate. The plates were centrifuged at 200 g for 3 minutes, incubated at 37° C. for 2 hours, and then centrifuged again at 200 g for 3 minutes. A total of 20 μl of supernatant was removed per well and cell lysis was measured by the addition of 200 μl of the DELPHIA Europium-based reagent (PerkinElmer). Fluorescence was measured using an Envision 2101 Multilabel Reader (PerkinElmer). Data were normalized to maximal cytotoxicity with 0.67% Triton X-100 (Sigma Aldrich) and minimal control determined by spontaneous release of BATDA from target cells in the absence of any antibody. Data were fit to a sigmoidal dose-response model using GraphPad Prism v5.

Results

Figure 7A:
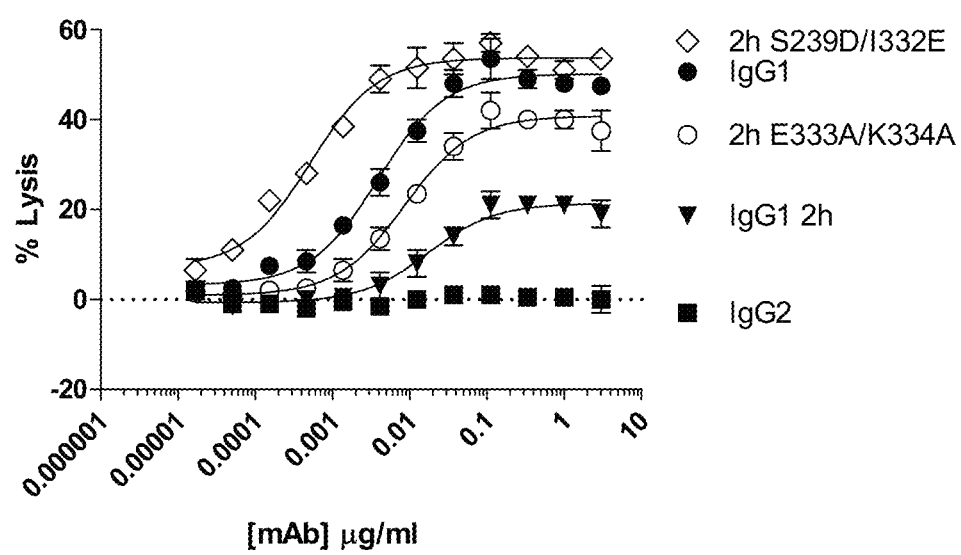
FIG. 7A-C are graphs from separate ADCC assays performed with protease-resistant mAb constructs and wildtype $IgG_1$ and $IgG_2$ where the % Lysis on the Y-axis is relative to 100% lysis of the same number of cells by detergent (n=2).

The data were plotted so that the level of cell lysis is represented on the Y-axis as a function of antibody concentration. The data shown in FIG. 7A indicate that 2h S239D/I332E (5) construct had the highest level of ADCC capacity which was approximately an 8-fold (as evidenced by the shift in apparent EC50) improvement over IgG1 wt in the depicted assay.

Figure 7B:
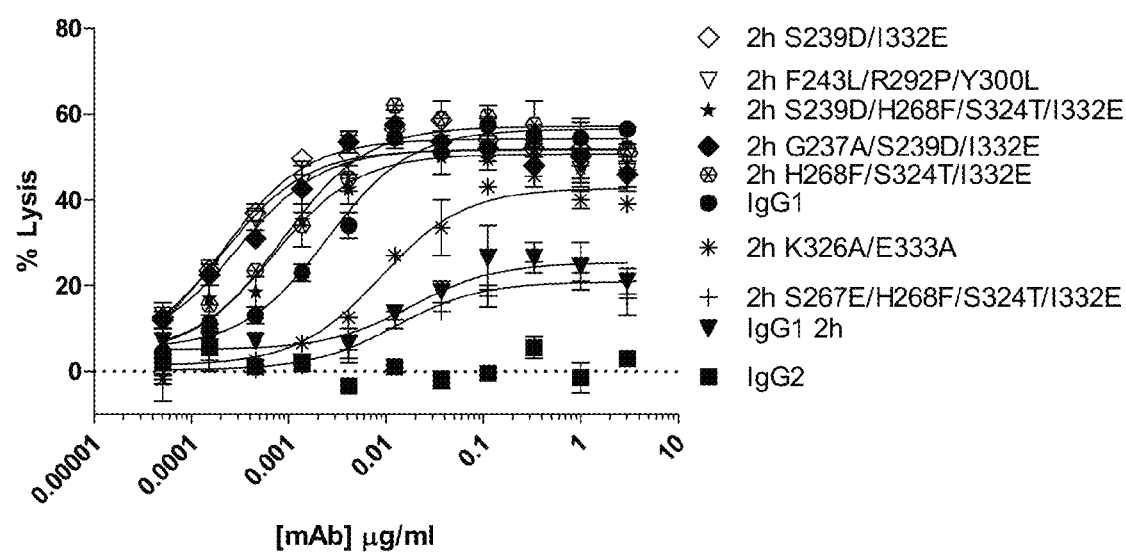
Figure 7C:
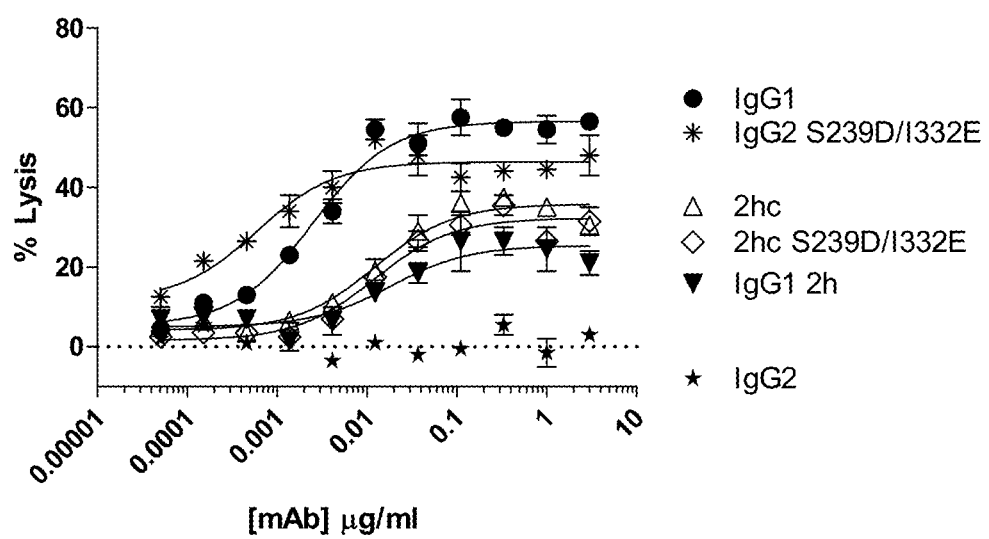

In another experiment, the ADCC capacity of an extended panel of constructs was compared. FIG. 7B depicts the curves generated by the data. Three constructs (2h S239D/I332E (5), 2h F243L/R292P/Y300L (7), and 2h S239D/H268F/S324T/I332E (9) had increased ADCC capacity relative to IgG1 wt. The 2h G237A/S239D/I332E (12) and 2h H268F/S324T/I332E (8) constructs had slightly increased ADCC over IgG1 wt, whereas the constructs 2h K326A/E333A (11) and 2h S267E/H268F/S324T/I332E (10) had detectable, but decreased ADCC relative to IgG1 wt. FIG. 7C depicts ADCC results from a panel of constructs that contained the complete hinge region of IgG2. The IgG2 S239D/I332E (14) construct had a lower EC50 than IgG1 wt, but also a lower maximal lysis. The constructs 2hc (3) and 2hc S239D/I332E (13) had detectable ADCC above IgG2 wt, but lower than IgG1 wt. Taken together, these results demonstrate that mutation of critical residues in the lower hinge can be compensated for to restore ADCC and FcγR-binding by a number of CH2 mutations. However, not all of the CH2 mutations made to the IgG1 2h (3) backbone tested were capable of restoring/enhancing ADCC relative to IgG1 wt.

These results were consistent with the FcγRIIIa binding assay (FIG. 5F-G) showing enhanced affinity of 2h S239D/I332E (5) and 2h S239D/H268F/S324T/I332E (9), because FcγRIIIa-expressing NK cells are thought to be the relevant effector cell in ADCC.

Example 4. Complement-Dependent Cytotoxicity (CDC)

Figure 8:
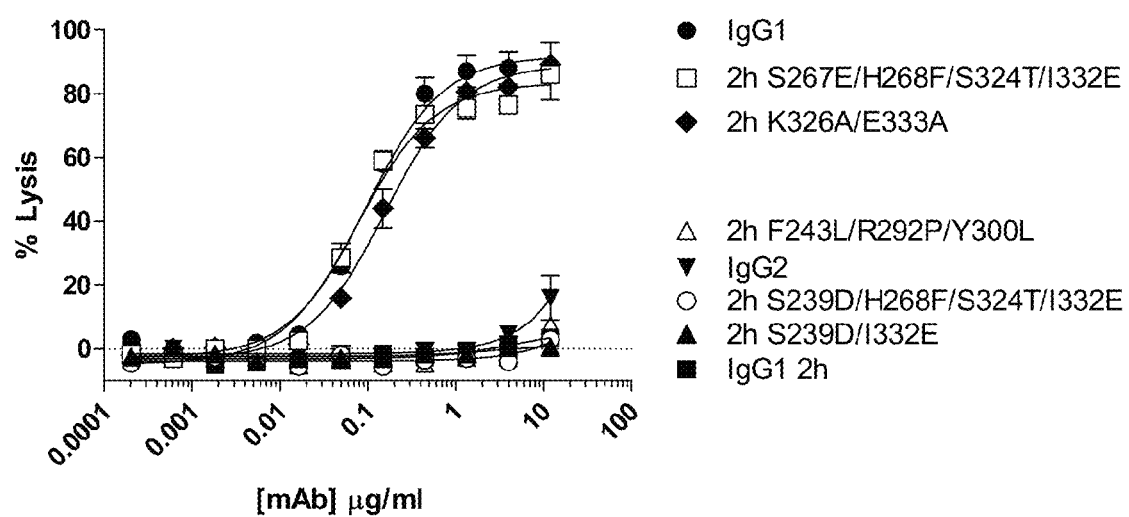
FIG. 8 is a graph from a CDC assay performed with protease-resistant mAb constructs and wildtype $IgG_1$ and $IgG_2$ where the % Lysis on the Y-axis is relative to 100% lysis of the same number of cells by detergent (n=2).

In this assay, complement components are recruited to the target antigen displaying cell and target cell destruction is measured.
Procedure
CDC assays were performed as previously described (Brerski et al. J Immunol. 181(5):3183-3192 2008). WIL2-S cells were used as target cells for CDC assays. 50 µl of cells were added to the wells of 96-well plates for a final concentration of $8\times10^4$ cells per well in RPMI, 5% heat-inactivated FBS, 0.1 mM nonessential amino acids, 1 mM sodium pyruvate (all from Invitrogen). An additional 50 µl was added to the wells with or without antibodies and the plates were incubated at room temperature for 2 hours. 50 µl of 10% rabbit complement (Invitrogen) was added to the wells and the plates were incubated for 20 minutes at 37° C. All samples were performed in duplicate. The plates were centrifuged at 200 g for 3 minutes and 50 µl of supernatant was removed to separate plates and CDC was measured with LDH cytotoxicity detection kit (Roche). Absorbance was measured using a Spectra max Plus 384 (PerkinElmer). Data were normalized to maximal cytotoxicity with Triton X-100 (Sigma Aldrich) and minimal control containing only cells and complement alone. Data were fit to a sigmoidal dose-response model using GraphPad Prism v5.
Results
The data shown in FIG. 8 indicate that the constructs 2h S267E/H268F/S324T/I332E (10) and 2h K326A/E333A (11) both achieved similar levels of cell lysis as IgG1 wt. The constructs IgG1 2h (4), 2h S239D/I332E (5), 2h F243L/R292P/Y300L (7), and 2h S239D/H268F/S324T/I332E (9) had minimal CDC capacity which was similar to that measured for IgG2 wt (2).

Example 5. Additional Protease-Resistant Constructs

Only two CH2 mutations, in combination with the E233P/L234V/L235A with G236 deleted, were capable of CDC activity comparable to IgG1 wt, namely 2h K326A/K334A (11) and 2h S267E/H268F/S324T/I332E (10). However, 2h K326A/K334A (11) had minimal ADCC and ADCP activity, and 2h S267E/H268F/S324T/I332E (10) had reduced ADCC activity relative to IgG1 wt. It would be beneficial to engineer protease-resistant constructs that have all three activities (ADCC, ADCP, and CDC). The H268F/S324T mutations alone were previously not shown to increase affinity to FcγRs (Moore et al.), whereas the construct 2h H268F/S324T/I332E had increased ADCC relative to 2h. Therefore, the I332E mutation alone may restore ADCC to the 2h protease-resistant hinge construct. Therefore, constructs will be generated that combine both ADCC/ADCP restoration with CDC restoration to the 2h parent hinge including 2h K326A/I332E/E333A (15) (SEQ ID NO: 18), S239D/K326A/E333A (SEQ ID NO: 19) (16), and S267E/I332E (17) (SEQ ID NO: 20).
The three constructs were tested using the materials and methods described in Example 1. The three constructs displayed resistance to MMP-3 and MMP-12 compared to IgG1 wt.

As was previously demonstrated, IgG2 wt (2) was resistant to GluV8, whereas IgG1 wt (1) had less than 60% intact IgG left after a 24 hour digestion. The three constructs had increased resistance to GluV8 compared to IgG1 wt. However, constructs 2h K326A/I332E/E333A (15) and 2h S267E/I332E (17) had decreased resistance to GluV8 compared to IgG2 wt, while 2h S239D/K326A/E333A (16) had resistance comparable to IgG2 wt. These data suggest that mutations which introduce an additional Glu into the CH2 in combination with the lower hinge mutation creates a novel GluV8 cleavage site (e.g. 2h S239D/I332E (5), 2h K326A/I332E/E333A (15) and 2h S267E/I332E (17)), whereas mutations that do not incorporate a Glu into the CH2 display resistance to GluV8 similar to IgG2 wt (e.g. 2h K326A/E333A (11) and 2h S239D/K326A/E333A (16)).

Both IgG1 wt and IgG2 wt were susceptible to proteolysis by IdeS. The two constructs 2h K326A/I332E/E333A (15) and 2h S267E/I332E (17) had greater than 90% intact IgG remaining after a 24 hour incubation with IdeS, whereas the construct 2h S239D/K326A/E333A (16) had less than 20% intact IgG remaining. These results suggest that the addition of a Glu into the CH2 in combination with the lower hinge mutation increases the protease-resistance to IdeS, a property which the lower hinge mutation alone, 2h (4), does not impart.

The three constructs were tested for their ability to perform ADCP, ADCC, and CDC. The three constructs had increased ADCP capacity compared to both IgG2 wt and 2h (4), but decreased maximum ADCP compared to IgG1 wt. Two of the constructs, 2h K326A/I332E/E333A (15) and 2h S239D/K326A/E333A (16) had slightly increased ADCC relative to IgG1 wt. The construct 2h S267E/I332E (17) had decreased ADCC relative to IgG1 wt, but increased ADCC relative to IgG2 wt and 2h (4). All three constructs had increased CDC capacity relative to IgG2 wt and 2h (4); however, the CDC for all three was slightly decreased relative to IgG1 wt.

Example 6. Summary of Beneficial Mutations

The following eleven Fc variants were shown to provide an antibody composition resistant to one or more proteases capable of cleaving IgG1 in the lower hinge while providing one or more effector functions exhibited by the wild-type human IgG1. The symbol 2h designates IgG1 with E233P/L234V/L235A-G236 deleted.

TABLE 5

| Construct | Abbreviation (#) |
| --- | --- |
| IgG1 2h S239D/I332E | 2h DE (5) |
| IgG1 2h F243L/R292P/Y300L | 2h LPL (7) |
| IgG1 2h H268F/S324T/I332E | 2h FTE (8) |
| IgG1 2h S239D/H268F/S324T/I332E | 2h DFTE (9) |
| IgG1 2h S267E/H268F/S324T/I332E | 2h EFTE (10) |
| IgG1 2h K326A/E333A | 2h AA (11) |
| IgG1 2h G237A/S239D/I332E | 2h XDE (12) |
| IgG2 S239D/I332E | IgG2 DE (14) |
| IgG1 2h K326A/I332E/E333A | 2h AEA (15) |
| IgG1 2h S239D/K326A/E333A | 2h DAA (16) |
| IgG1 2h S267E/I332E | 2h EE (17) |

Where sufficient data was available, EC50 values calculated when a cell killing was complete or near complete for the in vitro assays used as a proxy for various effector function is shown below. The data shown in Tables 6A and 6B were generated under identical conditions except that the donor PBMC source was different. Therefore, the fold change from the IgG1 wt (1) in each experiment is used to standardize the relative biological activity.

TABLE 6A

| Construct (#) | ADCC EC50 (ng/ml) | fold | ADCP EC50 (ng/ml) | fold | CDC EC50 (ng/ml) | fold |
|---|---|---|---|---|---|---|
| IgG1 wt (1) | 4.8 | 1 | 27 | 1 | 96 | 1 |
| 2h DE (5) | 0.53 | 9 | 54 | 0.5 | n/a | n/a |
| 2h G237A/DE (13) | 0.47 | 10 | 24 | 1.1 | n.d. | n.d. |
| 2h LPL (7) | 0.31 | 15 | 30 | 0.9 | n/a | n/a |
| 2h AA (11) | 21 | 0.2 | n/a | n/a | 157 | 0.6 |
| 2h DFTE (9) | 0.70 | 7 | 34 | 0.8 | n/a | n/a |
| 2h EFTE (10) | n/a | n/a | 44 | 0.6 | 77 | 1.2 |

TABLE 6B

| Construct (#) | ADCC EC50 (ng/ml) | fold | ADCP EC50 (ng/ml) | fold | CDC EC50 (ng/ml) | fold |
|---|---|---|---|---|---|---|
| IgG1 wt | 0.42 | 1 | 186 | 1 | 114 | 1 |
| 2h AEA (15) | 0.17 | 2.5 | 44* | 4.2 | 202 | 0.56 |
| 2h DAA (16) | 0.14 | 3.4 | 42* | 4.4 | 308 | 0.37 |
| 2h EE (17) | 5.6 | 0.08 | 52* | 3.6 | 592 | 0.19 | n/a = not applicable (insufficient binding curve data to determine EC50),
*submaximal lysis achieved
n.d. = no data
fold = EC50 IgG1 wt/EC50 construct The effect on ADCC and ACDP of an additional modification at G237 in the lower hinge in addition to S239D/I332E and 233PVA/236, was examined using constructs listed in the Table 7 below. The G237A construct was tested and found to have resistance to MMPs, IdeS, and GluV8. The other constructs were not evaluated in the digestion assays. These data indicate that Ala (A) and Ser (S) are tolerated at 237 but do not increase the cytolytic activity of the Fc above that displayed by the parent molecule, 2h DE (5).

TABLE 7

| Construct | ADCC | ADCP |
|---|---|---|
| IgG1 2h DE | ++++++ | +++++ |
| IgG1 2h ADE | ++++++ | ++++ |
| IgG1 2h DDE | + | + |
| IgG1 2h PDE | ++ | + |
| IgG1 2h QDE | + | + |
| IgG1 2h SDE | +++++ | ++ |

A summary of the combined relative protease resistance (PR) to specific physiologically relevant proteases and the in vitro results for proxy assays indicating potential effector function (ADCC, ADCP, and CDC) are shown in Table 8 below where those constructs with combined protease resistance and one or more demonstrable effector activities are indicated in bold.

TABLE 8

| Isotype/ Construct | PR MMPs | PR IdeS | PR GluV8 | ADCC | ADCP | CDC |
|---|---|---|---|---|---|---|
| IgG1 wt (1) | − | − | + | +++++ | +++++ | +++++ |
| IgG2 wt (2) | +++++ | − | +++++ | − | ++ | − |
| IgG1 2hc (3) | +++++ | − | +++++ | + | ++ | n.d. |
| IgG1 2hc DE (13) | +++++ | − | +++++ | + | ++ | n.d. |

TABLE 8-continued

| Isotype/ Construct | PR MMPs | PR IdeS | PR GluV8 | ADCC | ADCP | CDC |
|---|---|---|---|---|---|---|
| IgG1 2h (4) | +++++ | − | +++++ | + | ++ | − |
| IgG1 2h DE (5) | +++++ | ++++ | ++ | ++++++ | +++++ | − |
| IgG1 2h LPL (7) | +++++ | ++++ | ++ | ++++++ | +++++ | − |
| IgG1 2h FTE (8) | +++++ | ++++ | +++++ | ++++++ | +++ | − |
| IgG1 2h DFTE (9) | +++++ | +++++ | ++++ | ++++++ | +++++ | − |
| IgG1 2h EFTE (10) | +++++ | ++++ | ++++ | + | ++++ | +++++ |
| 2h AA (11) | +++++ | − | +++++ | +++ | ++ | +++++ |
| 2h ADE (12) | +++++ | ++++ | ++ | ++++++ | ++++ | n.d. |
| IgG2 DE (14) | +++++ | +++ | ++ | ++++++ | ++++ | n.d. |
| 2h AEA (15) | ++++ | +++++ | +++ | ++++++ | +++ | ++++ |
| 2h DAA (16) | ++++ | + | +++++ | +++++ | +++ | ++++ |
| 2h EE (17) | ++++ | +++++ | +++ | + | +++ | ++++ |

Summary of Results

The study of Fc constructs presented herein demonstrated that substitution of residues EU 233-236 with PVA/, the sites where proteases were shown to cleave the IgG1 molecule, produced an Fc that was resistant to MMP-3, MMP-12, and GluV8; proteases that cleave between residues 232 and 234 (FIG. 1). When combined with these substitutions, additional modifications produced resistance to the *Staphylococcus* protease IdeS whether the residue positions substituted include a modification at the presumed cleavage site (EU236-237) or at a more distal position.

Substitution of the residues EU 233-236 with PVA/(2h, construct 4) alone resulted in the loss of cytolytic functions measureable by the in vitro assays described for ADCC, ADCP, and CDC. With respect to the combination of IgG1 Fc modifications previously reported to enhance one or more effector functions (Table 2) with the lower hinge PVA/ substitution, unexpectedly restored one or more aspects of in vitro cytolytic activity. Thus, no single construct was both protease-resistant and had measurable or enhanced activity for all three effector functions as measured by in vitro cell killing or cell lysis assays for ADCC, ADCP, and CDC.

1. Eight constructs had protease-resistance and enhanced or comparable ADCC compared to IgG1 wt: 5, 7, 8, 9, 12, 14, 15, and 16. Six of these incorporate the I332E substitution: including IgG1 2h DE (5), IgG1 2h FTE (8), IgG1 2h DFTE (9), IgG1 2h ADE (12), IgG2 DE (14) and IgG1 2h AEA (15).

2. Three PR constructs had similar ADCP compared to IgG1 wt including IgG1 2h DE (5), IgG1 2h LPL (7), and IgG1 2h DFTE (9). Three constructs had slightly reduced ADCP compared to IgG1 including IgG1 2h FTE (8), IgG1 2h EFTE (10), IgG1 2h ADE (12), and IgG2 DE (14).

3. Five PR mutations restored CDC capacity, IgG1 2h AA (11), IgG 2h EFTE (10), 2h AEA (15), 2h DAA (16), and 2h EE (17). In addition, all five had detectable, but reduced ADCP compared to IgG1 wt. Two variants, 2h AEA (15), 2h DAA (16), also had enhance ADCC as compared to IgG1 wt (1).

Two constructs (8 and 9) comprising H268F/S324T mutations did not have restored CDC when a protease-resistant hinge was present. The S267E mutation (EFTE (10)) restored CDC but decreased FcγRIIIa binding (also noted by Moore et al. mAbs 2010 2(2):181.) The S267E mutation increased affinity to FcγRIIb.

Example 7: Macrophage IL-10 Secretion and Tumor Killing at 24 Hours

In order to assess the effect of protease-resistant mAbs on macrophage IL-10 secretion, MDA-MB-231 cells were opsonized with protease-resistant mAbs and were then co-incubated with macrophages for 24 hours. At the end of the incubation, supernatants were collected for IL-10 quantification, and the percentage of tumor-cell killing was assessed by flow cytometry. All tested antibodies had variable region binding to CD142 (tissue factor).

Methods

Macrophages were differentiated from monocytes purified from PBMCs as described in Example 2 except that 25 ng/ml of M-CSF (R&D Systems) was used in place of GM-CSF, and 50 ng/ml of IFNγ (R&D Systems) was added for the final 24 hours of differentiation. The target cells for the assay were GFP-expressing MDA-MB-231 cells. Isolated macrophages were incubated in a 37° C. incubator with GFP-expressing MDA-MB-231 at a ratio of 4 macrophages ($0.1\times10^6$ cells/well) to 1 MDA-MB-231 cell (25,000 cells/well) for 24 hours with wild type or protease-resistant mAb constructs (5 μg/ml, 0.5 μg/ml or 0.0005 μg/ml) in 96 well U-bottom plates. The final volume of medium (DMEM+10% FBS) used for the assay was 200 μl. At the end of 24 hours, supernatants were collected and the IL-10 concentrations were determined using the human IL-10 Quantikine kit (R&D Systems) per the manufacturer's instructions. After the supernatants were harvested, the cells were removed from the 96-well plates using Accutase (Sigma). Macrophages were identified with anti-CD11b and anti-CD14 antibodies (both from BD Biosciences) coupled to Alexa Fluor 647 (Invitrogen), and then cells were acquired on an LSRFortessa flow cytometer (BD Biosciences). The data were analyzed using FloJo Software (Tree Star).

In a 24 hour ADCP assay, the percent (%) of cell-killing can be determined by measuring the reduction in GFP fluorescence resulting from its degradation in the lysosomes after internalization. The percent tumor cell killing in a 24 hour assay was determined by the following equation % tumor cells killed:((no mAb GFPpos,CD11bneg, CD14neg cells)−(with mAb GFPpos,CD11bneg, CD14neg cells))/(no mAb GFPpos,CD11bneg, CD14neg cells)×100%

Figure 9:
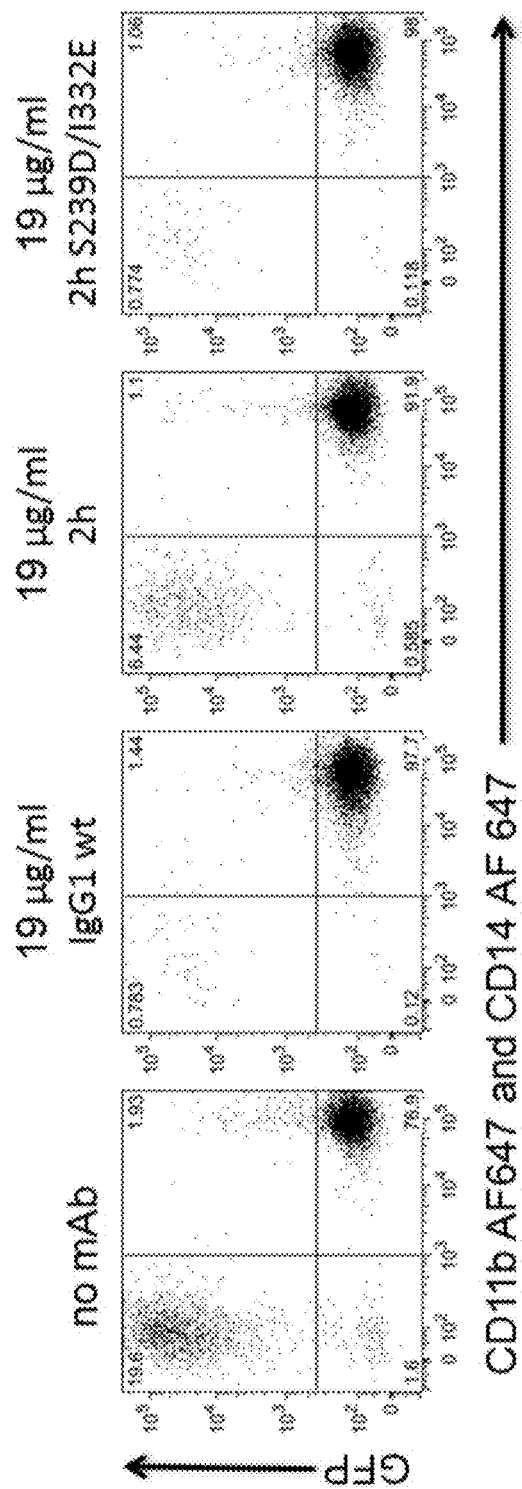
FIG. 9 is a FACS analysis of a 24 hour ADCP assay depicting GFP-expressing MDA-MB-231 as a frequency of GFPpos, CD11bneg, CD14neg cells (upper left quadrant) incubated for 24 hours in the absence or presence of shown mAbs and macrophages to measure % cell tumor killing.

An example of the methodology for calculating tumor cell-killing is depicted in FIG. 9. For example, IgG1 wt mAb induced 95% of tumor cell killing, (((19.6−0.783)/19.6)×100%), constructs 2h (4) 67%, and 2h S239D/I332E (5) 96%.

Results

Figure 10:
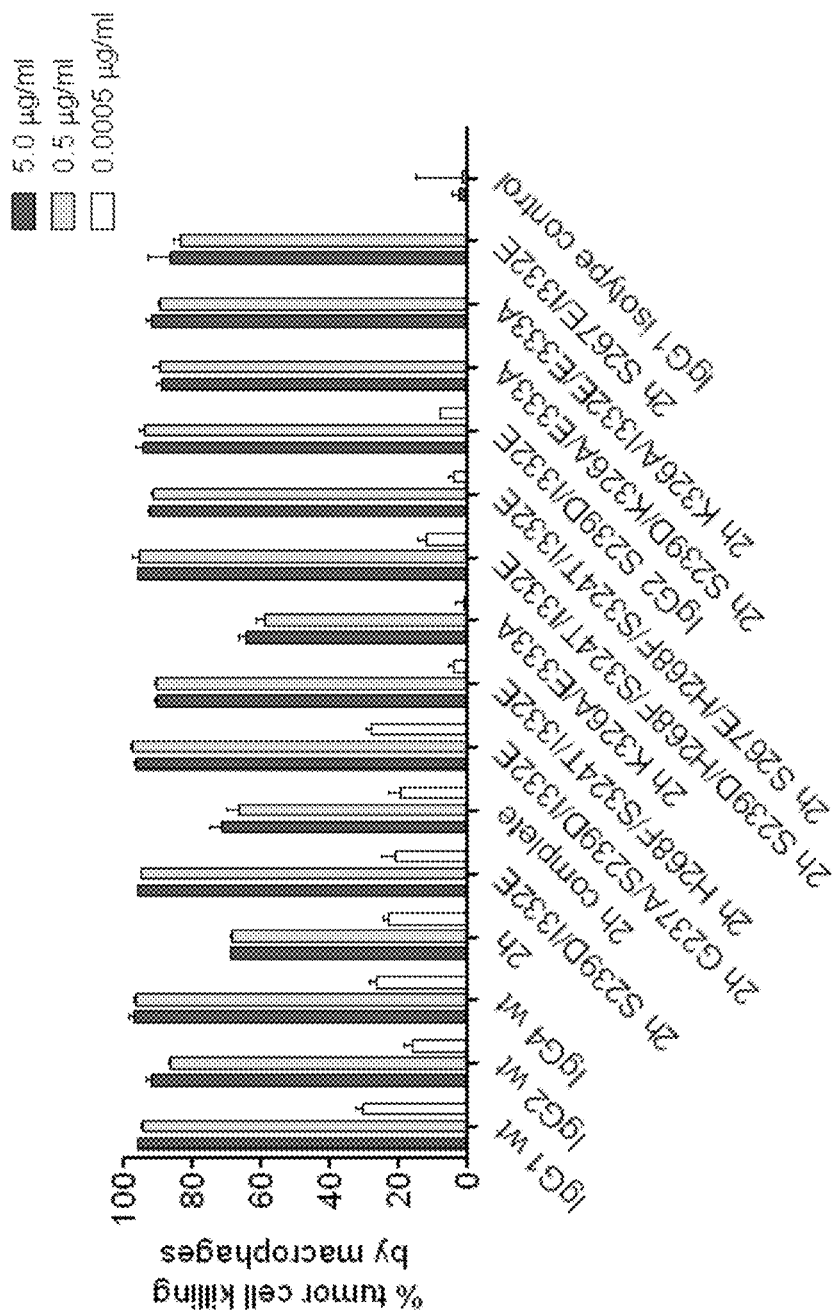
FIG. 10 shows % tumor cell killing in a 24 hour ADCP assay performed with protease-resistant mAb constructs and wild type IgG1, IgG2, and IgG4 as indicated at various antibody concentrations. Error bars indicate standard deviation.

FIG. 10 shows the effect of antibodies on tumor killing. IgG1 wt (1), IgG2 wt (2), IgG4 wt (18), 2h S239D/I332E (5), 2h G237A/S239D/I332E (12), 2h F268F/S324T/I332E (8), 2h S239D/H268F/S324T/I332E (9), 2h S267E/H268F/S234T/I332E (10), IgG2 S239D/I332E (14), 2h S239D/K326A/E333A (16), 2h K326A/I332E/E333A (15), and 2h S267E/I332E (17) all displayed a level of tumor cell-killing at or above 90% at antibody concentrations 5 μg/ml and 0.5 μg/ml. The constructs 2h (4), 2h complete (3), and 2h K326A/E333A (11) had slightly lower level or tumor cell-killing, about between 60-75%. The IgG1 isotype control mAb did not display detectable tumor cell-killing, demonstrating that tumor cell-killing was target specific.

Figure 11A:
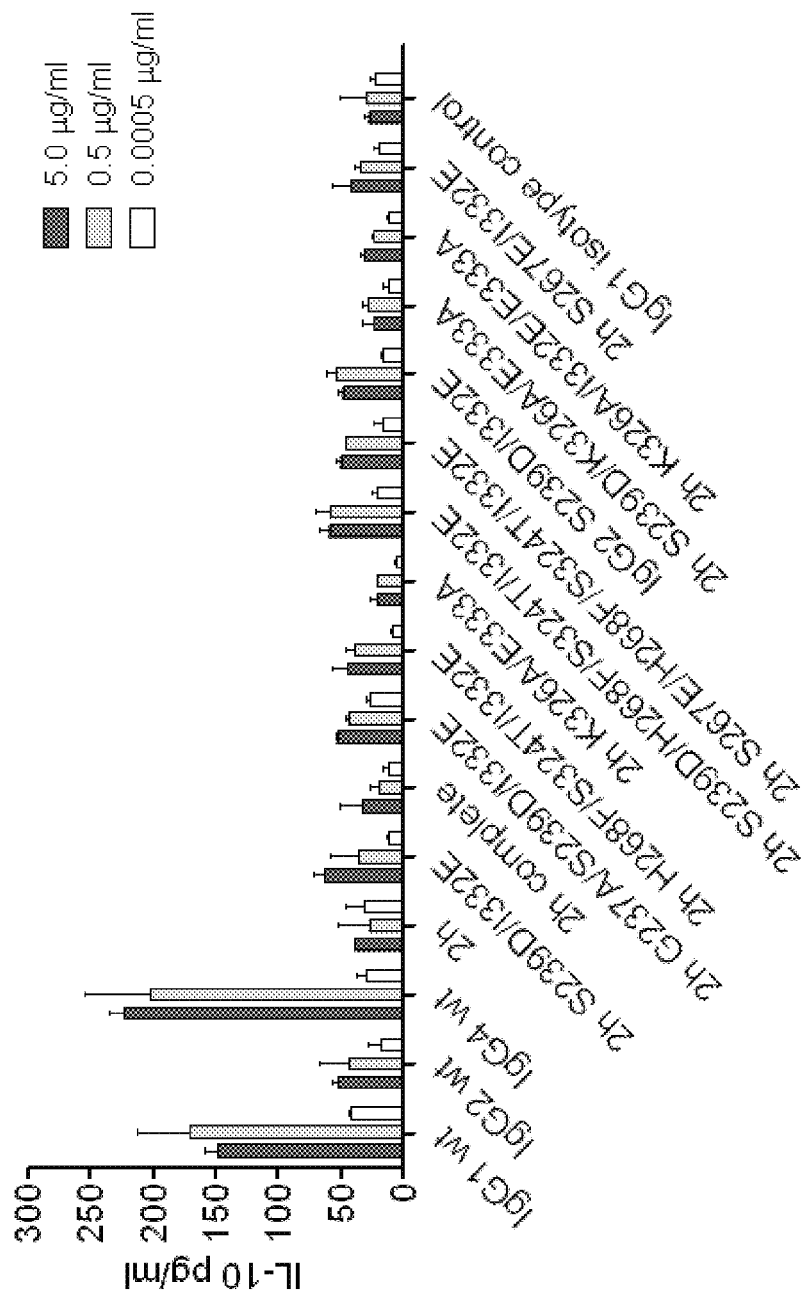
FIG. 11A-B shows A) concentration of IL-10 in pg/ml and B) fold change in IL-10 release detected in supernatants collected after a 24 hour incubation of macrophages and MDA-MB-231 cells with protease-resistant mAb constructs and wild type IgG1, IgG2, and IgG4. (n=2).
Figure 11B:
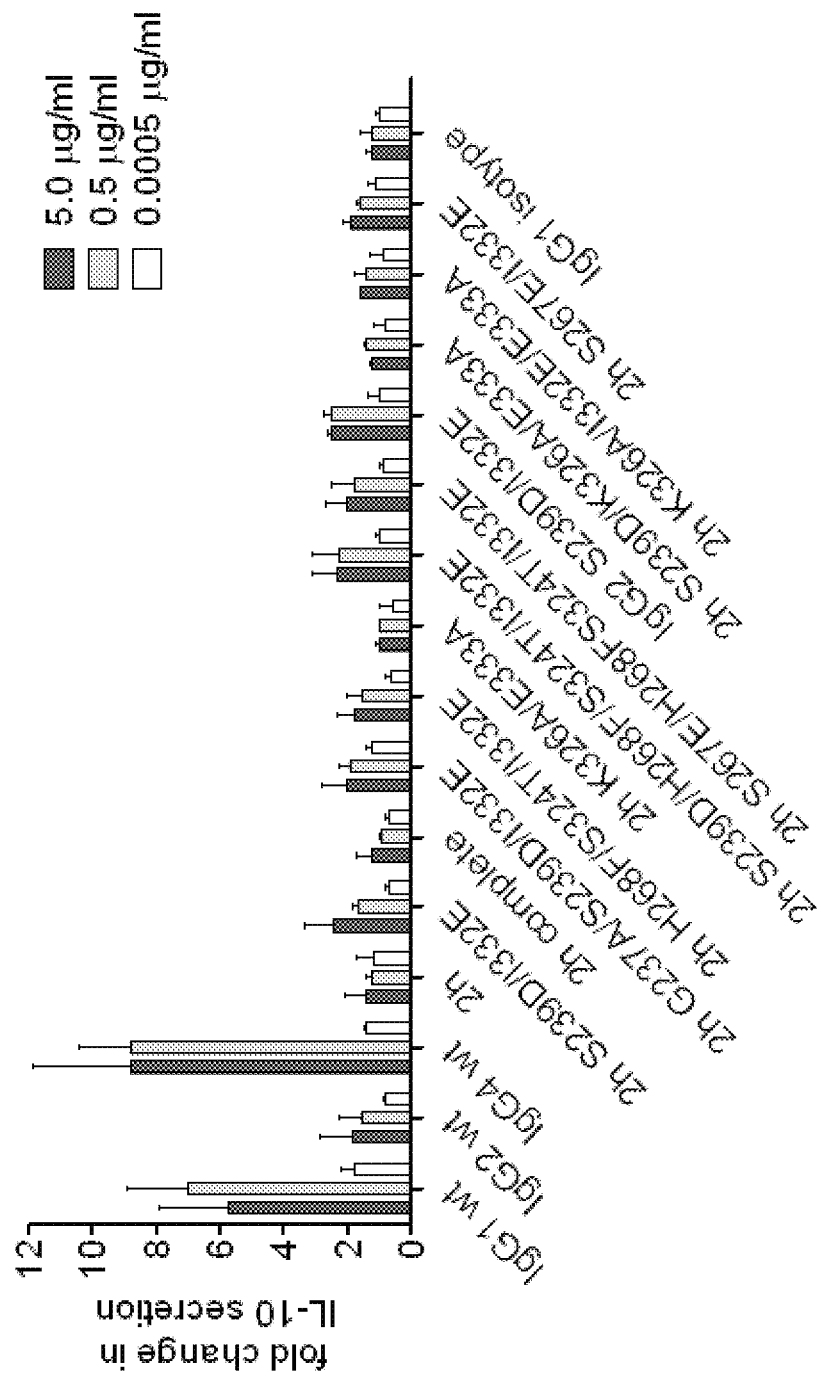

The macrophage IL-10 release from supernatants taken from the same experiment detailed above is shown in FIG. 11A. The two constructs IgG1 wt (1) and IgG4 wt (18) had a several fold increase in IL-10 release after 24 hours with peak IL-10 concentrations greater than or equal to 150 pg/ml. The amount of macrophage IL-10 release detected in this experiment for a tumor-targeting IgG1 wt mAb was similar to levels reported by others (Pander et al., Clin Cancer Res 17(17):5668-73 2011). All other constructs that were tested had several fold lower IL-10 release with peak IL-10 concentrations less than or equal to 60 pg/ml. FIG. 11B depicts the average fold increase in IL-10 release from two independent experiments relative to the amount of IL-10 detected when MDA-MB-231 cells and macrophages were co-cultured in the absence of tumor-targeting mAb. The IgG1 wt construct (1) displayed about a 6-fold increase in IL-10 secretion at mAb concentrations of 5.0 μg/ml and 0.5 μg/ml, respectively, whereas the IgG4 wt construct (18) displayed an 8-fold increase in IL-10 secretion at those same mAb concentrations. The constructs 2h (4), 2h complete (3), 2h K326A/E333A (11), and 2h S239D/K326A/E333A (16) did not show any appreciable increase in IL-10 secretion at any concentration tested (less than or equal to 1.5 fold increase). The constructs 2h S239D/I332E (5), 2h G237A/S239D/I332E (12), H268F/S324T/I332E (8), 2h S239D/H268F/S324T/I332E (9), 2h S267E/H268F/S234T/I332E (10), IgG2 S239D/I332E (14), 2h K326A/I332E/E333A (15), and 2h S267E/I332E (17) all displayed a roughly two-fold increase in IL-10 secretion relative to MDA-MB-231 cells and PBMCs incubated in the absence of mAb.

Consistent with the observation of others, macrophage engagement of a wild type IgG1 opsonized tumor cell resulted in the destruction of the tumor cell and a subsequent release of IL-10, which is indicative of a conversion of the macrophage into an anti-inflammatory regulatory phenotype implicated as a mechanism for potential lack of efficacy of the anti-cancer therapeutics. In contrast, most of the protease resistant mAbs had the ability to elicit macrophage killing of protease resistant mAb opsonized tumor cells, but the macrophages did not subsequently release IL-10. This suggests that these mAbs could induce ADCP without converting the macrophage into a regulatory phenotype. All of the constructs tested displayed at least 60% level of tumor cell killing in the assay using 0.5 μg/ml antibody, and most construct at least 90% level of tumor cell killing, with the exception of the IgG1 wt isotype control. However, only the IgG1 wt (1) and IgG4 wt (18) constructs displayed a several fold increase in IL-10 secretion.

Example 8. IFNγ Release after Co-Incubation of PBMCs with mAb Opsonized MDA-MB-231 Cells In order to assess the ability of protease-resistant mAbs to elicit PBMC IFNγ secretion, MDA-MB-231 cells were opsonized with protease-resistant mAbs (all with variable regions targeting CD142) and were then co-incubated with PBMCs for 48 hours. At the end of the 48 hour incubation, the supernatants were collected and the amount of IFNγ was quantified. All tested antibodies had variable regions that bind CD142 (tissue factor).

Methods

PBMCs were isolated from leukopacks obtained from normal human donors using Ficoll gradient centrifugation. Prior to the start of the assay, PBMCs were rested overnight at approximately $10\times10^6$ cells per 10 mls of X-VIVO-10 (Lonza)+10% FBS. MDA-MB-231 cells were plated in the wells of a 96-well U-bottom plate at a final concentration of 20,000 cells per well. MAbs were added to the MDA-MB-231 cells, and then incubated for 1 hour at 4° C. PBMCS were then added to the wells of the plate at a final concentration of 200,000 cells per well to give a ratio of 10 PBMCs per 1 MDA-MB-231 cell. The final volume of medium (DMEM+10%) used for the assay was 200 μl. The plates were then incubated in a 37° C. incubator for 48 hours. At the end of the incubation, the supernatants were harvested, and the IFNγ concentration was determined using the human IFNγ Quantikine kit (R&D Systems).

Results

Figure 12A:
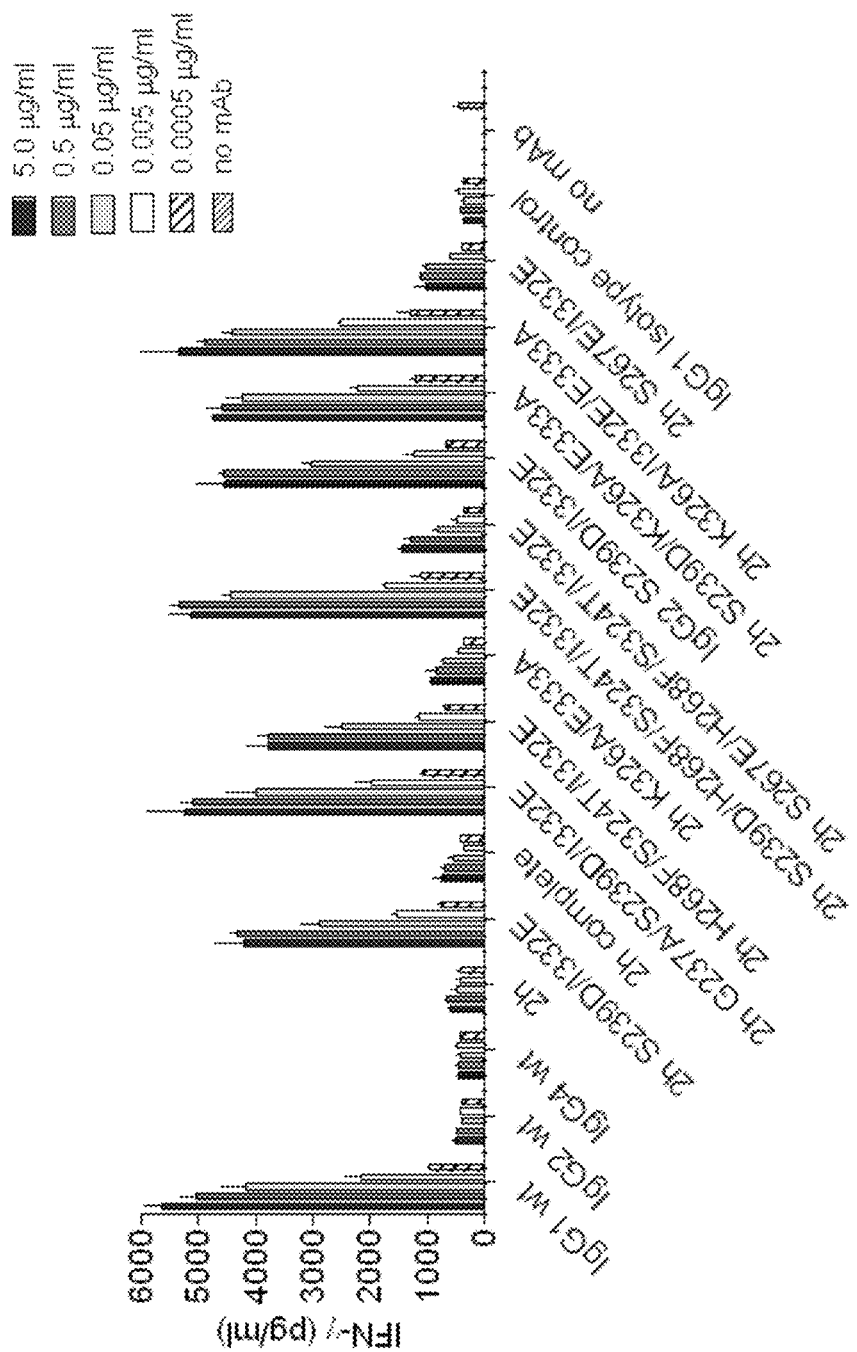
FIG. 12A-B shows A) concentration of IFNγ in pg/ml and B) fold change in IFNγ release detected in supernatants collected after a 24 hour incubation of PBMCs and MDA- MB-231 cells with protease-resistant mAb constructs and wild type IgG1, IgG2, and IgG4. (n=2).
Figure 12B:
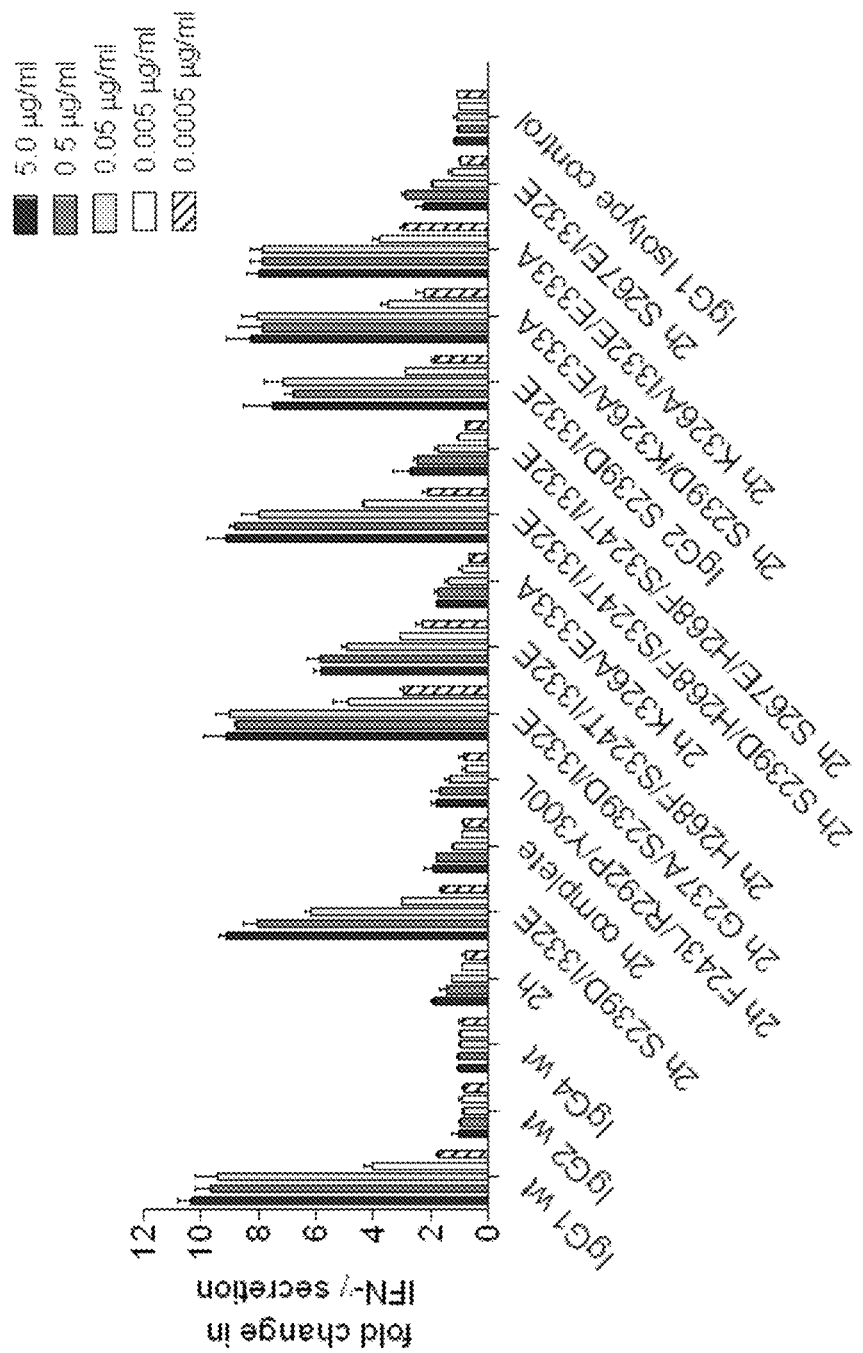

Co-incubation of MDA-MB-231 cells with PBMCs resulted in release of approximately 450 pg/ml of IFNγ (FIG. 12A). Eight constructs elicited greater than 3500 pg/ml IFNγ release, including IgG1 wt (1), 2h S239D/I332E (5), 2h G237A/S239D/I332E (12), 2h H268F/S324T/I332E (8), 2h S239D/H268F/S324T/I332E (9), IgG2 S239D/I332E (14), 2h S239D/K326A/E333A (16), and 2h K326A/I332E/E333A (15). The constructs IgG2 wt (2), IgG4 wt (18), 2h (4), and the IgG1 wt isotype control did not appear to have a mAb concentration-dependent increase in IFNγ, whereas the constructs 2h complete (3), 2h K326A/E333A (11), 2h S267E/H268F/S234T/I332E (10), and 2h S267E/I332E (17) all displayed a detectable increase in IFNγ secretion, but the maximum levels did not exceed 1500 pg/ml. FIG. 12B depicts the average fold increase in IFNγ release from two independent experiments relative to the amount of IFNγ detected when MDA-MB-231 cells and PBMCs were co-cultured in the absence of tumor-targeting mAb. The observed trend was similar to that described above with concentrations of IFNγ. The constructs IgG1 wt (1), 2h S239D/I332E (5), 2h G237A/S239D/I332E (12), 2h S239D/H268F/S324T/I332E (9), IgG2 S239D/I332E (14), 2h S239D/K326A/E333A (16), and 2h K326A/I332E/E333A (15) all displayed a greater than or equal to 8-fold increase in IFNγ secretion, and the construct 2h F268F/S324T/I332E (8) displayed an approximately 7-fold increase. The constructs IgG2 wt (2), IgG4 wt (18), 2h (4), and the IgG1 wt isotype control did not appear to elicit any mAb concentration-dependent increase of IFNγ. The constructs 2h complete (3) and 2h K326A/E333A (11) had a less than or equal to 2-fold increase in IFNγ, and the constructs 2h S267E/H268F/S234T/I332E (10) and 2h S267E/I332E (17) had a less than or equal to 3-fold increase in IFNγ.

These results indicated that the ability of mAbs to elicit IFNγ from PBMCs was independent from the ability of the same mAbs to elicit IL-10 from macrophages. Eight of the constructs induced a greater than or equal to 7-fold mAb concentration-dependent IFNγ secretion.

Example 9. Fc Gamma Receptor Binding as Assessed by ALPHASCREEN® Competition Binding Assays The ability of a tumor-targeting antibody to elicit antibody-dependent cytokine release (ADCR) appears to depend on which particular FcγRs an individual mAb can bind to. Therefore, the FcγR-binding of all of the constructs used in the ADCR assays were assessed by competition ALPHASCREEN® assays as described in Example 1. The IC50 values for each construct were determined from the non-linear regression analysis, and the results for each FcγR tested are summarized in FIG. 13. The fold change=IC50 [IgG1 wt]/IC50 [variant].

Summary of characteristics of protease-resistant mAb is shown in FIG. 14. In the Figure, 24 h ADCP is scored as follows: −: 0-20%, +: 20-40%, ++: 40-60%, +++: 60-80%, ++++: 80-100% ADCP when compared to ADCP induced by IgG1. Macrophage IL-10 release is scored as follows: −: 1-2, +: 2-3, ++: 3-4, +++: 4-5, ++++: 5-6, +++++6 and over fold change over sample having no mAb added. PBMC IFNγ release is scored as follows: −: 1-2, +: 2-4, ++: 4-6, +++: 6-8, ++++: 8-10, +++++10 and over fold change; all characteristics scored at highest mAb concentration tested. Upon additional testing, construct 2h S239D/I332E (5) was found not to bind FcγRI (see Table 3).

What is claimed is:

1. A method for treating cancer, comprising administering a therapeutically effective amount of an isolated antibody comprising a modified Fc-containing molecule comprising a wild type human IgG1 Fc region of SEQ ID NO: 1 comprising a hinge, a CH2 domain and a CH3 domain, wherein
a) the sequence of E233-L234-L235-G236 in the hinge is replaced with P233-V234-A235 with G236 deleted; and
b) the CH2 domain comprises at least one substitution selected from the group consisting of S239D/I332E, K326A/E333A, H268F/S324T/I332E, F243L/R292P/Y300L, S239D/H268F/S324T/I332E, S267E/H268F/S324T/I332E, K326A/I332E/E333A, S239D/K326A/E333A, S267E/I332E and G237X/S239D/I332E where X is A, D, P, Q or S; wherein amino acid residues are numbered according to EU numbering to a patient in need thereof to treat the cancer.

2. The method of claim 1, wherein the antibody is resistant to proteolytic degradation by a protease that cleaves the wild type human IgG1 molecule between or at residues 222-237.

3. The method of claim 2, wherein the antibody is capable of promoting antibody-dependent cellular phagocytosis (ADCP) measured in the presence of CD14 positive and/or CD11b positive human monocyte-derived macrophages, is capable of promoting antibody-dependent cell-mediated cytotoxicity (ADCC) measured in the presence of blood mononuclear cells, or is capable of promoting complement-dependent cytotoxicity (CDC) measured by cell lysis in the presence of complement.

4. The method of claim 3, wherein the antibody is capable of promoting antibody-dependent cellular phagocytosis (ADCP) measured in the presence of CD14 positive and/or CD11b positive human monocyte-derived macrophages, is capable of promoting antibody-dependent cell-mediated cytotoxicity (ADCC) measured in the presence of blood mononuclear cells, and is capable of promoting complement-dependent cytotoxicity (CDC) measured by cell lysis in the presence of complement.

5. The method of claim 3 or 4, wherein the antibody induces IL-10 secretion by human monocyte-derived macrophages by about no more than three times more when compared to the IL-10 secretion by the human monocyte-derived macrophages in the absence of the isolated antibody.

6. The method of claim 4, wherein the antibody has an $IC_{50}$ fold change ratio value of 0.04 or less measured in a competition assay with biotinylated human IgG1 to 0.2 µg/ml soluble human FcγRI, wherein the $IC_{50}$ fold change ratio is a ratio of an $IC_{50}$ value for a wild type human IgG1 to an $IC_{50}$ value for the isolated antibody of claim 1.

7. The method of claim 5, wherein the antibody at a concentration of 0.5 µg/ml induces interferon-gamma (IFNγ) secretion by pheripheral blood mononuclear cells (PBMCs) by at least three times more when compared to the IFNγ secretion by the PBMCs in the absence of the isolated antibody.

8. The method of claim 2, wherein the protease that cleaves the wild type IgG1 molecule between or at residues 222-237 is matrix metalloprotease (MMP) 2 (MMP-2), MMP-3, MMP-7, MMP-9, MMP-12, MMP-13, immunoglobulin degrading enzyme from Strep. Pyrongenes (IdeS), or glutamyl endopeptidase I from Staph. aureus (GluV8), human neutrophil elastase (HNE), plasmin, cathepsin G, or pepsin.

9. The method of claim 8, wherein the protease that cleaves the wild type IgG1 molecule between or at residues 222-237 is MMP-3, MMP-7, MMP-12, MMP-13, IdeS, or GluV8.

10. The method of claim 1, wherein the antibody comprises the polypeptide sequence of SEQ ID NOs: 8, 10-15 or 18-20.

11. The method of claim 1, wherein the antibody binds to an antigen on a tumor cell, tumor matrix, or tumor vasculature.

12. The method of claim 11, wherein the antibody binds CD19, CD20, CD22, ErbB1, ErbB2, ErbB3, VEGF, RON or tissue factor.

* * * * *

SEQUENCE LISTING

```
<160> NUMBER OF SEQ ID NOS: 22

<210> SEQ ID NO 1
<211> LENGTH: 234
<212> TYPE: PRT
<213> ORGANISM: Homo sapiens

<400> SEQUENCE: 1

Lys Val Glu Pro Lys Ser Cys Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110
```

```
Lys Ala Leu Pro Ala Pro Ile Glu Lys Thr Ile Ser Lys Ala Lys Gly
            115                 120                 125
Gln Pro Arg Glu Pro Gln Val Tyr Thr Leu Pro Ser Arg Asp Glu
        130                 135                 140
Leu Thr Lys Asn Gln Val Ser Leu Thr Cys Leu Val Lys Gly Phe Tyr
145                 150                 155                 160
Pro Ser Asp Ile Ala Val Glu Trp Glu Ser Asn Gly Gln Pro Glu Asn
                165                 170                 175
Asn Tyr Lys Thr Thr Pro Pro Val Leu Asp Ser Asp Gly Ser Phe Phe
            180                 185                 190
Leu Tyr Ser Lys Leu Thr Val Asp Lys Ser Arg Trp Gln Gln Gly Asn
        195                 200                 205
Val Phe Ser Cys Ser Val Met His Glu Ala Leu His Asn His Tyr Thr
    210                 215                 220
Gln Lys Ser Leu Ser Leu Ser Pro Gly Lys
225                 230
```

```
<210> SEQ ID NO 2
<211> LENGTH: 230
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Hinge start, residue EU 218
<220> FEATURE:
<221> NAME/KEY: DOMAIN
<222> LOCATION: (5)..(5)

<400> SEQUENCE: 2

Thr Val Glu Arg Lys Cys Cys Val Glu Cys Pro Pro Cys Pro Ala Pro
1               5                   10                  15
Pro Val Ala Gly Pro Ser Val Phe Leu Phe Pro Pro Lys Pro Lys Asp
            20                  25                  30
Thr Leu Met Ile Ser Arg Thr Pro Glu Val Thr Cys Val Val Val Asp
        35                  40                  45
Val Ser His Glu Asp Pro Glu Val Gln Phe Asn Trp Tyr Val Asp Gly
    50                  55                  60
Val Glu Val His Asn Ala Lys Thr Lys Pro Arg Glu Glu Gln Phe Asn
65                  70                  75                  80
Ser Thr Phe Arg Val Val Ser Val Leu Thr Val Val His Gln Asp Trp
                85                  90                  95
Leu Asn Gly Lys Glu Tyr Lys Cys Lys Val Ser Asn Lys Gly Leu Pro
            100                 105                 110
Ala Pro Ile Glu Lys Thr Ile Ser Lys Thr Lys Gly Gln Pro Arg Glu
        115                 120                 125
Pro Gln Val Tyr Thr Leu Pro Pro Ser Arg Glu Glu Met Thr Lys Asn
    130                 135                 140
Gln Val Ser Leu Thr Cys Leu Val Lys Gly Phe Tyr Pro Ser Asp Ile
145                 150                 155                 160
Ser Val Glu Trp Glu Ser Asn Gly Gln Pro Glu Asn Asn Tyr Lys Thr
                165                 170                 175
Thr Pro Pro Met Leu Asp Ser Asp Gly Ser Phe Phe Leu Tyr Ser Lys
            180                 185                 190
Leu Thr Val Asp Lys Ser Arg Trp Gln Gln Gly Asn Val Phe Ser Cys
        195                 200                 205
Ser Val Met His Glu Ala Leu His Asn His Tyr Thr Gln Lys Ser Leu
```

Ser Leu Ser Pro Gly Lys
225                 230

<210> SEQ ID NO 3
<211> LENGTH: 23
<212> TYPE: PRT
<213> ORGANISM: Homo sapiens

<400> SEQUENCE: 3

Lys Val Glu Pro Lys Ser Cys Asp Lys Thr His Thr Cys Pro Pro Cys
1               5                   10                  15

Pro Ala Pro Glu Leu Leu Gly
            20

<210> SEQ ID NO 4
<211> LENGTH: 19
<212> TYPE: PRT
<213> ORGANISM: Homo sapiens

<400> SEQUENCE: 4

Thr Val Glu Arg Lys Cys Cys Val Glu Cys Pro Pro Cys Pro Ala Pro
1               5                   10                  15

Pro Val Ala

<210> SEQ ID NO 5
<211> LENGTH: 22
<212> TYPE: PRT
<213> ORGANISM: Artificial sequence
<220> FEATURE:
<223> OTHER INFORMATION: Human sequence of IgG origin

<400> SEQUENCE: 5

Lys Val Glu Pro Lys Ser Cys Asp Lys Thr His Thr Cys Pro Pro Cys
1               5                   10                  15

Pro Ala Pro Pro Val Ala
            20

<210> SEQ ID NO 6
<211> LENGTH: 230
<212> TYPE: PRT
<213> ORGANISM: Artificial sequence
<220> FEATURE:
<223> OTHER INFORMATION: human IgG chimeric sequence

<400> SEQUENCE: 6

Thr Val Glu Arg Lys Cys Cys Val Glu Cys Pro Pro Cys Pro Ala Pro
1               5                   10                  15

Pro Val Ala Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
        130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225             230

<210> SEQ ID NO 7
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 7

Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 8
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 8

```
Lys Val Glu Pro Lys Ser Cys Asp Lys Thr His Thr Cys Pro Pro Cys
1               5                   10                  15

Pro Ala Pro Pro Val Ala Gly Pro Asp Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Glu Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 9
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 9

```
Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80
```

```
Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Ala Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 10
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 10

Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Leu Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Pro Glu Glu
65                  70                  75                  80

Gln Tyr Asn Ser Thr Leu Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205
```

```
Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 11
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 11

```
Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser Phe Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Thr Asn Lys
            100                 105                 110

Ala Leu Pro Ala Pro Glu Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 12
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 12

```
Lys Val Glu Pro Lys Ser Cys Asp Lys Thr His Thr Cys Pro Pro Cys
1               5                   10                  15

Pro Ala Pro Pro Val Ala Gly Pro Asp Val Phe Leu Phe Pro Pro Lys
                20                  25                  30

Pro Lys Asp Thr Leu Met Ile Ser Arg Thr Pro Glu Val Thr Cys Val
```

```
                 35                  40                  45
Val Val Asp Val Ser Phe Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Thr Asn Lys
                100                 105                 110

Ala Leu Pro Ala Pro Glu Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 13
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 13

Lys Val Glu Pro Lys Ser Cys Asp Lys Thr His Thr Cys Pro Pro Cys
 1               5                  10                  15

Pro Ala Pro Pro Val Ala Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Glu Phe Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Thr Asn Lys
                100                 105                 110

Ala Leu Pro Ala Pro Glu Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
```

```
                165                 170                 175
Tyr Lys Thr Thr Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 14
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 14

Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
            85                  90                  95

Gln Asp Trp Leu Asn Gly Lys Glu Tyr Lys Cys Lys Val Ser Asn Ala
        100                 105                 110

Ala Leu Pro Ala Pro Ile Ala Lys Thr Ile Ser Lys Ala Lys Gly Gln
    115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 15
<211> LENGTH: 233
<212> TYPE: PRT
<213> ORGANISM: Artificial sequence
<220> FEATURE:
<223> OTHER INFORMATION: human IgG constant region sequence variant
<220> FEATURE:
<221> NAME/KEY: MUTAGEN
<222> LOCATION: (23)..(23)
```

-continued

<223> OTHER INFORMATION: X may be Ala, Asp, Pro, Gln, or Ser

<400> SEQUENCE: 15

```
Lys Val Glu Pro Lys Ser Cys Asp Lys Thr His Thr Cys Pro Pro Cys
1               5                   10                  15

Pro Ala Pro Pro Val Ala Xaa Pro Asp Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Glu Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 16
<211> LENGTH: 230
<212> TYPE: PRT
<213> ORGANISM: Artificial sequence
<220> FEATURE:
<223> OTHER INFORMATION: human IgG constant region sequence variant

<400> SEQUENCE: 16

```
Thr Val Glu Arg Lys Cys Cys Val Glu Cys Pro Pro Cys Pro Ala Pro
1               5                   10                  15

Pro Val Ala Gly Pro Asp Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110
```

Ala Pro Glu Glu Lys Thr Ile Ser Lys Ala Lys Gly Gln Pro Arg Glu
         115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225             230

<210> SEQ ID NO 17
<211> LENGTH: 230
<212> TYPE: PRT
<213> ORGANISM: Artificial sequence
<220> FEATURE:
<223> OTHER INFORMATION: human IgG constant region sequence variant

<400> SEQUENCE: 17

Thr Val Glu Arg Lys Cys Cys Val Glu Cys Pro Pro Cys Pro Ala Pro
1               5                   10                  15

Pro Val Ala Gly Pro Asp Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Phe Arg Val Val Ser Val Leu Thr Val Val His Gln Asp Trp
                85                  90                  95

Leu Asn Gly Lys Glu Tyr Lys Cys Lys Val Ser Asn Lys Gly Leu Pro
            100                 105                 110

Ala Pro Glu Glu Lys Thr Ile Ser Lys Thr Lys Gly Gln Pro Arg Glu
         115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ser Val Glu Trp Glu Ser Asn Gly Gln Pro Glu Asn Asn Tyr Lys Thr
                165                 170                 175

Thr Pro Pro Met Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225             230

```
<210> SEQ ID NO 18
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 18
```

Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Ala
            100                 105                 110

Ala Leu Pro Ala Pro Glu Ala Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

```
<210> SEQ ID NO 19
<211> LENGTH: 233
<212> TYPE: PRT
<213> ORGANISM: Artificial sequence
<220> FEATURE:
<223> OTHER INFORMATION: humang IgG constant region sequence variant

<400> SEQUENCE: 19
```

Lys Val Glu Pro Lys Ser Cys Asp Lys Thr His Thr Cys Pro Pro Cys
1               5                   10                  15

Pro Ala Pro Pro Val Ala Gly Pro Asp Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu

```
                65                  70                  75                  80
Gln Tyr Asn Ser Thr Tyr Arg Val Val Ser Val Leu Thr Val Leu His
                    85                  90                  95

Gln Asp Trp Leu Asn Gly Lys Glu Tyr Lys Cys Lys Val Ser Asn Ala
                100                 105                 110

Ala Leu Pro Ala Pro Ile Ala Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 20
<211> LENGTH: 233
<212> TYPE: PRT
<213> ORGANISM: Artificial sequence
<220> FEATURE:
<223> OTHER INFORMATION: human IgG constant region sequence variant

<400> SEQUENCE: 20

Lys Val Glu Pro Lys Ser Cys Asp Lys Thr His Thr Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Glu His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                    85                  90                  95

Gln Asp Trp Leu Asn Gly Lys Glu Tyr Lys Cys Lys Val Ser Asn Lys
                100                 105                 110

Ala Leu Pro Ala Pro Glu Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
```

```
                195                 200                 205
        Phe Ser Cys Ser Val Met His Glu Ala Leu His Asn His Tyr Thr Gln
            210                 215                 220

Lys Ser Leu Ser Leu Ser Pro Gly Lys
        225                 230

<210> SEQ ID NO 21
<211> LENGTH: 987
<212> TYPE: DNA
<213> ORGANISM: Artificial Sequence
<220> FEATURE:
<223> OTHER INFORMATION: 2h S239D/I332E cDNA

<400> SEQUENCE: 21
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa ggtcgagcct     300
aagagctgcg acaagaccca tacctgccca ccctgtcccg caccccgt cgcagggccg       360 gatgtcttcc tgttcccacc gaaaccgaag gataccctga tgatcagccg gaccccgag     420 gtgacctgcg tggtggtgga cgtgagccac gaggaccccg aagtgaagtt caactggtat     480
gtggacggcg tcgaggtcca caatgccaag accaaccgc gagaggaaca gtacaacagc     540
acgtaccggg tggtgagcgt gctgaccgtg ctgcaccagg actggctgaa cggcaaggag     600
tacaagtgca aggtgagcaa taaagcactg cctgctcccg aggaaaaaac catctccaaa     660
gccaaagggc agccccgaga accacaggtg tacaccctgc ccccatcccg ggatgagctg     720
accaagaacc aggtcagcct gacctgcctg gtcaaaggct tctatcccag cgacatcgcc     780
gtggagtggg agagcaatgg gcagccggag aacaactaca agaccacgcc tcccgtgctg     840
gactccgacg gctccttctt cctctacagc aagctcaccg tggacaagag caggtggcag     900
caggggaacg tcttctcatg ctccgtgatg catgaggctc tgcacaacca ctacacgcag     960
aagagcctct ccctgtctcc gggtaaa                                          987

<210> SEQ ID NO 22
<211> LENGTH: 987
<212> TYPE: DNA
<213> ORGANISM: Artificial Sequence
<220> FEATURE:
<223> OTHER INFORMATION: 2h S239D/K326A/E333A cDNA

<400> SEQUENCE: 22
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa ggtcgagccc     300
aaaagctgcg acaagaccca cgtgcccg ccatgtcctg cccctcccgt cgcaggcccc       360
gacgtgttcc tgttcccacc caagccgaag gacaccctga tgatcagccg gacccccgag     420
gtgacgtgcg tggtggtgga cgtgagccat gaagaccccg aggtgaagtt caactggtac     480
gtggacggcg tggaggtgca caacgccaag accaaccccc gggaagagca gtacaacagc     540
```

```
acctaccggg tggtgagcgt gctgaccgtg ctgcaccagg actggctgaa cggcaaggag    600
tacaagtgca aggtgagcaa cgccgccctc ccagccccca tcgccaaaac catctccaaa    660
gccaaagggc agccccgaga accacaggtg tacaccctgc ccccatcccg ggatgagctg    720
accaagaacc aggtcagcct gacctgcctg gtcaaaggct tctatcccag cgacatcgcc    780
gtggagtggg agagcaatgg gcagccggag aacaactaca agaccacgcc tcccgtgctg    840
gactccgacg gctccttctt cctctacagc aagctcaccg tggacaagag caggtggcag    900
caggggaacg tcttctcatg ctccgtgatg catgaggctc tgcacaacca ctacacgcag    960
aagagcctct ccctgtctcc gggtaaa                                        987
```